(12) United States Patent
Brittenham et al.

(10) Patent No.: US 9,999,382 B2
(45) Date of Patent: Jun. 19, 2018

(54) MEASUREMENT OF A FLUORESCENT ANALYTE USING TISSUE EXCITATION

(71) Applicant: The Trustees of Columbia University in the City of New York, New York, NY (US)

(72) Inventors: Gary M Brittenham, New York, NY (US); Herbert Stepp, Planegg (DE); Georg Hennig, Ottobrunn (DE)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 513 days.

(21) Appl. No.: 14/212,557

(22) Filed: Mar. 14, 2014

(65) Prior Publication Data
US 2014/0235973 A1    Aug. 21, 2014

Related U.S. Application Data

(63) Continuation of application No. PCT/US2012/055492, filed on Sep. 14, 2012.
(Continued)

(51) Int. Cl.
*A61B 5/1455*    (2006.01)
*A61B 5/145*     (2006.01)
(Continued)

(52) U.S. Cl.
CPC .......... *A61B 5/1455* (2013.01); *A61B 5/0071* (2013.01); *A61B 5/0075* (2013.01);
(Continued)

(58) Field of Classification Search
CPC ... A61B 5/0059; A61B 5/1459; A61B 5/0071; A61B 5/14532; G01N 21/6428
See application file for complete search history.

(56) References Cited

U.S. PATENT DOCUMENTS 5,222,495 A * 6/1993 Clarke ............... A61B 5/14532
                                                    356/41
5,279,793 A * 1/1994 Glass ..................... G01N 13/04
                                                    250/227.14
(Continued)

FOREIGN PATENT DOCUMENTS

| WO | 2010132990 | 11/2010 |
| WO | 2011063032 | 5/2011 |
| WO | 2011088580 | 7/2011 |

OTHER PUBLICATIONS

Supplementary Partial European Search Report EP12830997.

*Primary Examiner* — Eric Winakur
*Assistant Examiner* — Marjan Fardanesh
(74) *Attorney, Agent, or Firm* — Reed Smith LLP; Lisa A. Chiarini

(57) ABSTRACT

An apparatus and method for noninvasive measurement of a fluorescent analyte concentration in the blood of a patient by exciting the blood and the analyte at two wavelength ranges and measuring the emission spectrum of the fluorescent analyte when (i) the difference of emission intensities at the excitation wavelength ranges of the fluorescent analyte is greater than that of background fluorophores, and (ii) when blood absorbance at the two excitation wavelength ranges is similar. An apparatus and method for measurement of a fluorescent analyte concentration in the blood of a patient is provided.

20 Claims, 42 Drawing Sheets

Related U.S. Application Data

(60) Provisional application No. 61/535,064, filed on Sep. 15, 2011.

(51) Int. Cl.
*G02B 26/00* (2006.01)
*A61B 5/00* (2006.01)
*A61K 49/00* (2006.01)

(52) U.S. Cl.
CPC ........ *A61B 5/0088* (2013.01); *A61B 5/14546* (2013.01); *G02B 26/001* (2013.01); *A61B 5/7275* (2013.01); *A61B 5/74* (2013.01); *A61K 49/0036* (2013.01)

(56) References Cited

U.S. PATENT DOCUMENTS

| | | | |
|---|---|---|---|
| 5,341,805 A * | 8/1994 | Stavridi | A61B 5/0071 356/317 |
| 6,449,500 B1 * | 9/2002 | Asai | A61B 5/0059 250/227.28 |
| 6,485,703 B1 | 11/2002 | Cote | |
| 6,615,061 B1 * | 9/2003 | Khalil | G01N 21/49 600/310 |
| 7,061,622 B2 | 6/2006 | Rollins et al. | |
| 7,251,516 B2 * | 7/2007 | Walker | A61B 5/14532 600/316 |
| 2002/0151772 A1 * | 10/2002 | Polak | A61B 5/14532 600/310 |
| 2004/0259270 A1 * | 12/2004 | Wolf | A61B 5/076 436/518 |
| 2007/0197880 A1 * | 8/2007 | Maynard | A61B 5/0071 600/300 |
| 2007/0285659 A1 * | 12/2007 | Hsieh | G01J 3/02 356/308 |
| 2008/0001735 A1 | 1/2008 | Tran | |
| 2008/0125636 A1 * | 5/2008 | Ward | A61B 5/7475 600/365 |
| 2009/0312616 A1 | 12/2009 | Paseman | |
| 2010/0022859 A1 * | 1/2010 | Al-Ali | A61B 5/14552 600/310 |
| 2010/0022860 A1 * | 1/2010 | Rebec | A61B 5/0059 600/316 |
| 2010/0243876 A1 | 9/2010 | Resch-Genger | |

* cited by examiner

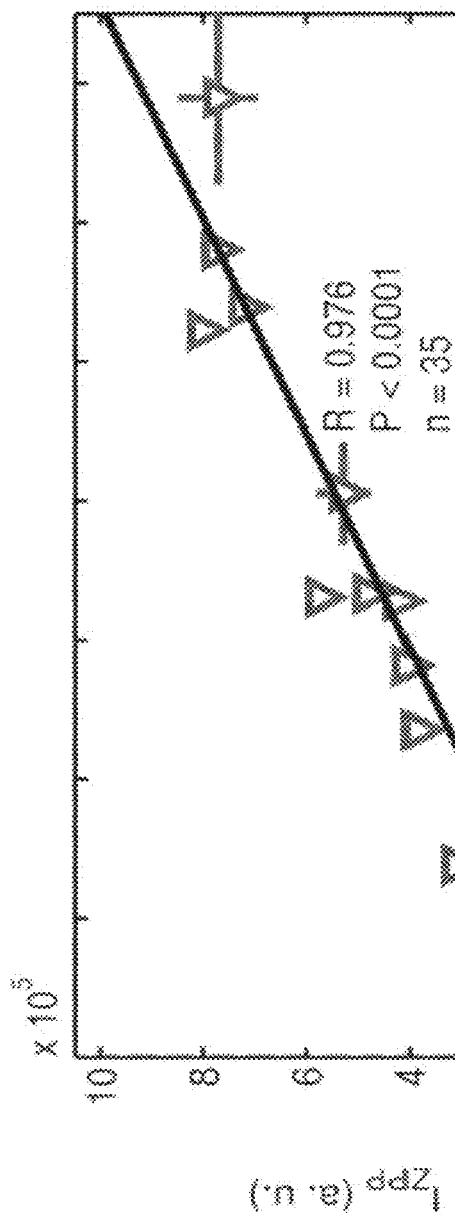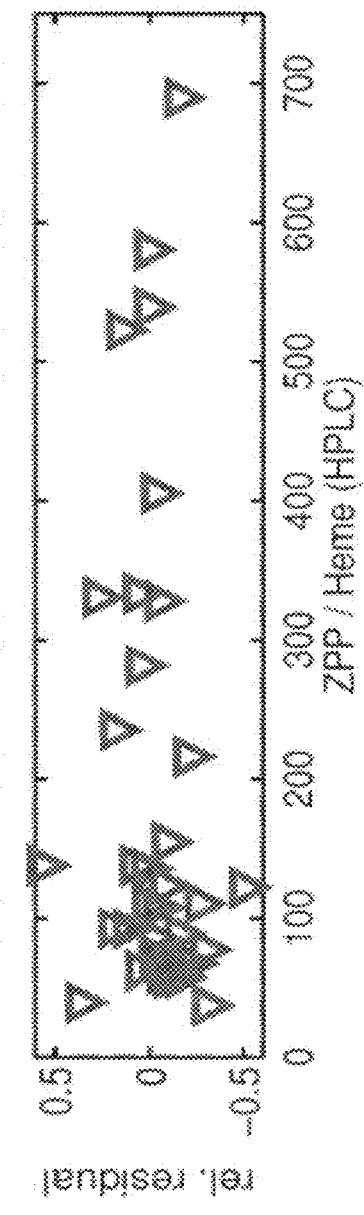
FIGURE 44
FIGURE 45

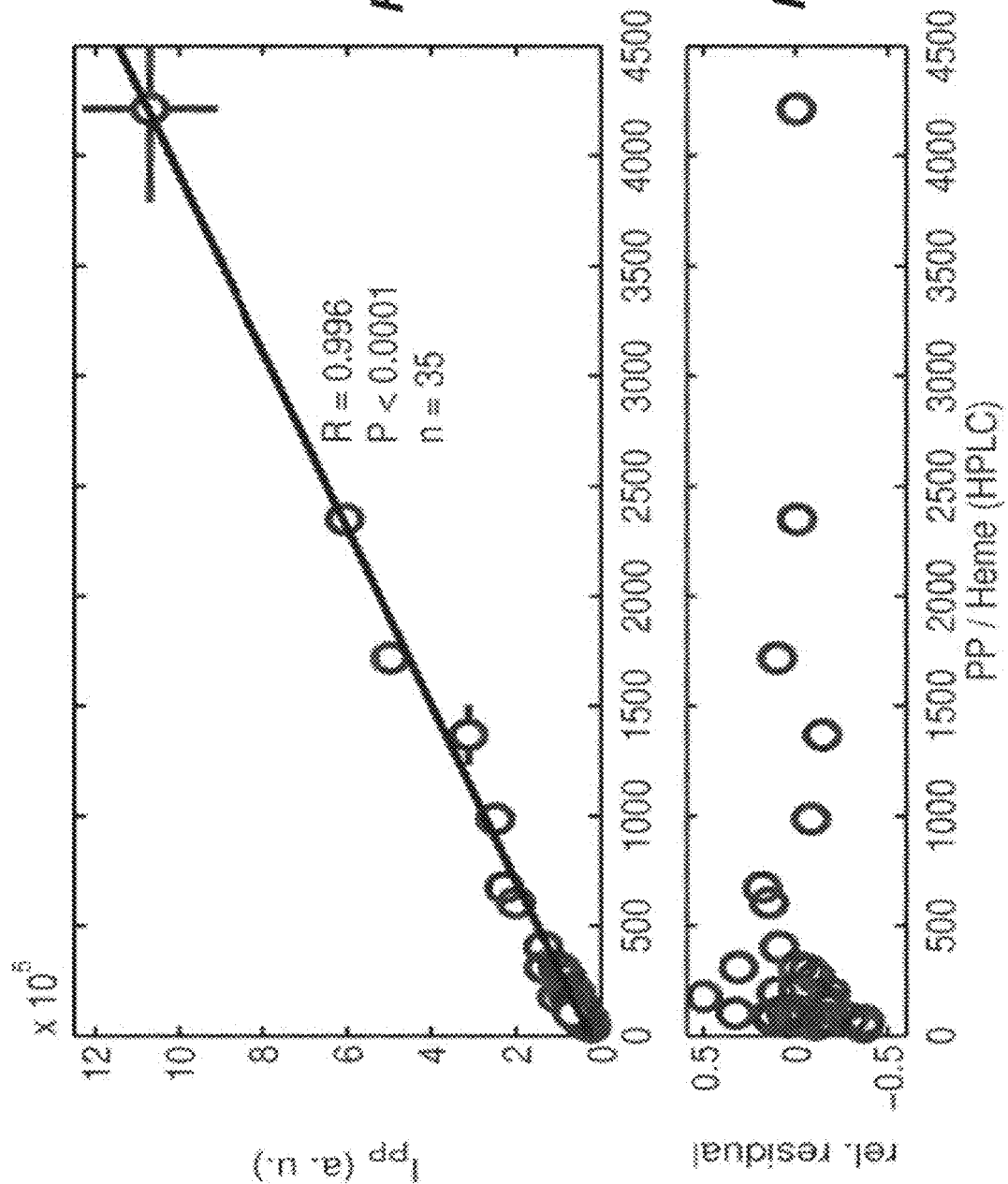

MEASUREMENT OF A FLUORESCENT ANALYTE USING TISSUE EXCITATION

CROSS-REFERENCE TO RELATED APPLICATIONS

This application is a continuation of PCT/US2012/055492, filed Sep. 14, 2012, which claims priority to U.S. Provisional Application 61/535,064, filed Sep. 15, 2011, which are incorporated by reference in their entirety herein.

TECHNICAL FIELD

An apparatus and method for measurement of one or more fluorescent analyte concentration(s) in the blood of a patient by exciting the blood and the analyte at two wavelengths. More particularly, the apparatus and method measure the concentration of erythrocyte zinc protoporphyrin (referred to herein as "eZnPP" or "ZnPP") and erythrocyte protoporphyrin IX (referred to herein as "ePP" or "PP") in the red blood cells of a patient.

BACKGROUND

Iron deficiency remains the most common form of malnutrition worldwide, increasing the risk of disability and death among more than two billion people. Lack of iron causes anemia, decreases physical capabilities, impairs cognitive and behavioral development, compromises immune responsiveness and when severe, increases mortality during infancy and childhood. Iron supplements are needed for prevention of iron deficiency in those with increased iron requirements, especially infants, children and women of childbearing age, and for correction of iron deficiency anemia in all affected individuals.

However, in areas with endemic malaria, untargeted iron supplementation is no longer recommended as a means of providing additional iron because an increased risk of hospitalization and death was found in a trial of universal iron and folic acid supplementation for preschool children in Pemba, Tanzania. Using an elevated eZnPP/heme molar ratio (>80 μmol/mol heme) as the criterion for iron deficiency, iron-deficient children were found to benefit from supplementation. Their risk of severe illness and death decreased by 38%. In contrast, iron-replete children were harmed by supplementation. In fact, their risk of severe illness and death increased by 63% after iron supplementation. See, e.g., Sazawal S. et al., *Effects of routine prophylactic supplementation with iron and folic acid on admission to hospital and mortality in preschool children in a high malaria transmission setting: community-based, randomised, placebo-controlled trial. Lancet* 2006; 367: 133-143. In view of this risk, a World Health Organization (WHO) Consultation recommended that, in malaria-endemic areas, (i) iron supplements should be given to children only after screening for iron deficiency and (ii) the measurement of eZnPP was the preferred indicator for identifying iron-deficient children who could benefit from iron supplementation. See, *WHO Conclusions and recommendations of the WHO Consultation on prevention and control of iron deficiency in infants and young children in malaria-endemic areas. Food Nutr Bull* 2007; 28: S621-7.

In resource-limited settings, like those in regions with endemic malaria, the use of the existing front-face hematofluorometer technique for measurement of eZnPP is constrained by the requirement for a blood sample obtained by finger- or venipuncture, the necessity for a trained technician for operation, use of an electrical power supply, a need for frequent recalibration and expense. Other currently available means of assessing iron status also require blood samples and even more complex and costly laboratory facilities and processing. Because of the lack of means to determine iron status, the effective result of the WHO recommendation has been the cessation of programs of iron supplementation in almost all malarial areas.

Thus, there is a need for a new technique that overcomes the technical difficulties of existing invasive techniques for identifying those individuals in malarial areas who would benefit from iron supplementation to permit safe and effective prevention and correction of iron deficiency, while avoiding harm to those who are iron replete.

Globally, 30% to 70% of the populations in developing countries are iron deficient, with the highest prevalence among persons who have diets low in bio-available iron. In developed countries, despite increased amounts of dietary bio-available iron, iron nutrition nevertheless remains a problem in subpopulations with the highest iron requirements, especially among infants, children and women of childbearing age. Without iron supplementation, most women will become iron deficient during pregnancy. Thus, screening for iron deficiency is a crucial component of healthcare. Initially, iron deficiency may be asymptomatic or produce only nonspecific manifestations, such as weakness and easy fatigability. As iron deficiency becomes more severe, anemia develops and progressively restricts work capacity and tolerance of physical exertion. Early detection of iron deficiency permits prompt recognition and management of underlying causes. Most commonly, a diet with inadequate amounts of bio-available iron is responsible. In these individuals, iron deficiency may be corrected by nutritional approaches, such as consuming iron-rich food as well as food which helps the body absorb iron more effectively, such as food high in vitamin C, or by iron supplementation.

Thus, there is also a need for periodic iron monitoring in a safe, effective manner without the need for a blood sample. There is also a need to provide a technique and apparatus that can be used as a point-of-care screening device for iron deficiency in pediatric, obstetric and medical facilities, and in blood donation centers worldwide, and by individuals to monitor their own iron status in their homes or portably, without the need to be in a clinical setting. Because eZnPP is also elevated in lead poisoning, a noninvasive method would be useful for screening those people at risk from occupational or environmental exposure.

There is also a need to provide a technique and apparatus for measuring the concentration of an analyte in the blood of a patient. For example, in certain settings—such as a hospital or clinical environment with access to sterile conditions and adequate equipment—it is acceptable and/or desirable to analyze iron levels in the blood. A technique and apparatus which provides greater accuracy and consistency when compared with existing techniques is needed.

SUMMARY

In one aspect, an apparatus for noninvasive measurement of a concentration of one or more fluorescent analyte(s) in the blood of a patient is provided which includes a light source for providing excitation of the analyte and the blood at a first wavelength range and a second wavelength range, the first and second excitation wavelength ranges selected such that the analyte exhibits a difference in emission intensities at the first and second excitation wavelength ranges and such that light absorbance of blood at the first and second wavelength ranges is similar; one or more detectors for detecting a portion of the emission spectra of the fluorescent analyte at the first excitation wavelength range and the second excitation wavelength range; and a processor adapted to determine a derived signal representative of the concentration of the analyte based on the difference between the portion of the emission spectra excited at the first excitation wavelength range and the second excitation wavelength range.

In some embodiments, the apparatus is for measurement of a concentration of one or more fluorescent analyte(s) in whole blood.

In some embodiments, a tunable filter unit is provided which excites the blood and the analyte(s) at the first wavelength range and the second wavelength range. In some embodiments, the tunable filter unit includes a first optical filter and a second optical filter, the first and second optical filters are capable of independent variation of the angle of incidence of light provided by the light source. In some embodiments, the tunable filter unit includes two tunable bandpass filters, (such as Semrock Versachrome® filters). In some embodiments, the tunable filter unit includes a first optical filter and a second optical filter and a third optical element to correct for offset of the light passing through the first and second optical filters.

In some embodiments, the apparatus further includes one or more optical filters, wherein the emission spectra of the fluorescent analyte defines a wavelength range, and wherein the detector includes one or more light sensitive elements receiving light through the one or more optical filters transmitting light in the wavelength range of the emission spectra of the fluorescent analyte.

In some embodiments, the emission spectra of the fluorescent analyte define an emission maximum, wherein a first portion of the detector receives light through the optical filters transmitting light in the wavelength range of the emission spectra of the fluorescent analyte, and wherein a second portion of the detector receives light through optical filters transmitting light in a wavelength range outside the emission maximum of the fluorescent analyte.

In some embodiments, the light source is a lamp, one or more laser diodes, or one or more light emitting diodes.

In some embodiments, the apparatus further includes an optical fiber associated with the light source. In some embodiments, the apparatus further includes an optical fiber associated with the detector.

In some embodiments, the apparatus further includes a probe including an optical fiber associated with the light source and an optical fiber associated with the detector. In some embodiments, the probe includes a plurality of optical fibers associated with the light source surrounding an optical fiber associated with the detector.

In some embodiments, the interfiber spacing of the optical fiber associated with the light source and the optical fiber associated with the detector is selected such that the derived signal is insensitive to the blood volume fraction.

In some embodiments, the interfiber spacing of the optical fiber associated with the light source and the optical fiber associated with the detector is selected to achieve a maximum detection sensitivity at a selected depth of the tissue. In some embodiments, the selected depth of the tissue is selected as the depth having the highest expected concentration of the fluorescent analyte.

In some embodiments, the apparatus further includes a power source. In some embodiments, the power source is a rechargeable battery.

In some embodiments, the apparatus includes a housing adapted to receive the detector, the processor and the power source. In some embodiments, the housing is less than 6 inches in length.

In some embodiments, the apparatus includes an output component. In some embodiments, the apparatus includes a housing adapted to receive the detector, the processor and the output component. In some embodiments, the apparatus the output component is a display screen, a speaker or a vibrator.

In some embodiments, the output component provides an indication of the concentration of analyte in the tissue. In some embodiments, the output component provides an indication that the concentration of analyte exceeds a predetermined threshold.

In some embodiments, the apparatus includes memory storing at least one previous concentration of analyte, and wherein the output component is adapted to provide an indication that the concentration of analyte is increasing or decreasing from the previous concentration of analyte.

In some embodiments, the apparatus includes a communications component. In some embodiments, the communications component comprises an RF transmitter, a USB connector, an IR transmitter, a cellular phone or a WiFi transmitter.

A system for noninvasive measurement of a concentration of a fluorescent analyte in the blood of a patient is provided that includes the apparatus described hereinabove, and a monitor unit, wherein the communications component provides an output signal relating to the concentration of analyte to the monitor unit.

In some embodiments, the processor is adapted to provide the output signal to the monitor unit when the analyte concentration exceeds a predetermined threshold.

In some embodiments, the monitor unit comprises a user interface. In some embodiments, the user interface provides an indication of the concentration of analyte in the tissue. In some embodiments, the user interface provides an indication that the concentration of analyte exceeds a predetermined threshold. In some embodiments, the monitor unit comprises memory storing at least one previous concentration of analyte, and wherein the user interface provides an indication that the concentration of analyte is increasing or decreasing from the previous concentration of analyte. In some embodiments, the user interface provides the user with the option of storing a health goal related to the concentration of analyte, and wherein the user interface provides an indication of a trend towards or away from the health goal.

In some embodiments, the user interface provides a treatment suggestion related to the concentration of analyte. In some embodiments, the treatment suggestion comprises ingestion of a quantity of nutrition. In some embodiments, the treatment suggestion comprises administration of a quantity of a pharmaceutical compound.

In some embodiments, the monitor unit is portable. In some embodiments, the monitor unit is a personal computer. In some embodiments, the monitor unit is a telephone.

An apparatus for noninvasive measurement of a concentration of erythrocyte zinc protoporphyrin (eZnPP) as the eZnPP/heme ratio in the blood of a patient is provided which includes a light source for providing excitation of the tissue at a first wavelength range and a second wavelength range, the first excitation wavelength range selected at the excitation peak of eZnPP and the second excitation wavelength range selected so that the absorbance of blood is similar to that of the first excitation wavelength range; one or more detectors for detecting a portion of the emission spectra at the first excitation wavelength range and the second excitation wavelength range; and a processor for determining the concentration of eZnPP based on the difference between the portion of the emission spectra excited at the first excitation wavelength range and the second excitation wavelength range.

In some embodiments, the apparatus is for measurement of a concentration of eZnPP in whole blood.

In some embodiments, a tunable filter unit is provided which excites the blood and eZnPP at the first wavelength range and the second wavelength range. In some embodiments, the tunable filter unit includes a first optical filter and a second optical filter, the first and second optical filters capable of independent variation of the angle of incidence of light provided by the light source. In some embodiments, the tunable filter unit includes two tunable bandpass filters, (such as Semrock Versachrome® filters). In some embodiments, the tunable filter unit includes a first optical filter and a second optical filter and a third optical element to correct for offset of the light passing through the first and second optical filters.

In some embodiments, the apparatus further includes one or more optical filters, wherein the emission spectra of eZnPP defines a wavelength range, and wherein the detector includes one or more light sensitive elements receiving light through the one or more optical filters transmitting light in the wavelength range of the emission spectra of eZnPP.

In some embodiments, the emission spectra of eZnPP define an emission maximum, wherein a first portion of the detector receives light through the optical filters transmitting light in the wavelength range of the emission spectra of eZnPP, and wherein a second portion of the detector receives light through optical filters transmitting light in a wavelength range outside the emission maximum of eZnPP.

In some embodiments, the light source is a lamp, one or more laser diodes, or one or more light emitting diodes.

In some embodiments, the apparatus further includes an optical fiber associated with the light source. In some embodiments, the apparatus further includes an optical fiber associated with the detector.

In some embodiments, the apparatus further includes a probe including an optical fiber associated with the light source and an optical fiber associated with the detector. In some embodiments, the probe includes a plurality of optical fibers associated with the light source surrounding an optical fiber associated with the detector.

In some embodiments, the interfiber spacing of the optical fiber associated with the light source and the optical fiber associated with the detector is selected such that the derived signal is insensitive to the blood volume fraction.

In some embodiments, the interfiber spacing of the optical fiber associated with the light source and the optical fiber associated with the detector is selected to achieve a maximum detection sensitivity at a selected depth of the tissue. In some embodiments, the selected depth of the tissue is selected as the depth having the highest expected concentration of eZnPP.

In some embodiments, the apparatus further includes a power source. In some embodiments, the power source is a rechargeable battery.

In some embodiments, the apparatus includes a housing adapted to receive the detector, the processor and the power source. In some embodiments, the housing is less than 6 inches in length.

In some embodiments, the apparatus includes an output component. In some embodiments, the apparatus includes a housing adapted to receive the detector, the processor and the output component. In some embodiments, the output component is a display screen, a speaker or a vibrator.

In some embodiments, the output component provides an indication of the concentration of eZnPP in the tissue. In some embodiments, the output component provides an indication that the concentration of eZnPP exceeds a predetermined threshold.

In some embodiments, the apparatus includes memory storing at least one previous concentration of eZnPP, and wherein the output component is adapted to provide an indication that the concentration of eZnPP is increasing or decreasing from the previous concentration of analyte.

In some embodiments, the apparatus includes a communications component. In some embodiments, the communications component comprises an RF transmitter, a USB connector, an IR transmitter, a cellular phone or a WiFi transmitter.

A system for noninvasive measurement of a concentration of eZnPP in the blood of a patient is provided which includes the apparatus described hereinabove, and a monitor unit, wherein the communications component provides an output signal relating to the concentration of eZnPP to the monitor unit.

In some embodiments, the processor is adapted to provide the output signal to the monitor unit when the eZnPP concentration exceeds a predetermined threshold.

In some embodiments, the monitor unit comprises a user interface. In some embodiments, the user interface provides an indication of the concentration of eZnPP in the tissue. In some embodiments, the user interface provides an indication that the concentration of eZnPP exceeds a predetermined threshold. In some embodiments, the monitor unit comprises memory storing at least one previous concentration of eZnPP, and wherein the user interface provides an indication that the concentration of eZnPP is increasing or decreasing from the previous concentration of eZnPP. In some embodiments, the user interface provides the user with the option of storing a health goal related to the concentration of eZnPP, and wherein the user interface provides an indication of a trend towards or away from the health goal.

In some embodiments, the user interface provides a treatment suggestion related to the concentration of eZnPP. In some embodiments, the treatment suggestion comprises ingestion of a quantity of nutrition. In some embodiments, the treatment suggestion comprises administration of a quantity of a pharmaceutical compound.

In some embodiments, the monitor unit is portable. In some embodiments, the monitor unit is a personal computer. In some embodiments, the monitor unit is a telephone.

An apparatus for simultaneous measurement of a concentration of erythrocyte zinc protoporphyrin (eZnPP) and erythrocyte protoporphyrin IX (ePP) as the eZnPP/heme ratio and ePP/heme ratio in the blood of a patient is provided including a light source for providing excitation of the tissue at a first wavelength range and a second wavelength range, the first excitation wavelength range selected at the excitation peak of eZnPP and the second excitation wavelength range selected so that the absorbance of blood is similar to that of the first excitation wavelength range; one or more detectors for detecting a portion of the emission spectra at the first excitation wavelength range and the second excitation wavelength range; and a processor for determining the concentration of eZnPP and ePP based on the difference between the portion of the emission spectra excited at the first excitation wavelength range and the second excitation wavelength range.

An apparatus for noninvasive measurement of a concentration of erythrocyte zinc protoporphyrin (eZnPP) as the eZnPP/heme ratio in the blood of a patient is provided including a light source for providing excitation of the tissue at about 425 nm and about 407 nm; a detector for detecting a portion of the emission spectra excited at about 425 nm and about 407 nm; and a processor for determining the concentration of eZnPP based on the difference between the portion of the emission spectra excited at about 425 nm and about 407 nm.

An apparatus for measurement of a concentration of erythrocyte zinc protoporphyrin (eZnPP) as the eZnPP/heme ratio in the blood of a patient is provided including a light source for providing excitation of the tissue at about 425 nm and about 407 nm; a detector for detecting a portion of the emission spectra excited at about 425 nm and about 407 nm; and a processor for determining the concentration of eZnPP based on the difference between the portion of the emission spectra excited at about 425 nm and about 407 nm.

A method for noninvasive measurement of a concentration of a fluorescent analyte in the blood of a patient is provided including exciting the tissue at a first wavelength range and a second wavelength range, the first and second excitation wavelength ranges selected such that the fluorescent analyte exhibits a difference in emission intensities at the first and second excitation wavelength ranges that is greater than that of background fluorophores and light absorbance by blood at the first and second excitation wavelength ranges is similar; detecting a portion of the emission spectra at the first excitation wavelength range and the second excitation wavelength range; and determining the concentration of the fluorescent analyte based on the difference between the emission spectra excited at the first excitation wavelength range and the second excitation wavelength range.

An apparatus for filtering a beam of light is provided including a first optical filter defining an adjustable angle of incidence with respect to the beam of light; a second optical filter defining an adjustable angle of incidence with respect to the beam of light; wherein the angle of incidence of the first optical filter and the angle of incidence of the second optical filter are independently adjustable; wherein a central wavelength of light passing through first and second optical filters is tunable by adjustment of the angle of incidence of the first filter with respect to the beam of light; and wherein the spectral bandwidth of light passing through the first and second optical filters is tunable by adjustment of the angle of incidence of the first filter and the second filter with respect to the beam of light. In some embodiments, the first and second optical filters comprise two tunable bandpass filters, (such as Semrock Versachrome® filters). In some embodiments, a third optical element is provided to correct for offset of the light passing through the first and second optical filters.

BRIEF DESCRIPTION OF FIGURES

FIGS. 44-45 illustrate a correlation between the measured fluorescence intensity of the difference spectrum at 593 nm evaluated by HPLC and a method in accordance with an exemplary embodiment of the subject matter described herein.

FIGS. 46-47 illustrate a correlation between the measured fluorescence intensity of the difference spectrum at 627 nm evaluated by a method in accordance with an exemplary embodiment of the subject matter described herein and the PP/heme ratio measured by HPLC.

DETAILED DESCRIPTION OF EMBODIMENTS

Figure 1:
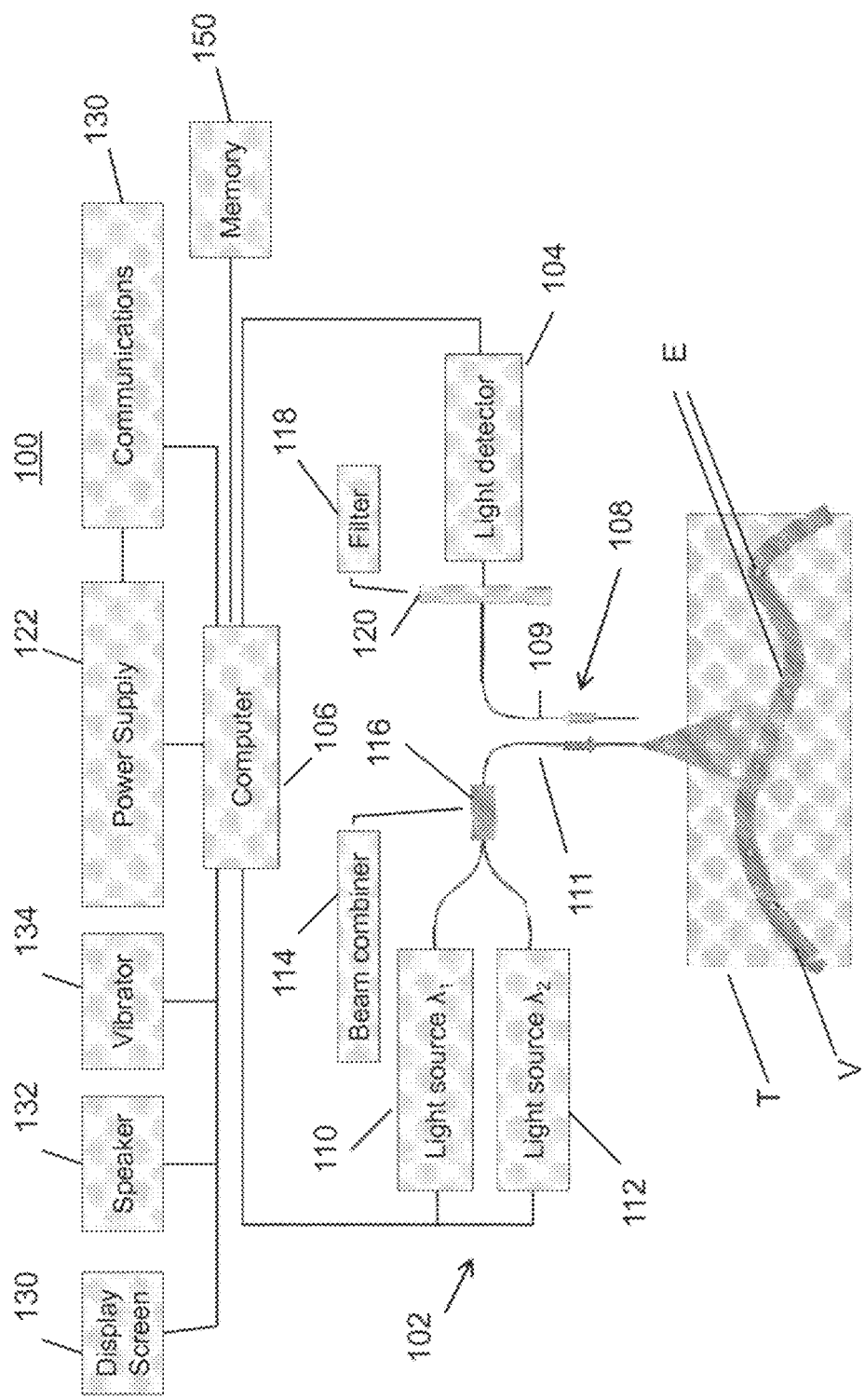
FIG. 1 is a schematic view of an apparatus in accordance with an exemplary embodiment of the subject matter described herein.

It is understood that the subject matter described herein is not limited to particular embodiments described, as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range, and any other stated or intervening value in that stated range, is encompassed within the disclosed subject matter.

Unless defined otherwise, all technical and scientific terms used herein have the same meaning as commonly understood by one of ordinary skill in the art to which this disclosed subject matter belongs. Although any methods and materials similar or equivalent to those described herein can also be used in the practice or testing of the present disclosed subject matter, this disclosure may specifically mention certain exemplary methods and materials.

All publications mentioned in this disclosure are, unless otherwise specified, incorporated by reference herein for all purposes, including, without limitation, to disclose and describe the methods and/or materials in connection with which the publications are cited.

The publications discussed herein are provided solely for their disclosure prior to the filing date of the present application. Nothing herein is to be construed as an admission that the present disclosed subject matter is not entitled to antedate such publication by virtue of prior invention. Further, the dates of publication provided may be different from the actual publication dates, which may need to be independently confirmed.

As used herein and in the appended claims, the singular forms "a," "an" and "the" include plural referents unless the context clearly dictates otherwise.

Nothing contained in the Abstract or the Summary should be understood as limiting the scope of the disclosure. The Abstract and the Summary are provided for bibliographic and convenience purposes and due to their formats and purposes should not be considered comprehensive.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosed subject matter. Any recited method can be carried out in the order of events recited, or in any other order that is logically possible.

Reference to a singular item includes the possibility that there are plural of the same item present. When two or more items (for example, elements or processes) are referenced by an alternative "or," this indicates that either could be present separately or any combination of them could be present together, except where the presence of one necessarily excludes the other or others.

As summarized above and as described in further detail below, in accordance with the various embodiments of the present invention, there is provided an apparatus for measuring fluorescent analyte concentration in the blood and a method for using the apparatus. In some embodiments, the apparatus measures the fluorescent analyte concentration noninvasively, e.g., by exciting intact tissue in the patient, e.g., the oral mucosa. In some embodiments, the apparatus measures the fluorescent analyte concentration by exciting blood samples or other tissue ex vivo.

The apparatus described herein measures the fluorescence of an analyte by excitation of tissue at two alternating wavelengths, or wavelength ranges. The two wavelengths are selected such that the analyte exhibits a greater difference in fluorescence at the two wavelengths (one of which may be at the excitation peak of the analyte) than that of background fluorophores, and at which blood exhibits substantially similar absorbance at the two wavelengths. The degree of similarity can be appropriately determined by those of ordinary skill in the art. To fulfill the requirement of sufficiently similar absorbance of light at the two excitation wavelengths in tissue, the excitation wavelengths can be determined experimentally in a way to minimize the effective penetration depth differences of light at both wavelengths or both wavelength ranges. This may be approximated on a representative sample, which does not contain the analyte, by setting the first excitation wavelength at the known wavelength for maximum excitation efficiency of the analyte and then scanning the excitation wavelength along the other side of the blood absorbance peak until the background fluorescence spectrum has the expected intensity and the most similar shape. An example of this is provided below.

Although the apparatus is described herein with respect to measurement of eZnPP using the absorbance characteristics of blood (e.g., with hemoglobin as the predominant absorber), it is understood that the principles described herein are applicable to measurement of other analytes and reference materials having similar fluorescence and absorbance properties.

eZnPP is an indicator of iron supply to developing red blood cells. During hemoglobin synthesis, if iron deficiency makes iron unavailable to the developing red blood cell to form heme from protoporphyrin IX, then zinc is chelated instead to form eZnPP as one of the first biochemical responses to iron depletion.

The measurement of eZnPP by noninvasive tissue excitation requires a quantitative method to distinguish the fluorescence of eZnPP from that of other fluorophores in tissue, i.e., from tissue autofluorescence. Since eZnPP is found inside erythrocytes only, it has been observed that the "dilution" of the blood by tissue that shows autofluorescence does not in first order destroy the quantitative nature of the derived signal. That is, measurement of eZnPP is insensitive to the concentration of blood within the tissue, i.e., to the value of the blood volume fraction of the tissue, over a certain range. This range of insensitivity to the blood volume fraction can be modified by changing the probe head configuration, i.e., by changing the spatial separation between excitation and detection fiber(s).

In an exemplary embodiment, the fluorometer noninvasively measures eZnPP fluorescence in red blood cells by examination of the microcirculation of the intact oral mucosa at the two alternating excitation wavelengths. The fluorometer can also be used to noninvasively examine other tissue, such as other mucosal surfaces, as well as the skin if permitted by the amount of skin pigmentation. The fluorometer illuminates the mucosa and transmits the induced fluorescence to a photodetector. Diode lasers may be used as the excitation light sources. The fluorometer can also be used to examine tissue samples or blood samples ex vivo.

An exemplary embodiment of the fluorometer 100 is shown schematically in FIG. 1. Fluorometer 100 includes an excitation light source 102 for illuminating the tissue T of the patient, and a light detector 104, such as a spectrophotofluorometer, for analyzing the fluorescence. In some embodiments, two or more detectors are employed, in which part of these detectors receive light through optical filters transmitting light in the wavelength range of the emission wavelength of the analyte and the other part of these detectors receive light through optical filters transmitting light in the wavelength range outside the emission maximum of the analyte. The fluorometer 100 measures the concentration of eZnPP found in erythrocytes E in the blood vessel V of the patient. A processor 106 determines the concentration of eZnPP based on the fluorescence detected by the detector 104.

The provision of light to the tissue T and transmission of fluorescence to the light detector 104 is performed by an optical probe head 108 in an exemplary embodiment. The excitation light source 102 provides radiation for tissue excitation at two wavelengths. In an exemplary embodiment, alternating wavelengths are provided by first and second light sources 110 and 112, such as lasers or LEDs which operate at two wavelengths, e.g., 407 nm and 425 nm. A beam combiner 114 provides the light to the tissue T as a single source in an alternating fashion. The frequency of the alternation is chosen quickly enough to show intensity variations during the measurement, e.g., due to movement of the patient, in both emission spectra in such a way that the variations are reduced or canceled in the difference of the spectra. It has been observed that there are high intensity variations if the patient moves during measurement. However, if the speed of the alternation is sufficiently rapid, these variations are discernible in both emission spectra, and by subtracting them, the variations are canceled out. It has also been observed that measuring the emission spectra in parallel (e.g., with a CCD detector such that all wavelengths are measured simultaneously) avoids the result in which intensity variations due to movement become wavelength-dependent intensity variations ("peaks") in the spectrum. A lens and/or filter 116 can be provided to focus and/or direct the light to the tissue T. Transmission of light from the probe 108 to the light detector 104 is accomplished by one or more optical fibers. A single optical fiber is used to illuminate the tissue and also to transport the fluorescence to the detector. A lens 120 and/or filter 118 can be provided to focus and/or remove noise from the light transmitted to the detector 104. After accounting for background tissue fluorescence, scatter, path length, geometric and other factors, the processor 106 correlates the intensity of the fluorescence to the eZnPP/heme ratio and provides the result in an output device, such as a display screen 130, speaker 132 or vibrating unit 134. An optional communications component 130 is provided in certain embodiments, as will be described in greater detail hereinbelow. An optional power supply 122, such as a battery, can be included in the fluorometer, particularly if it is a portable device. In some embodiments, the fluorometer 100 can be directly connected to the electrical power supply of the home or institution.

Figures 1A, 1B, 1C:
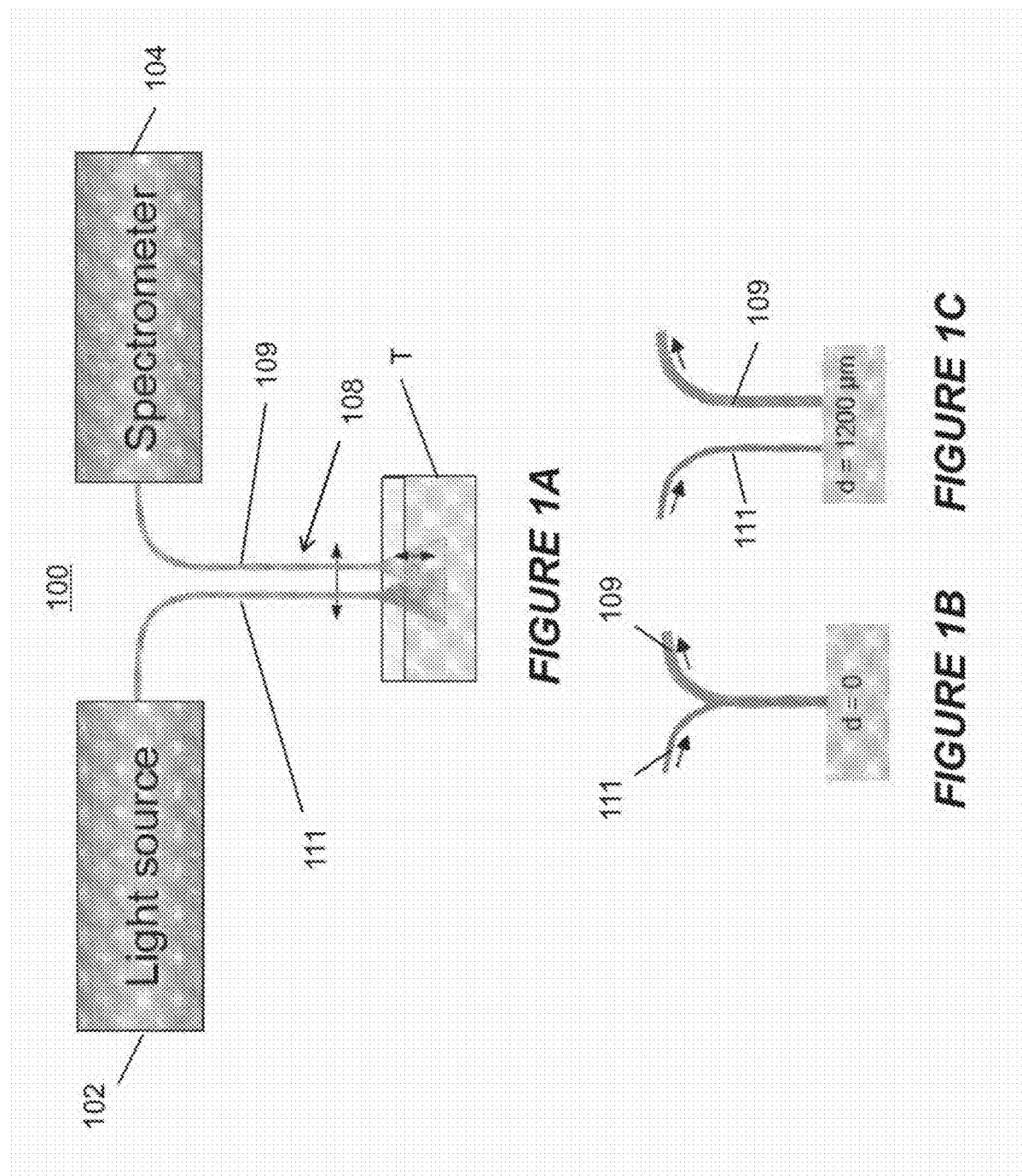
FIG. 1A is a simplified schematic view of an apparatus in accordance with an exemplary embodiment of the subject matter described herein.
FIG. 1B is a simplified schematic view of an apparatus, indicating a first spacing between an excitation fiber and a detection fiber, in accordance with an exemplary embodiment of the subject matter described herein.
FIG. 1C is a simplified schematic view of an apparatus, indicating a second spacing between an excitation fiber and a detection fiber, in accordance with an exemplary embodiment of the subject matter described herein.

Apparatus 100 is illustrated in FIG. 1A which indicates the optical fiber 111 associated with the light source 102, also referred to herein as the excitation fiber, and the optical fiber 109 associated with the light detector, such as spectrometer 104, also referred to herein as the detection fiber. FIG. 1B illustrates a first spacing between excitation fiber 111 and a detection fiber 109, i.e., "interfiber spacing." In FIG. 1B, the interfiber spacing d=0. FIG. 1C illustrates a second interfiber spacing, i.e., a spacing d of about 1200 µm. The interfiber spacing d in probe 108 is selected, e.g., experimentally, to obtain minimal dependence on the blood volume fraction over a physiological relevant range. A photograph of an exemplary embodiment of a portion of the fluorometer is represented in FIG. 2, adapted for measurement of patient blood samples, although such apparatus may be used for tissue measurements as well.

Figure 3:
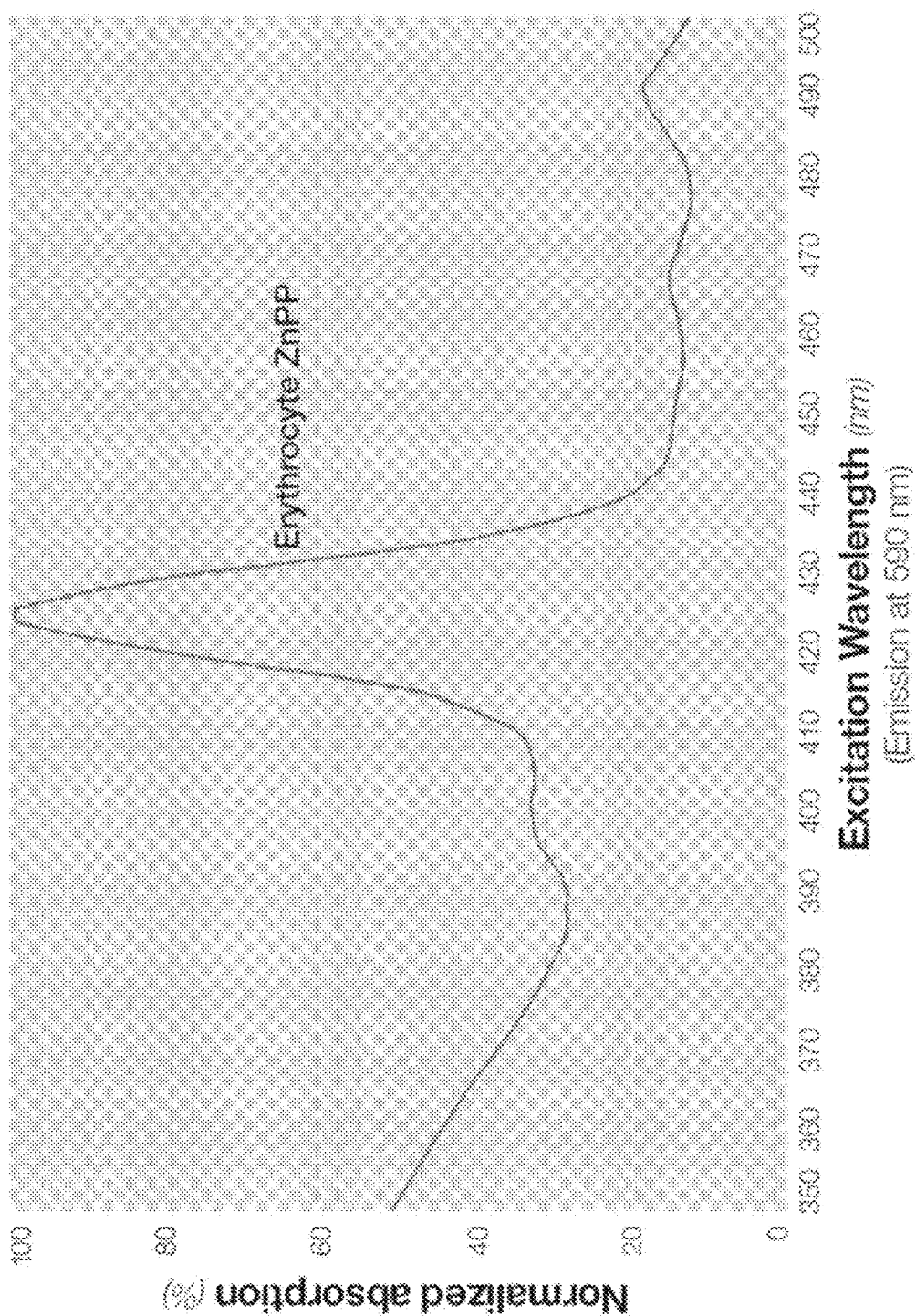
FIG. 3 illustrates the excitation spectra of eZnPP bound to oxyhemoglobin.
Figure 4:
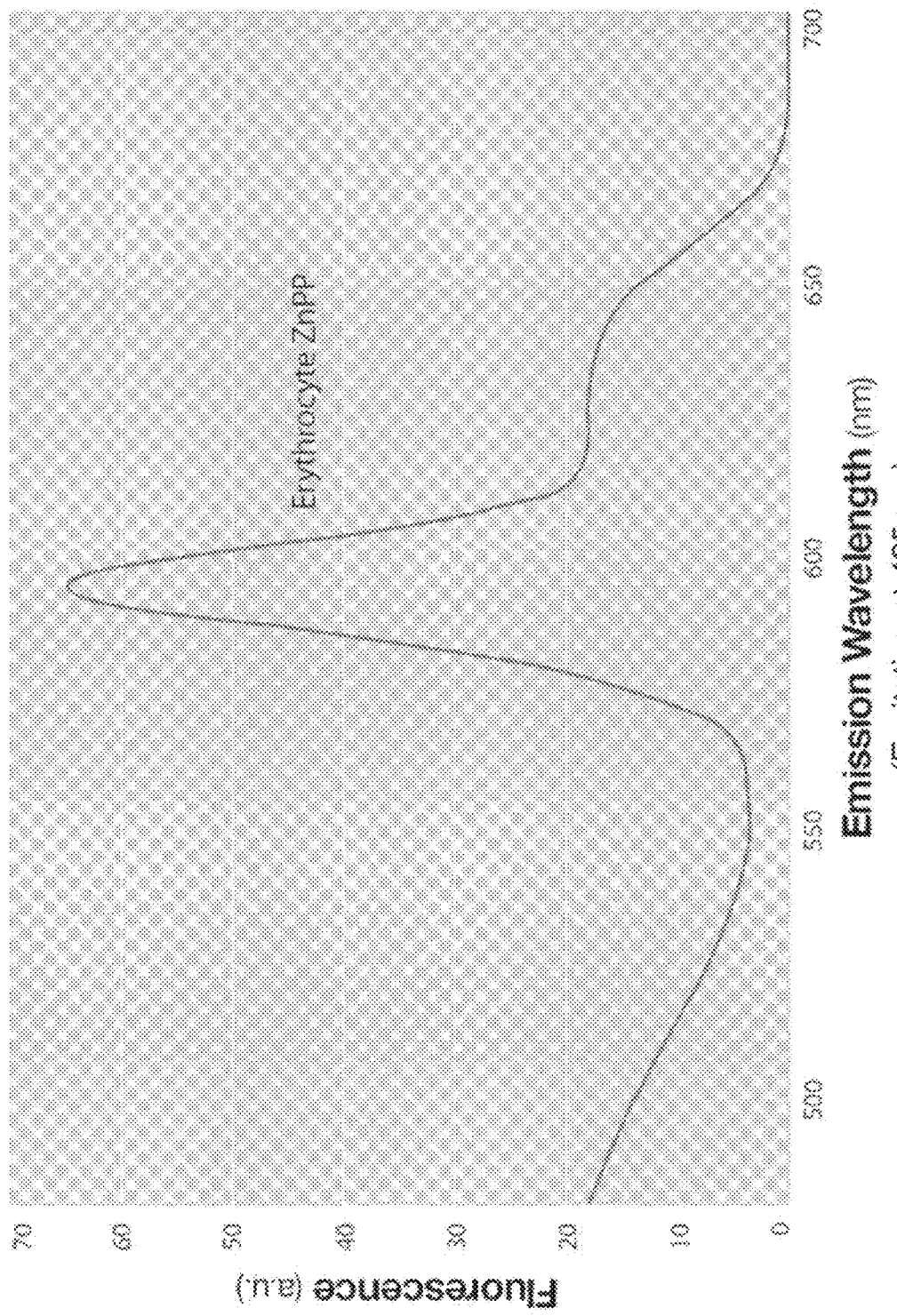
FIG. 4 illustrates the emission spectra of eZnPP bound to oxyhemoglobin.

In measurements of a blood sample on a glass slide, eZnPP is one of the major fluorophores with a dominant, characteristic excitation peak at about 425 nm (FIG. 3) and an emission peak at about 590 nm (FIG. 4). Within the erythrocyte, eZnPP is bound to hemoglobin. Hemoglobin does not fluoresce but strongly absorbs light at 400 to 430 nm. This absorption by hemoglobin diminishes the eZnPP fluorescence. With a front-face hematofluorometer, the hemoglobin and eZnPP in a blood sample on a glass slide absorb almost all the excitation light within a thin surface layer that allows the emitted light to be collected with equal efficiency. The intensity of the emission at 590 nm is proportional to the eZnPP/heme molar ratio.

Figure 2:
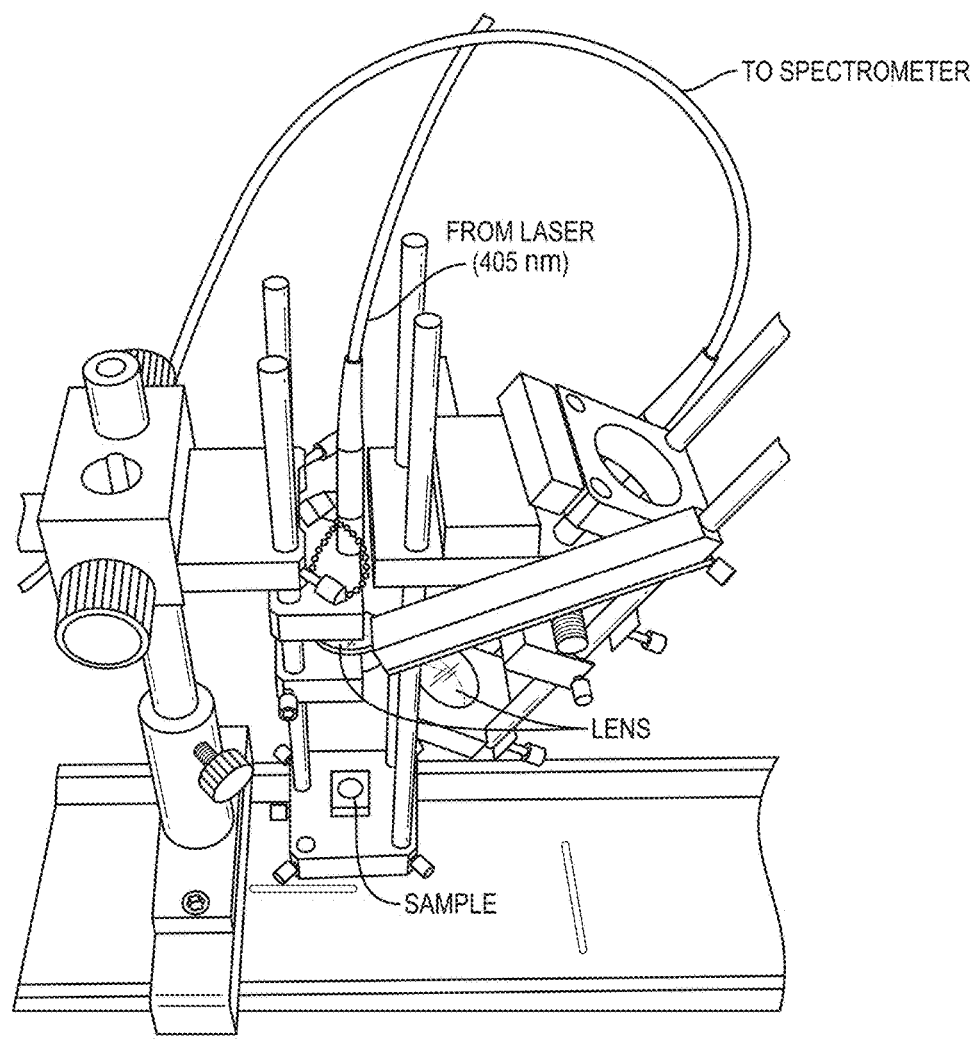
FIG. 2 is a view of an apparatus in a free-beam instrumental configuration in accordance with another exemplary embodiment of the subject matter described herein, adapted for measurement of patient blood samples or tissue.
Figure 13:
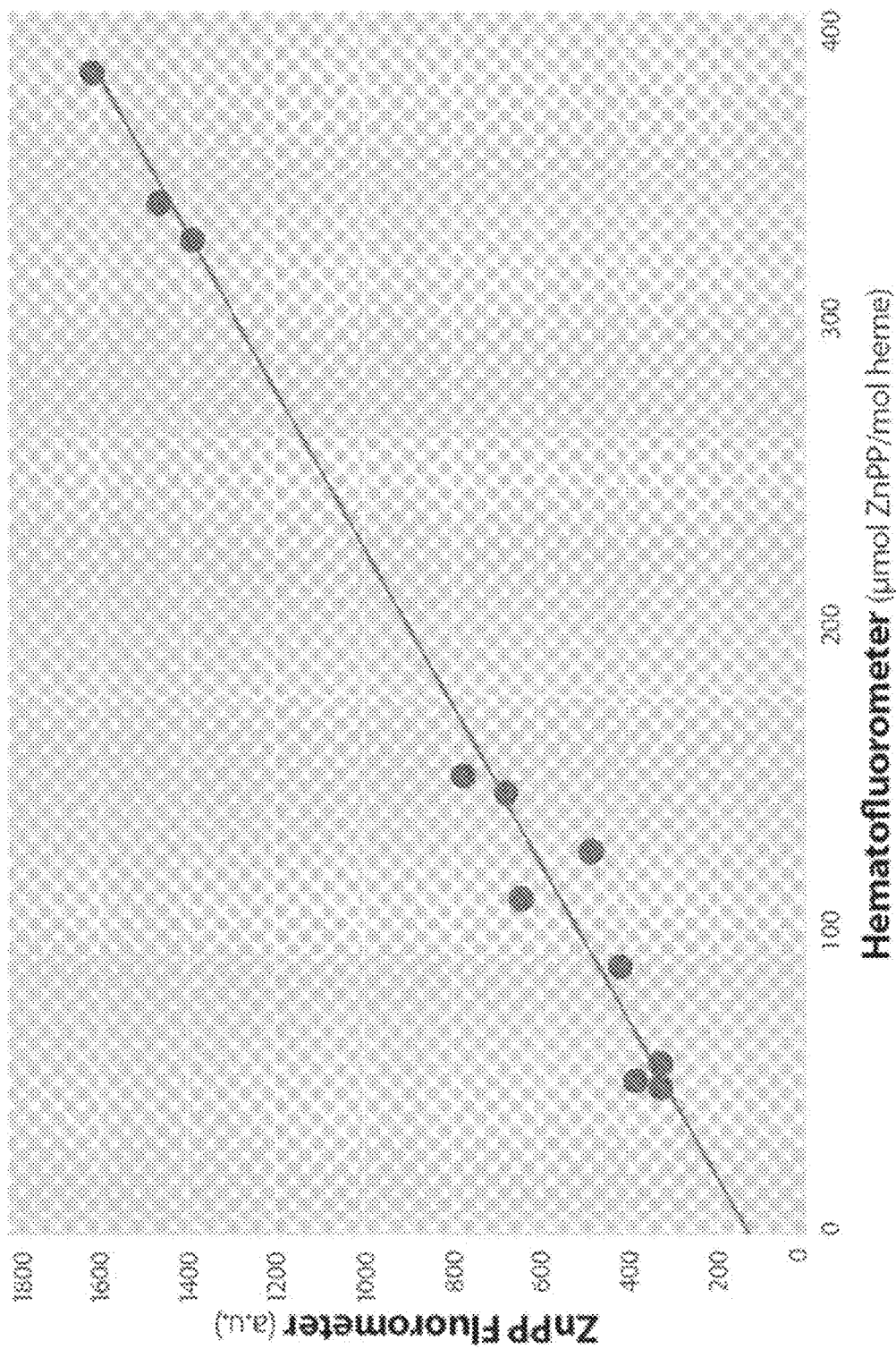
FIG. 13 illustrates a comparison of the output of an apparatus in accordance with an exemplary embodiment shown in FIG. 2 (on the vertical axis) with those provided by an Aviv hematofluorometer (on the horizontal axis) in measurements of the eZnPP/heme ratio on a series of patient blood samples.

FIG. 13 compares measurements of patient blood samples (diluted to 4%) taken by the fluorometer 100 (excitation at 425 nm; emission at 590 nm; measurements in a.u., arbitrary units) in the free-beam instrumental configuration shown in FIG. 2 on the vertical axis, with those by an Aviv hematofluorometer, on the horizontal axis. Overall, the measurements are closely correlated; the remaining scatter may be explained by a greater specificity for eZnPP with the fluorometer 100 compared to the Aviv hematofluorometer.

In contrast to measurement of blood samples on a glass slide, in noninvasive measurement of erythrocytes within an examined tissue, e.g., in the microcirculation of the oral mucosa, eZnPP is a minor fluorophore. Instead, connective tissue (collagen and elastin) is the principal source of autofluorescence from the stromal layers containing the microcirculation. In the thin overlying epithelium of non-keratinized oral mucosa (mucous membranes of the lip, buccal and sublingual mucosa), the dominant fluorophores are mitochondrial reduced nicotinamide adenine dinucleotide (NADH) and mitochondrial flavin adenine dinucleotide (FAD). The absorbance spectrum of NADH does not extend up to 425 nm and, accordingly, will not contribute to fluorescence at the 590 nm emission peak of erythrocyte eZnPP. As will be discussed below, the contribution of epithelial FAD to fluorescence at 590 nm can likely be minimized or eliminated by optimizing the configuration of the excitation and detection fibers in the probe head 108.

Figure 5:
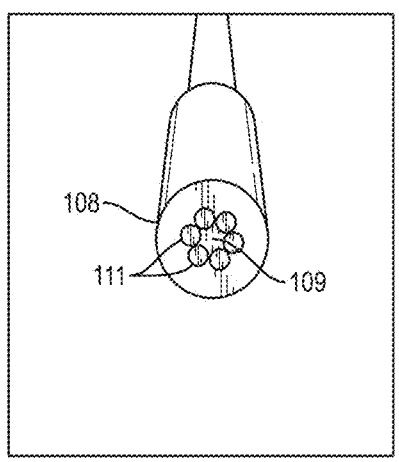
FIG. 5 is a perspective view of a fiber optic probe head in accordance with an exemplary embodiment of the subject matter described herein.
Figure 6:
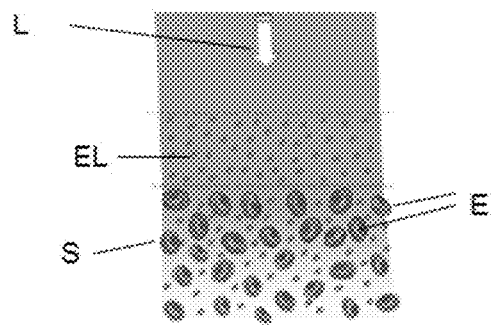
FIG. 6 is a cross-sectional view of tissue receiving the stimulation from the light source of an exemplary apparatus as disclosed in the subject matter herein.

In FIG. 5, an exemplary fiber-optic probe head 108 is illustrated. A central detection fiber 109 is surrounded by one or more (e.g., six) excitation fibers 111. FIG. 6 is a schematic diagram of non-keratinized oral mucosa. The excitation light (indicated by arrow L) must pass through a thin overlying epithelial layer EL with light-scattering elements to reach erythrocytes E in the microcirculation in the stromal layer S, also with light-scattering elements.

Figure 7:
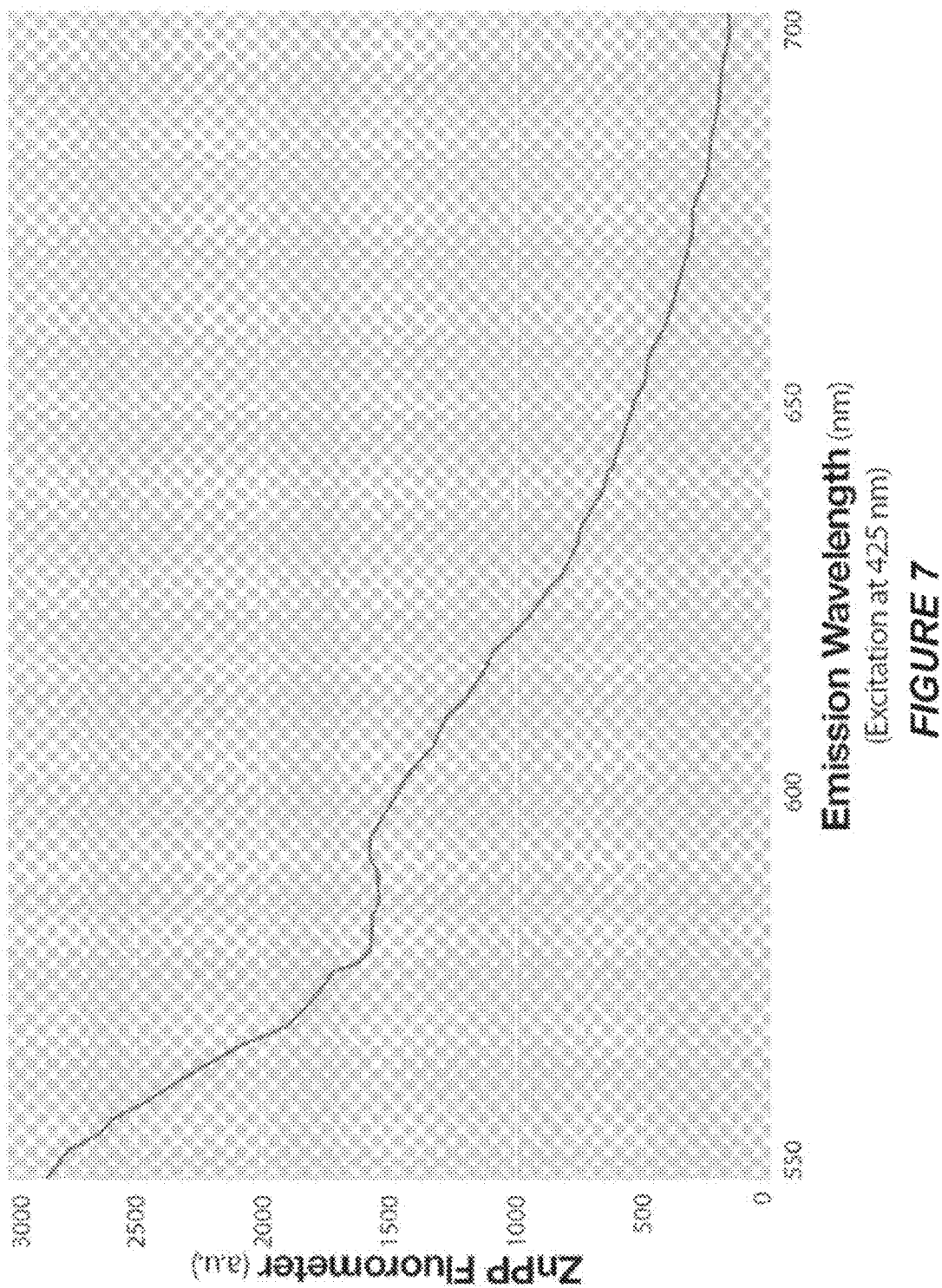
FIG. 7 illustrates the tissue autofluorescence spectrum from oral mucosa obtained using an exemplary apparatus as disclosed in the subject matter herein.

Using the fiber-optic probe head design disclosed in FIG. 5, the tissue autofluorescence spectrum from the mucous membrane of the lower lip of a human patient is shown in FIG. 7. Because the magnitude of the tissue autofluorescence is considerably greater than the fluorescence of erythrocyte eZnPP, some investigators have concluded that measurement in the oral mucosa is not feasible. See, e.g., Chen X. "Feasibility test for noninvasive detection of zinc protoporphyrin in oral mucosa and retina." *Biomedical Engineering* 2007; M.S.: 1-71.

Figure 8:
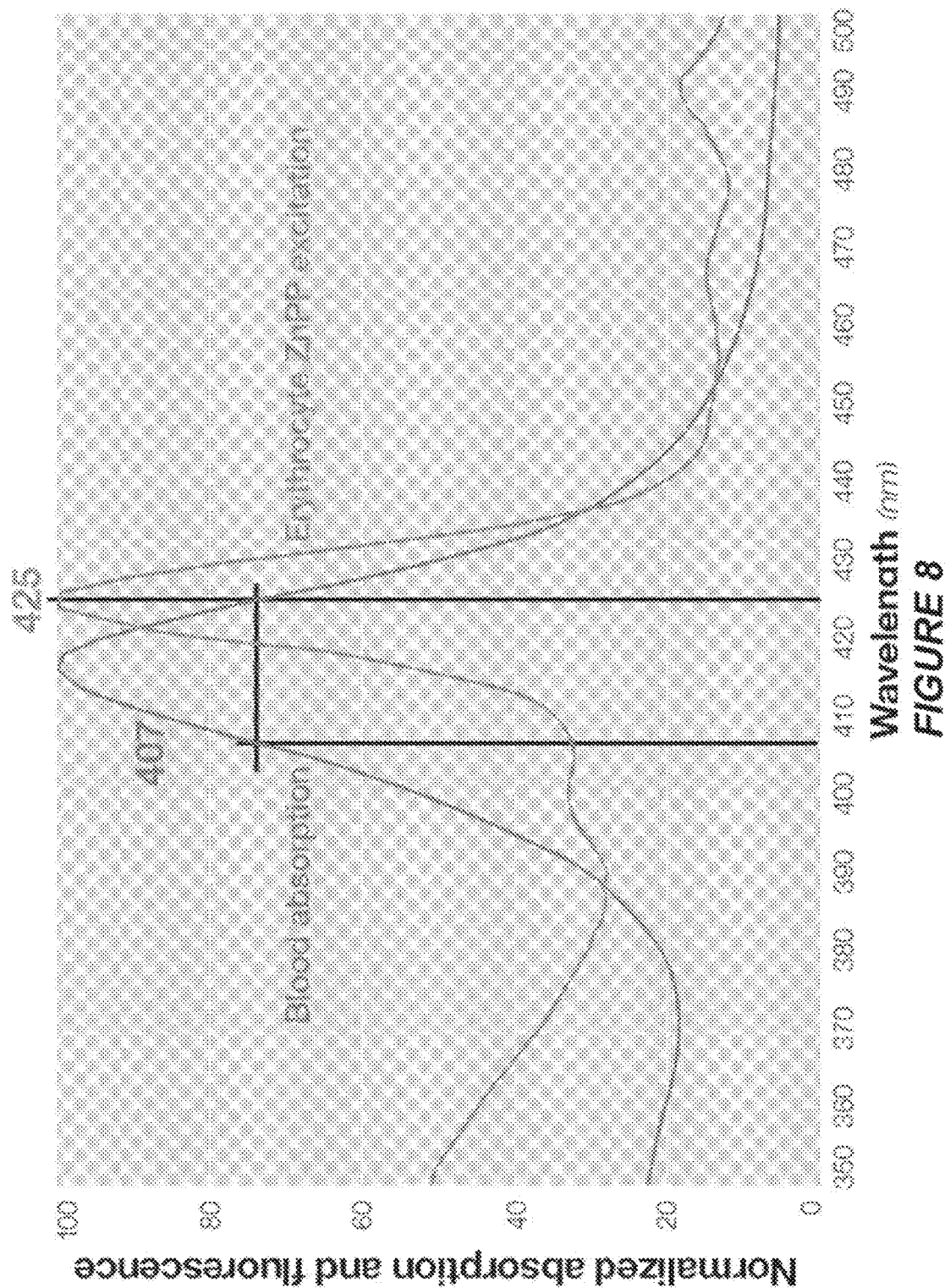
FIG. 8 illustrates the normalized blood absorbance and eZnPP excitation spectrum.

The fluorometer overcomes limitations in the prior art by providing an alternating two-wavelength fluorescence excitation method that is used to distinguish eZnPP fluorescence from tissue autofluorescence. As shown in FIG. 8, the hemoglobin absorbance is the same at the excitation peak for erythrocyte eZnPP (425 nm) and at 407 nm. By alternating excitation at two wavelengths, i.e., about 407 and about 425 nm, the fluorescence emission spectrum excited at 407 nm can be subtracted from that excited at 425 nm to obtain a difference measurement that is proportional to the eZnPP/heme molar ratio. In some embodiments that excitation occurs at two wavelength ranges, i.e., about 405 to about 415 nm and about 420 nm to about 430 nm. In a tissue measurement, the intensities of the exciting light sources would be adjusted to give the same fluorescence emission intensities for autofluorescence. Such adjustment would depend on the light source being used by the apparatus, e.g., whether a laser or some other light source is being used. Also, the emission intensities can be normalized (e.g., scaled to the 407 nm emission spectrum). The resulting difference spectrum would be zero at the point of normalization. In the presence of eZnPP, the emission intensity on excitation at 425 nm would be greater than that at 407 nm. The difference of the two emission intensities would be virtually specific for eZnPP and would depend linearly on the concentration in the target volume.

The second excitation wavelength (around 407 nm) excites protoporphyrin IX ("ePP") fluorescence more efficiently than at 425 nm. Accordingly, information about zinc protoporphyrin (eZnPP and ePP) fluorescence can be gathered simultaneously from the difference spectrum.

Example

Figure 9:
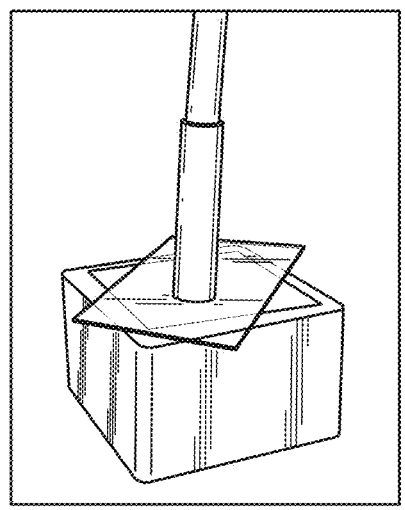
FIG. 9 is a perspective view of an apparatus and tissue phantom in accordance with an exemplary embodiment of the subject matter described herein.
Figure 10:
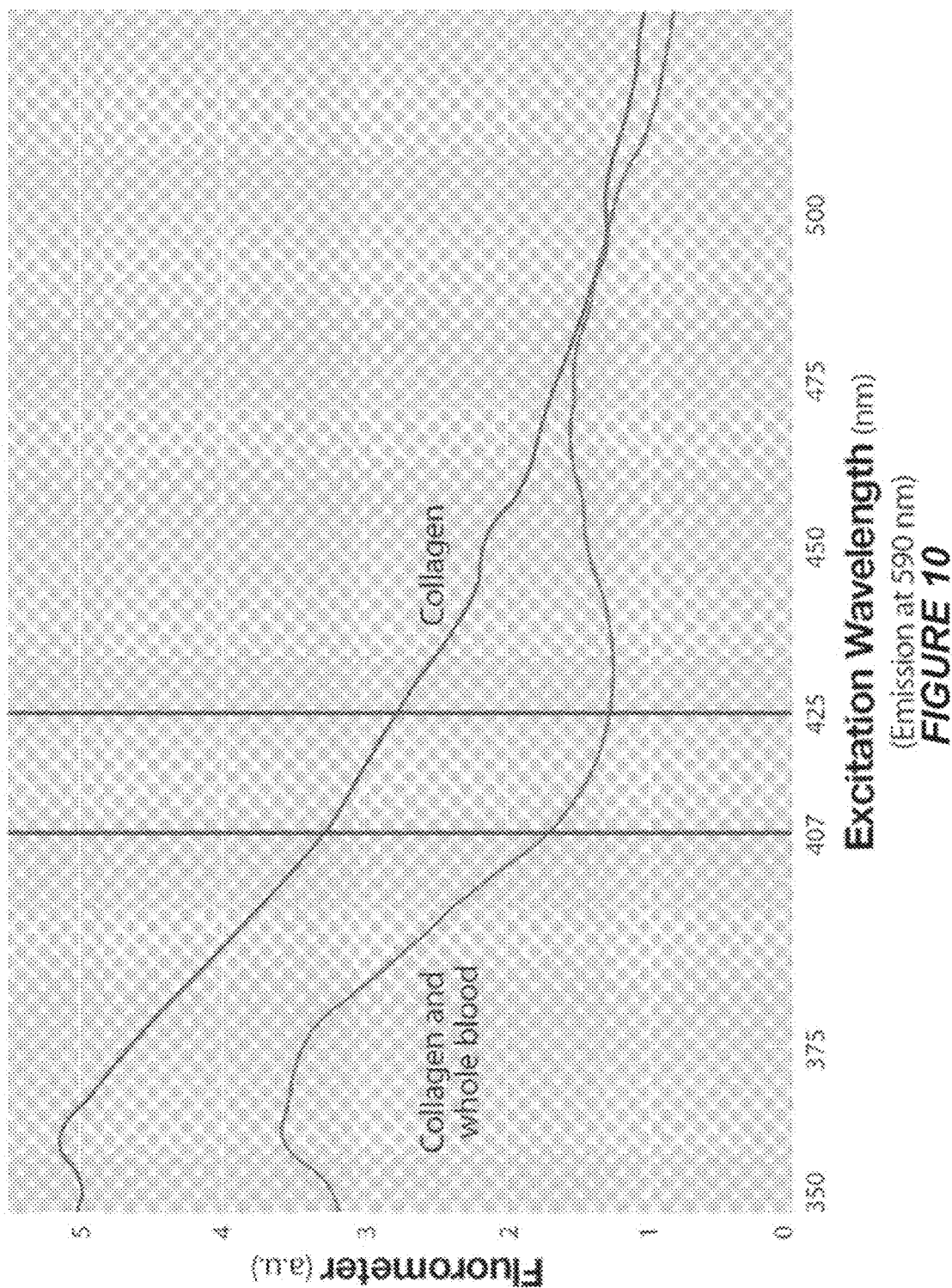
FIG. 10 illustrates the excitation spectra for collagen with and without blood.

A simple tissue phantom for oral mucosa (illustrated in FIG. 9) consists of an overlying, diffusely scattering film to model the epithelial layer and—to model the stromal layer—a solution containing dissolved elastin, lipofundin as a light-scattering agent, and also a whole blood sample at a 1% dilution (eZnPP 60 μmol/mol heme, the upper limit of normal). FIG. 10 shows the fluorescent properties of the tissue phantom, displaying the excitation spectra for collagen with and without blood. The vertical lines indicate excitation wavelengths of 407 and 425 nm.

Figure 11:
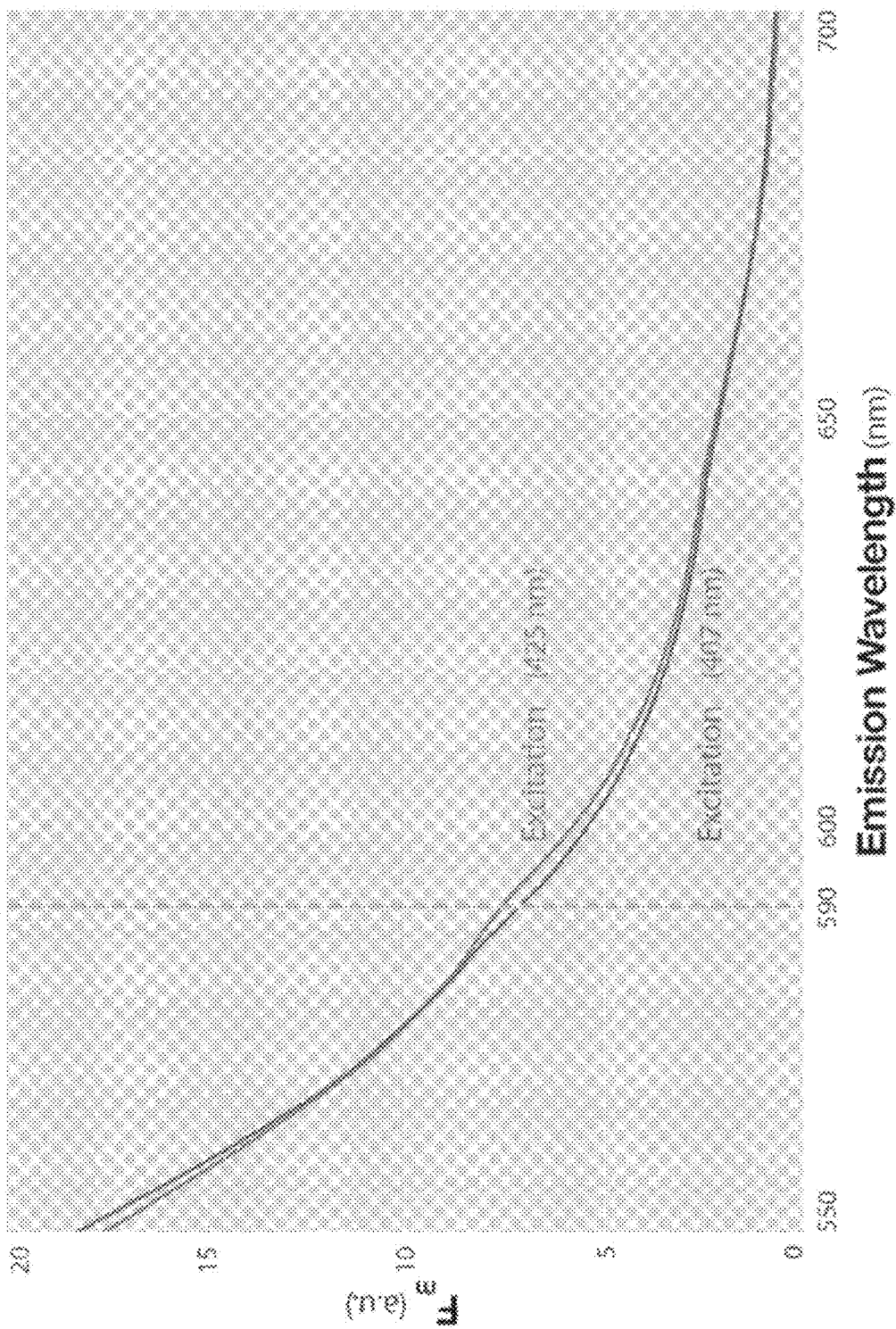
FIG. 11 illustrates the emission spectra for the simple tissue phantom of the oral mucosa.
Figure 12:
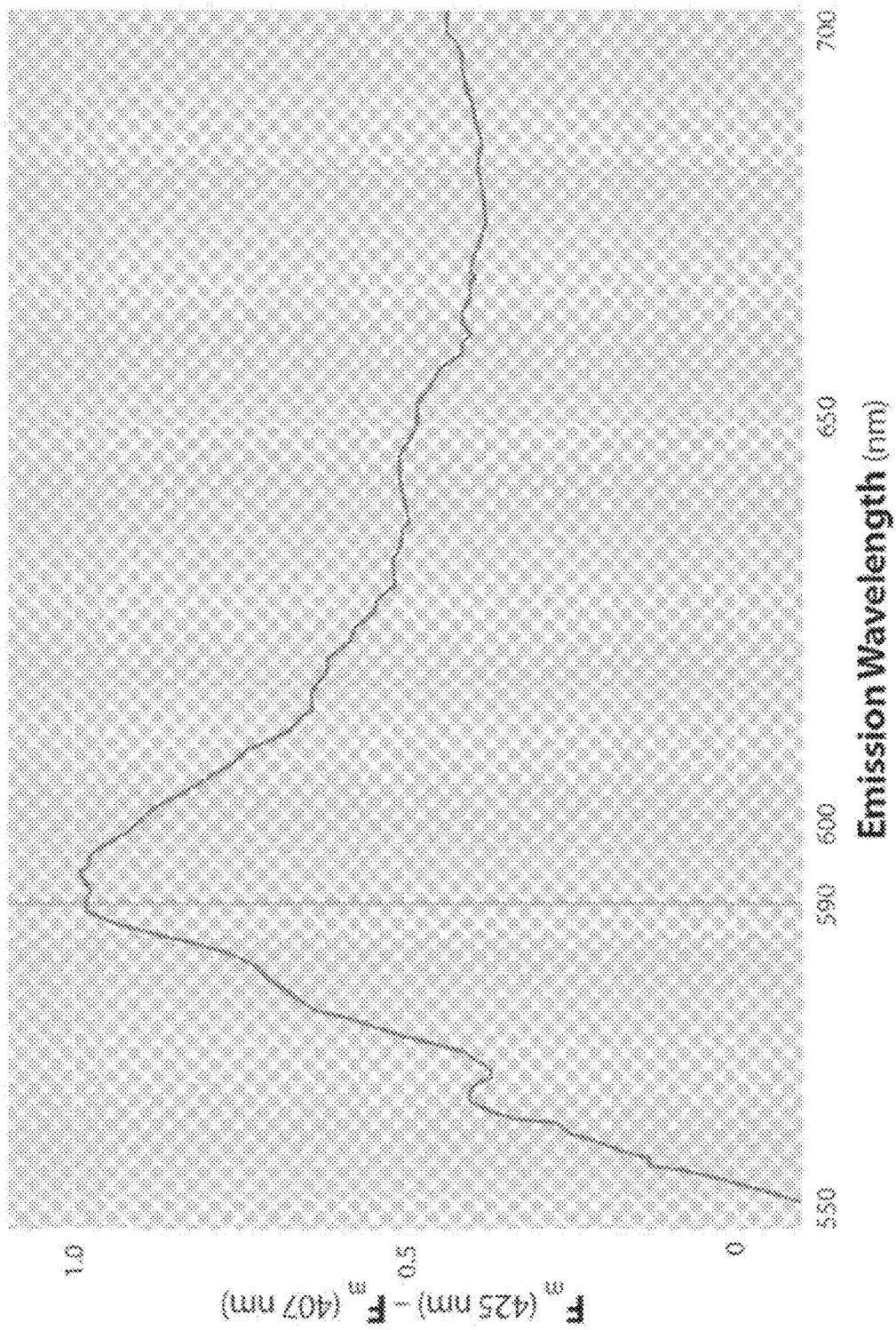
FIG. 12 illustrates the emission spectra for the difference spectrum for alternating two-wavelength fluorescence excitation.

The results are summarized in FIGS. 11 and 12. Each of the figures illustrates $F_m$ (emitted fluorescence) at the indicated excitation wavelength. Simple measurement of the emission spectra at 590 nm, in accordance with conventional techniques, would be unable to detect an emission peak for eZnPP (FIG. 11). By contrast, FIG. 12 illustrates the use of alternating two-wavelength fluorescence excitation. Accordingly, the difference spectrum $F_m(425 \text{ nm})-F_m(407 \text{ nm})$ clearly shows the characteristic emission peak at 590 nm for erythrocyte eZnPP in this tissue phantom whose concentration is at the upper limit of the normal range. In whole blood, the output is automatically quantitative for the ratio C(eZnPP)/C(Hemoglobin). Without being bound to a particular theory, it is understood that as long as the optical scattering inside the tissue doesn't vary significantly, the output will be quantitative as well. However, additional considerations include intra-/inter-patient variations and/or probe head geometry.

Figure 14:
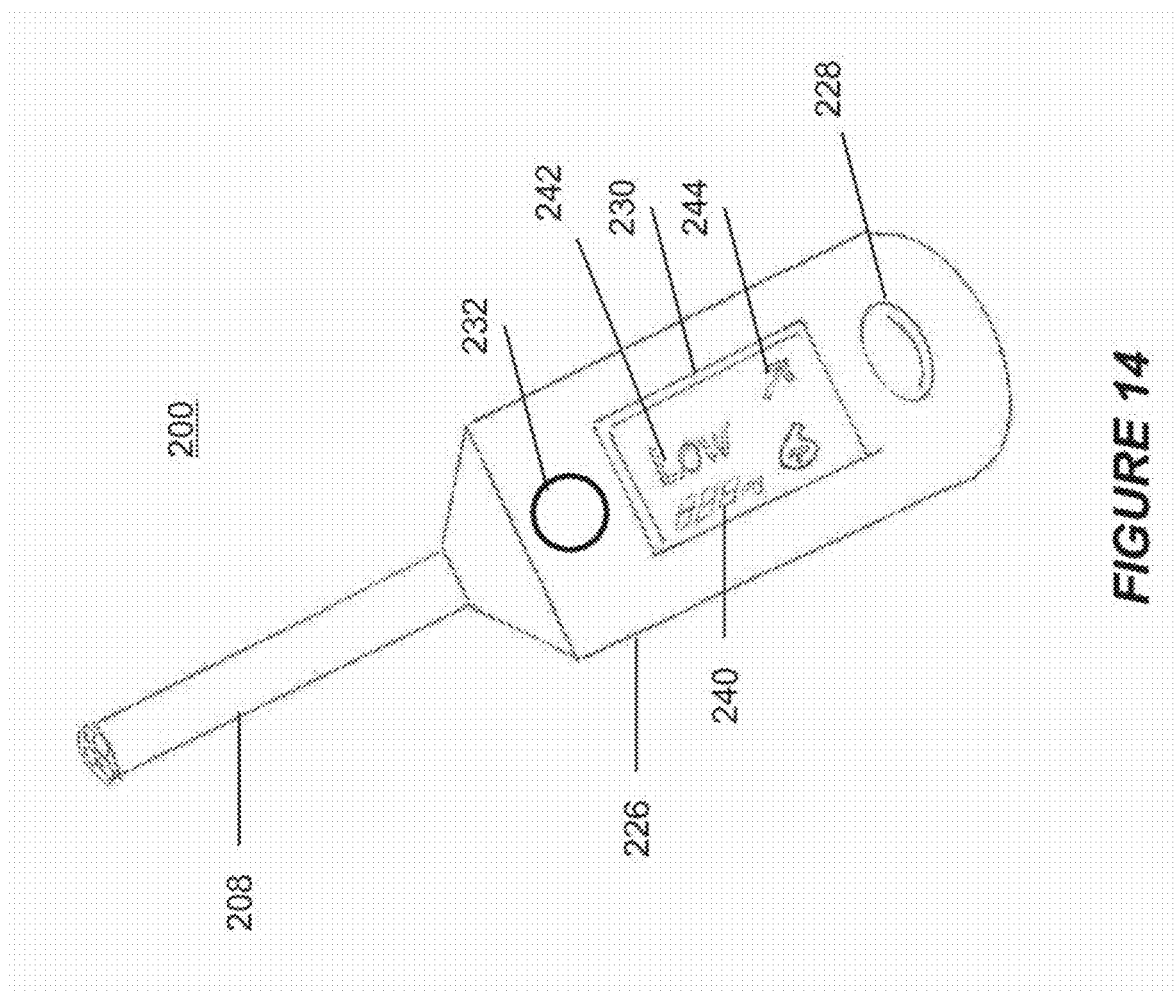
FIG. 14 is a side view of another apparatus in accordance with an exemplary embodiment of the subject matter described herein.

Fluorometer 200 is illustrated in FIG. 14 and is generally identical to fluorometer 100 discussed above, with the substantial differences noted herein. In an exemplary embodiment, the fluorometer 200 is a portable unit that includes a power supply (not shown), such as a watch-type battery or a rechargeable battery. The fluorometer 200 may include a housing 226 in which the detector, the processor and the power supply are housed. In order to provide portability, the housing 226 may have an overall length of about 2 inches to 6 inches. Fluorometer 200 includes a probe 208 used to illuminate the tissue being examined, e.g., the mucosa or a blood sample, and transmit the fluorescence to a light detector by depressing an activation switch 228.

The fluorometer 200 also includes one or more output components. In some embodiments, the output component is disposed in or on the housing. Exemplary output components include a display screen 230, a speaker 232, and/or a vibrating component (not shown). The display screen 230 may be an LCD display, an AMOLED display or the like. The output of the particular output components may be used to signal to the user that the analyte reading was successfully completed. For example, the display screen 230 may display an icon that is illuminated when successful analyte readings are obtained. The speaker 232 can provide an audible signal that the analyte reading was obtained successfully. The vibrating component similarly can provide a vibration signal to indicate successful analyte readings. Such tactile or audible outputs are particularly useful if the analyte reading is self-administered, or if the testing is performed in settings where bright sunlight or other conditions make it difficult to view the display screen.

The output component further provides an indication of the concentration of analyte in the tissue being examined. In some embodiments, the display provides a numerical indication of the analyte concentration 240. The speaker 232 may alternatively, or in addition, provide the numerical analyte concentration audibly.

For certain users of the fluorometer 200, the raw analyte information may not be meaningful. Accordingly, the fluorometer 200 may allow the user or a health care provider to enter threshold concentrations for a health range of analyte concentration. In some embodiments, the threshold concentrations may be entered at the time of manufacturing, e.g., programmed in software or hard-coded. In use, the fluorometer 200 would determine whether the detected concentration of iron is below a preselected concentration of iron. Such concentration of iron may be selected based on the circumstances, e.g., to determine whether an individual is iron-deficient or iron-replete. The display or other output device would provide an indication 242 to the user that the iron concentration was below this threshold. For example, the display would provide an indication "LOW" iron concentration or "IRON REPLETE" etc. The speaker audibly provides the same phrase. A vibrating component can be programmed to vibrate in a certain manner to indicate that a threshold has been exceeded, e.g., two consecutive vibrations for low iron concentrations.

The fluorometer 200 may also be programmed to track trends in the analyte concentration over time. In some embodiments, the fluorometer 200 includes a memory that stores multiple analyte readings, which can be tagged with a patient identification and a time stamp. When successive analyte readings are obtained for a particular patient, the fluorometer 200 can determine whether the analyte concentrations are increasing or decreasing as well as the rate of such increase or decrease. Trend indications 244 are provided by the display, e.g., upward or downward trend arrows or alphanumeric indications such as "IRON CONCENTRATION INCREASING" or "IRON CONCENTRATION DECREASING." The speaker 230 and vibrating component can likewise provide such information to the user in a similar manner as described above for the analyte concentration.

Figure 15:
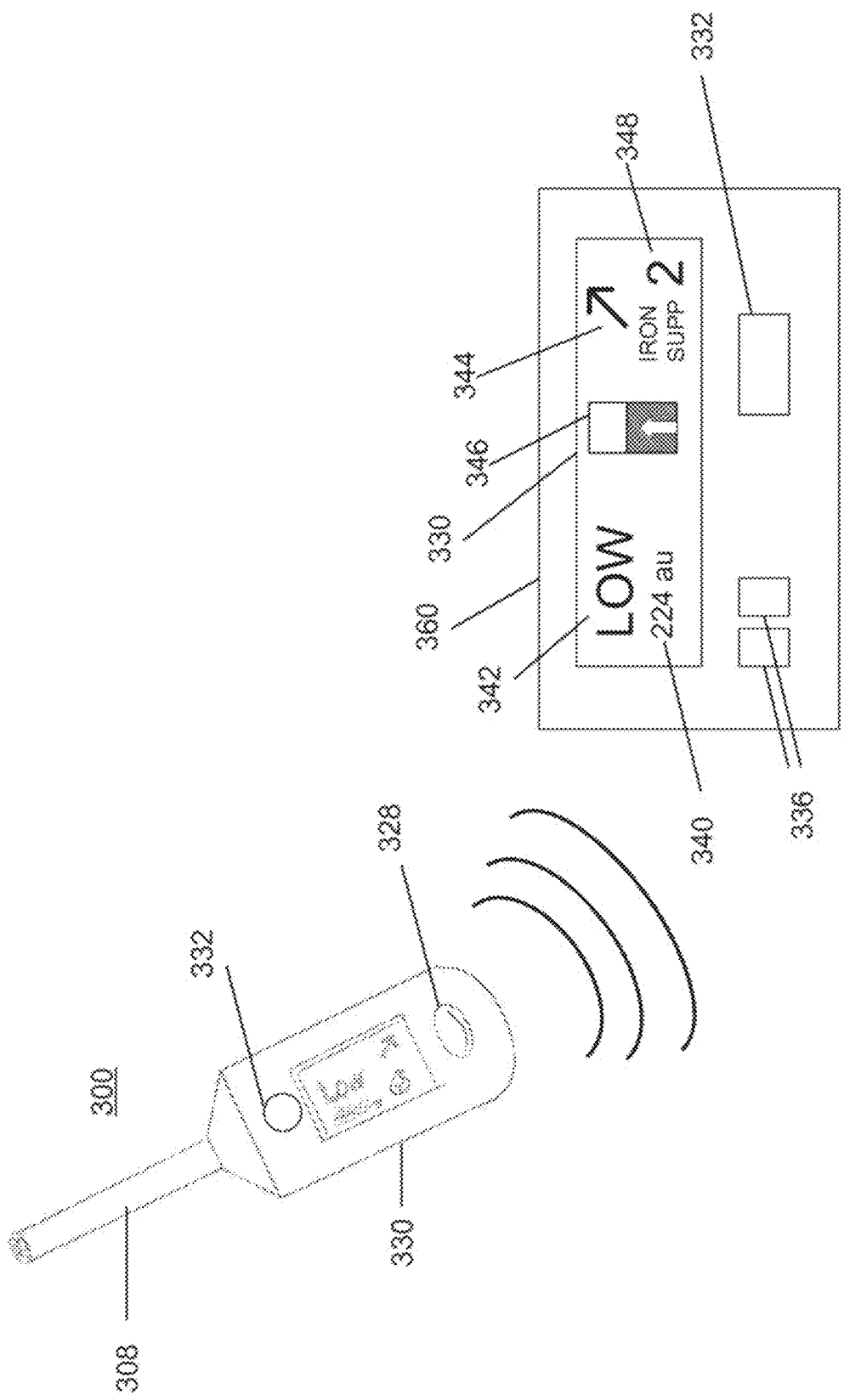
FIG. 15 is a side view of a further apparatus in accordance with an exemplary embodiment of the subject matter described herein.

Fluorometer 300 is generally identical to fluorometer 100 discussed above, with the substantial differences noted herein. In some embodiments, it is useful to provide a separate monitor unit 360 that allows the user to obtain information remotely from the patient. The fluorometer 300 includes a communications component for communicating with the monitor unit 360. The fluorometer 300 can include a wired connection to the monitor, e.g., by use of a USB connection. As illustrated in FIG. 15, the communications component may be wirelessly connected to the monitor and may include an RF transmitter, IR transmitter, Bluetooth transmitter or a WiFi transmitter for providing the detected eZnPP concentrations or other information about the patient or the fluorometer to a receiver on the monitor unit 360. Communications between the fluorometer and monitor may be achieved by providing a cellular transmitter (GSM, CDMA, etc.) or satellite transmitter on the fluorometer.

The communications component can provide signals to the monitor unit—signals that relate to the analyte concentration. Such communications may occur immediately or at a predetermined time after taking the analyte reading of the patient. In some embodiments, the fluorometer 300 may transmit the analyte reading when the analyte concentration is determined to exceed a threshold.

The monitor unit 360 includes a receiver that receives the signal from the fluorometer 300. In the case of a wireless transmission, the monitor can include an RF, IR, Bluetooth or WiFi receiver. For a wired connection, the receiver component 360 may include the electrical contacts for the wired connection. The monitor unit 360 also includes a processor, memory component, power supply and user interface. The display screen may be omitted from the fluorometer 300 in some embodiments.

A user interface is provided on the monitor unit 360, which can include a display unit 330, speaker 332, vibrating component, and input controls 336, e.g., switches, buttons, soft keys, keyboard, touch screen interface and the like. The user interface can provide an indication of the concentration of analyte in the tissue 340. The user interface provides an indication that the concentration of analyte exceeds a predetermined threshold 342, e.g., by indicating that the iron concentrations are "LOW."

The memory provided on the monitor unit 360 stores successive analyte concentrations and can provide an indication 344 that the concentration of analyte is increasing or decreasing from the previous concentration of analyte, e.g., with trend arrows.

The monitor unit 360 can be programmed, e.g., through the user interface or by factory settings, to store health goals for the patient. Such health goals include overall fitness concentrations and may include a target analyte concentration, e.g., achieving a recommended iron concentration within a desired time frame. The monitor unit 360 can evaluate whether the patient is reaching the health goal. For example, the monitor may determine that the patient's iron concentrations are increasing. The user interface may then provide an indication to the patient that the trend of iron concentrations is towards the health goal and that the user has attained 50% of the patient's health goal with a bar graph-type display 346. In some embodiments, the display screen 330 may provide an icon that changes color (e.g., from red to green) or increases in size as an indication that iron concentrations are improving. The speaker 332 can audibly provide the same information.

The user interface can provide a treatment suggestion to the patient after determining the analyte concentration and/ or comparing the analyte concentration to the patient's health goals. For example, the user interface may provide a suggestion for consuming a nutritional supplement to address the analyte concentration, e.g., consumption of iron-rich foods or supplementation, and the quantity of such supplementation 348. The user interface may suggest the patient take a pharmaceutical compound to address the particular analyte concentration.

The monitor unit 360 can be a fixed component in a clinical setting. In such case, the monitor unit can be a desktop or laptop personal computer and receive power by an AC household current. In some embodiments, the monitor unit 360 can be a portable unit. For example, the monitor can be a laptop computer, a cellular telephone, a tablet computer or the like. The monitor can be a portable dedicated handheld unit.

Figure 16:
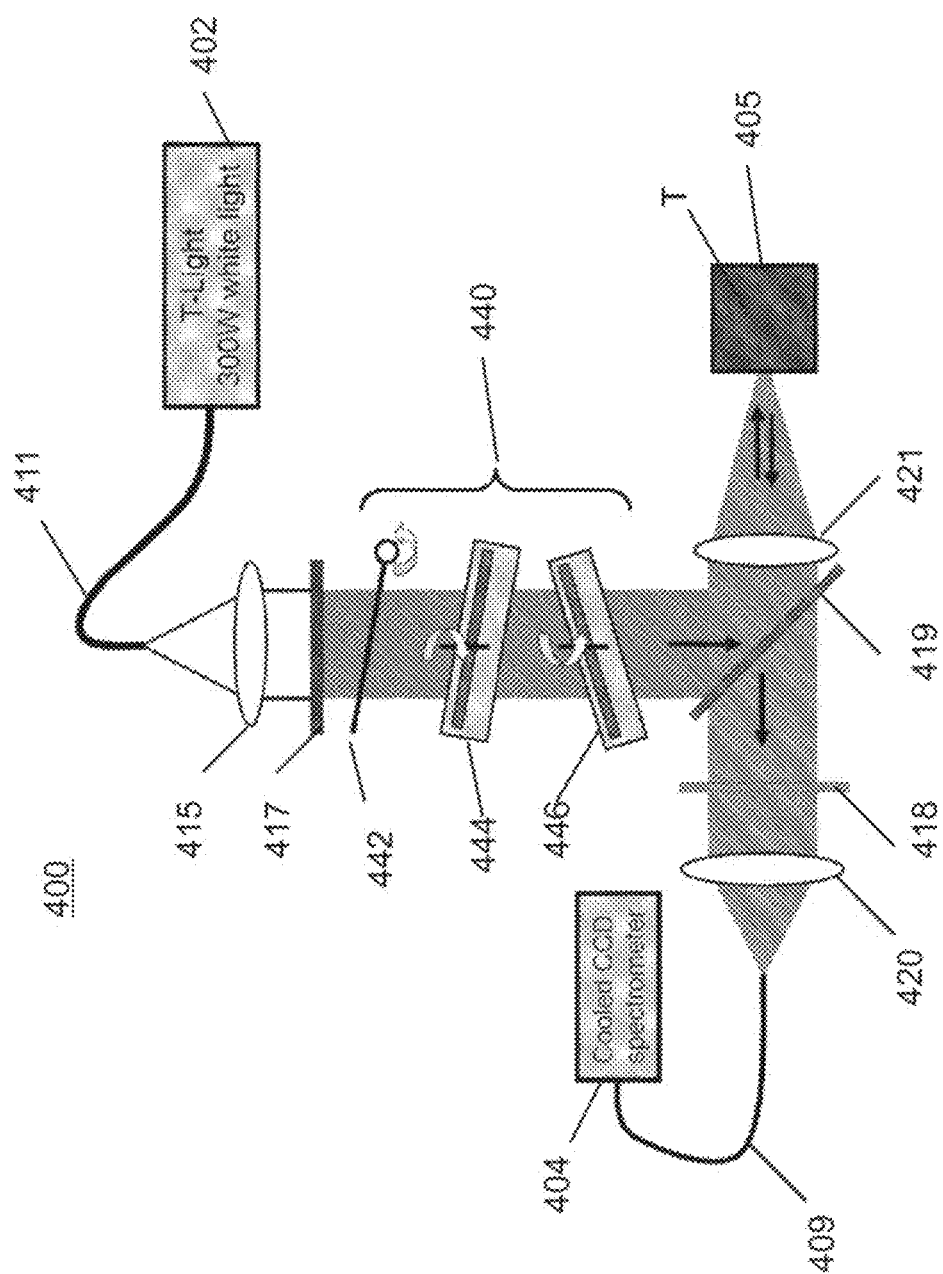
FIG. 16 is a schematic view of an apparatus in accordance with an exemplary embodiment of the subject matter described herein.
Figure 17:
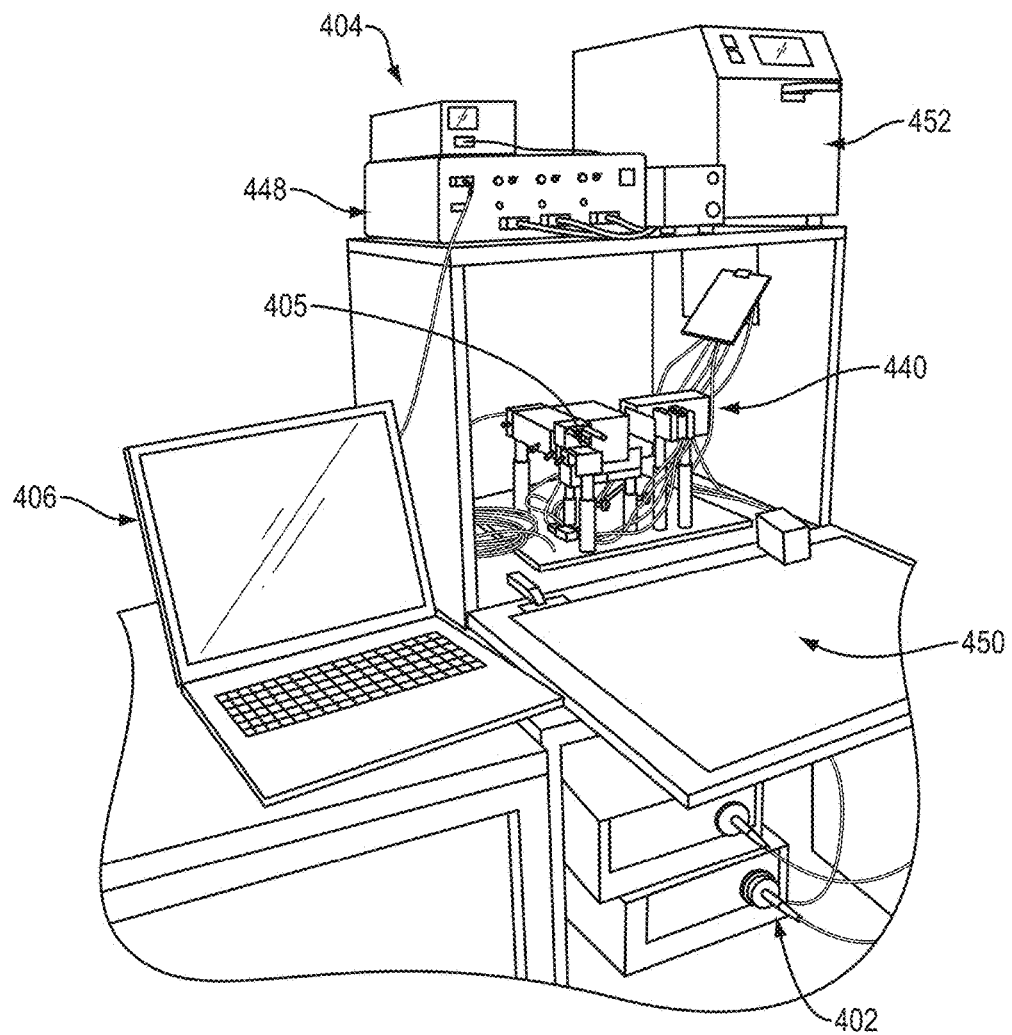
FIG. 17 is a view of an apparatus in a free-beam instrumental configuration in accordance with another exemplary embodiment of the subject matter described herein, adapted for measurement of patient blood samples or tissue.

Fluorometer 400 is illustrated in FIGS. 16 and 17, and is identical to fluorometer 100 discussed above, with the differences noted herein. In an exemplary embodiment, the fluorometer 400 includes a "free beam" configuration (e.g., a fluorometer without a fiber-optic probe). It is understood that fluorometer 400 can alternatively include a fiber-based configuration. In an exemplary embodiment, fluorometer 400 distinguishes iron deficient blood samples from iron replete blood samples. When testing is performed in vitro, the sample is tested with or without the presence of an agent to mimic light scattering in tissue. When testing is performed in vivo, the light source is applied to the intact patient tissue, e.g., the oral mucosa, as discussed hereinabove. An embodiment of the instrumentation is shown schematically in FIGS. 17 and 18.

Fluorometer 400 includes an excitation light source 402 for illuminating the tissue T of the patient and a light detector 404 for analyzing the fluorescence. In some embodiments, the light source 402 is a 500 W short-arc Xe-lamp (T-light. Karl Storz, Tuttlingen, Germany) white light source, and the light detector 404 is a cooled CCD spectrometer. The fluorometer 400 measures the concentration of eZnPP found in erythrocytes in vivo in the blood vessel of a patient, or in vitro in a blood sample T maintained in a cuvette 405. The in vitro measurements can be performed on diluted blood samples, with a concentration of 2% whole blood in phosphate buffered saline. The sample volume can be about 3000 µl, including 60 µl whole EDTA blood in a cuvette. As discussed above regarding fluorometer 100, a processor (not shown) determines the concentration of eZnPP based on the fluorescence detected by the detector 404.

The provision of light to the tissue T and transmission of fluorescence to the light detector 404 is performed by excitation light source 402, which provides radiation for tissue excitation. In an exemplary embodiment, alternating wavelengths are provided by a tunable optical filter 440. In some embodiments, the optical filter unit consists of the filter 440, as described in greater detail herein, with a tunable wavelength and a tunable bandwidth, a detection unit that can detect emission spectra from 520 to 1000 nm, and incorporates a free beam format that can be readily converted to a fiber-based configuration. In the testing configuration, light was optically filtered such that the transmitted light's central wavelength was tunable in the blue wavelength range, 395 nm to 431 nm, while preserving a spectral bandwidth h (e.g., 5 nm full width/half maximum, "FWHM"). Light in the wavelength range 500 nm-750 nm was suppressed with OD>10.

The fluorometer 400 implements the techniques described herein for measurement of a fluorescent analyte using alternating wavelengths (407 and 425 nm) for tissue excitation. Procedures were established for protoporphyrin measurements in whole blood samples using the reference HPLC method (Immundiagnostik AG) and the conventional front-face hematofluorometer 452 (Aviv; shown in FIG. 17), and the eZnPP-fluorometer 400.

With continued reference to FIG. 16, a collimating lens 415 and/or clean-up filter 417 can be provided to focus and/or direct the light to the sample T via a dichroic beam splitter 419 and lens 421. The blue light beam was focused onto the sample T, with a focus diameter of 2 mm. On the sample T, the total excitation light power was 6 mW (central wavelength 425 nm, wavelength-dependent). The fluorescence light emitted from the sample T was transmitted backwards through the beam splitter 419 and filtered by a long-pass filter 418 (e.g., G515, Schott AG, Mainz, Germany) and lens 420, limiting the usable detection range to 520 nm-750 nm. Finally, the fluorescence light was coupled into a cross-section converting fiber 409, consisting of seven 200 µm-diameter optical fibers, arranged in a circle. These fibers, linearly arranged at the other end of the fiber bundle, were coupled into a temperature regulated CCD spectrometer 404 (e.g., detection range: 340 nm-1022 nm, S2000-TR, Ocean Optics, Inc., Dunedin, Fla., USA), yielding an effective spectral resolution of 5 nm.

To optionally allow correction for wavelength- and time-dependent intensity variations, fluorescence standard measurements were performed. For example, the emission intensity of the short-arc lamp 402 is wavelength dependent, and the filtered light's intensity is also wavelength dependent. Also, the total power of the lamp 402 may change during usage. The fluorescence standard includes a 1 mm thick piece of commercially available solid polymethyl methacrylate containing Rhodamin B (1BF/RB, Starna GmbH, Pfungstadt, Germany), fixed at the wall of the cuvette 405.

After accounting for background tissue fluorescence, scatter, path length, geometric and other factors, the processor correlates the intensity of the fluorescence to the eZnPP/heme ratio and provides the result in an output device, such as a display screen, speaker or vibrating unit. An optional communications component is provided in certain embodiments, as will be described in greater detail hereinbelow. An optional power supply, such as a battery, can be included in the fluorometer, particularly if it is a portable device. In some embodiments, the fluorometer 400 can be directly connected to the electrical power supply of the home or institution.

Tunable Filter

Figure 18:
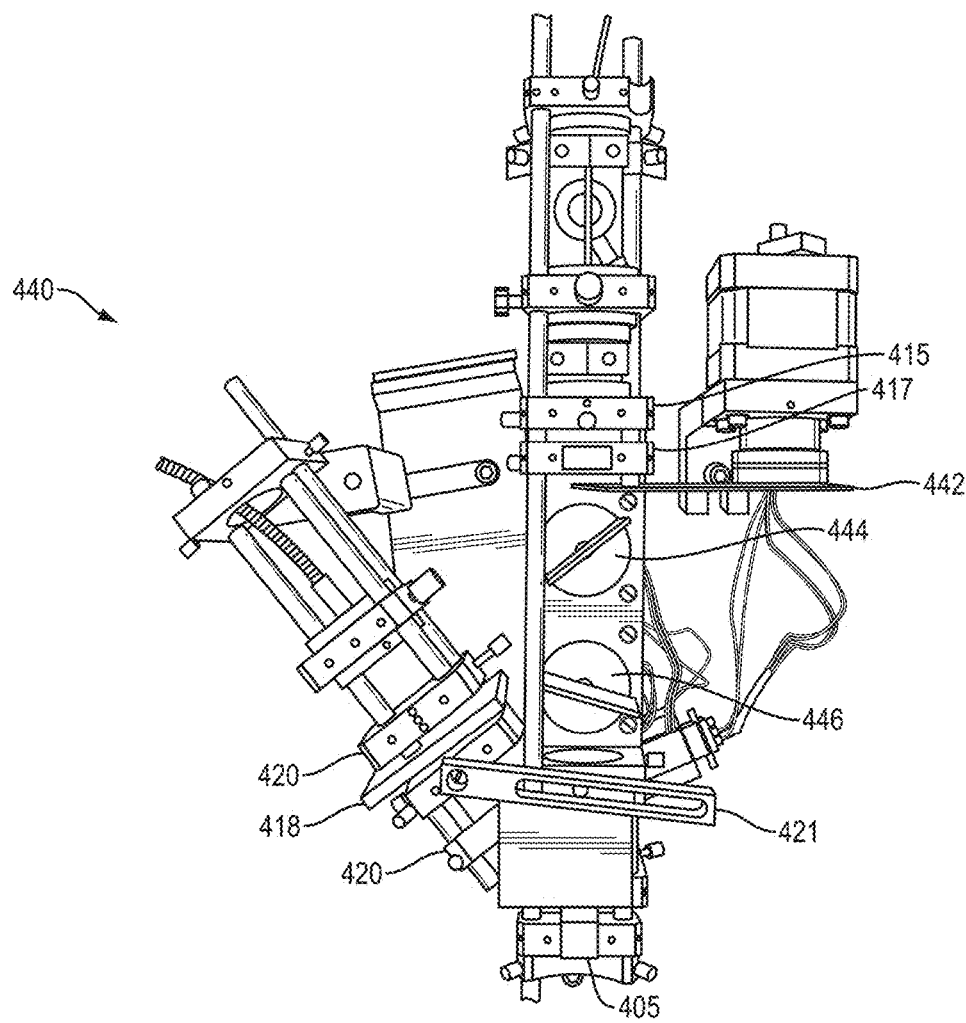
FIG. 18 is a view of a portion of an apparatus in accordance with another exemplary embodiment of the subject matter described herein.

The instrumentation of tunable optical filter 440 is illustrated in FIGS. 16 and 18. The filter unit 440 allows the simultaneous selection of both the central filtered wavelength and the spectral bandwidth, for use in applications requiring detection of light or illumination by light at a small spectral bandwidth. The tunable optical filter unit 440 provides improved light transmission efficiency and makes possible spectral filtering of images and fiber bundles without a scanning device. Although the filter unit 440 is described herein in connection with fluorescence spectroscopy, the filter unit 440 can find application in fluorescence microscopy, fluorescent imaging, and in advanced microscopy applications such as fluorescence-lifetime imaging microscopy. For illumination, the filter 440 can be used with filtered incoherent light sources to achieve strong illumination intensities at small spectral bandwidths, such as illumination for fluorescence microscopy, fluorescence spectroscopy, and more generally, in applications in which a tunable laser is not practical, e.g., due to cost.

As illustrated in FIG. 18, filter unit 440 includes two tunable bandpass optical filters 444 and 446, e.g., Semrock Versachrome® filters capable of independent rotation for selecting an angle of incidence with a beam of light passing through the filter unit 440. After acquiring the fluorescence emission spectra for the excitation wavelengths, shutter 442 was closed to prevent further illumination of the sample T. A dark spectrum can be recorded with the same settings. Step motor controller 448 is provided to allow independent rotation of the two step motors carrying the optical filters at a high rotation speed with sub-degree precision.

Figure 19:
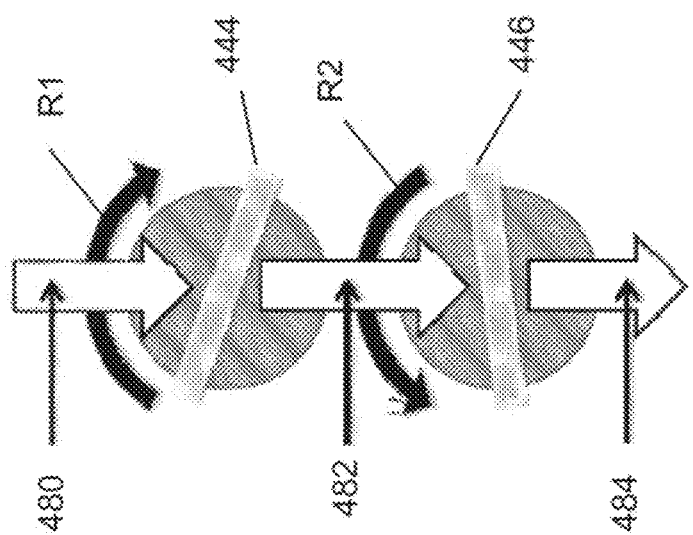
FIG. 19 is a schematic view of the apparatus of FIG. 18 in accordance with an exemplary embodiment of the subject matter described herein.
Figure 20:
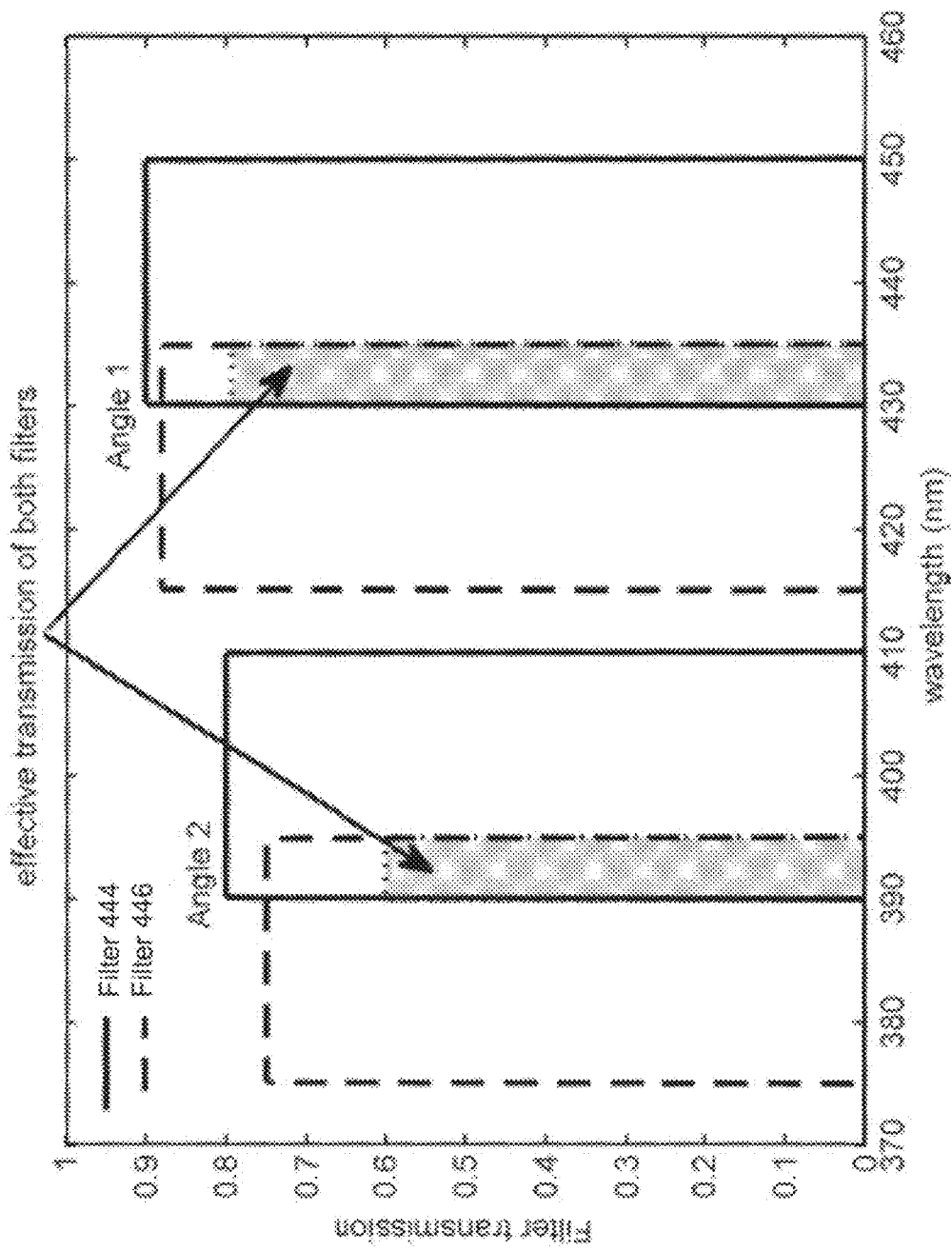
FIG. 20 illustrates the transmission of light through the apparatus of FIG. 18 in accordance with an exemplary embodiment of the subject matter described herein.

The components, design and function of the filter unit 440 are shown schematically in FIGS. 19-24. In FIG. 19, a beam of light passing through filter unit 440 is designated as beam portions 480, 482, and 484. Beam portion 480, a collimated beam of unfiltered light typically having a large spectral width, is transmitted through optical filter 444, e.g., a Versachrome filter capable of rotation as indicated in the angular direction of arrow R1 (as well as in the opposite angular direction indicated by arrow R1). The filtered light beam 482, filtered by filter 444, has a fixed spectral bandwidth, and the central wavelength can be selected by the angle of filter 444 with respect to the incidence of beam 480 on filter 444. The light beam 482 is transmitted through filter 446, e.g., a Versachrome filter capable of rotation as indicated in the angular direction of arrow R2 (as well as in the opposite angular direction indicated by arrow R2), with the resulting light beam 484. The results are illustrated in FIG. 20, showing the proportion of effective transmission through the two filters 444 and 446. The solid lines represent transmission through the first filter 444 for two different angles defined with respect to the direction of the light beam. Typically, angle 2 is greater than angle 1. The dotted lines represent the transmission through the second filter 446 for two different angles. The total transmission characteristics of the filter unit 440 are the product of both transmission curves (filter 444 and filter 446), solid and dotted, shown as a shaded area under the overlap of the curves in FIG. 20. In the exemplary embodiment, filter 444 and filter 446 provide about 60% transmission of light. If two similar filters are used for filters 444 and 446, the angles of the two filters have to be chosen independently because the angular dependency of the filter transmission is non-linear. Example: Angle 1: a(Filter 444)=20°, a(Filter 446)=0° resulting in a 5 nm spectral bandwidth; Angle 2: a(Filter 444)=40°, a(Filter 446)=35° also resulting in a 5 nm spectral bandwidth at a lower central wavelength.

Figure 21:
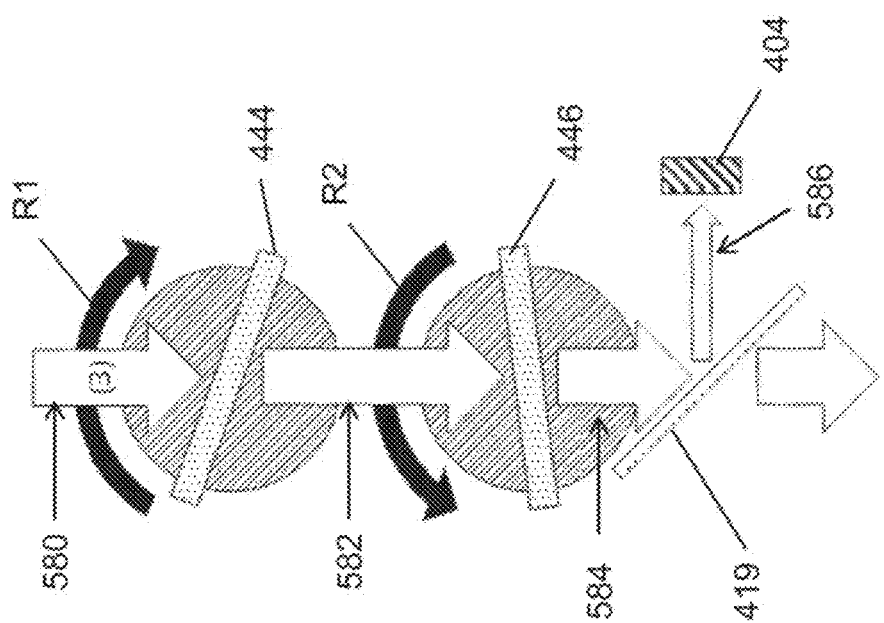
FIG. 21 is a schematic view of a portion of an apparatus in accordance with an exemplary embodiment of the subject matter described herein.

As shown in FIG. 21, after transmission of the light through filters 444 and 446, a beam splitter 419 can be added to the filter unit 440 for monitoring a part of the filtered light, e.g., light beam 586. This part of the light can be detected, e.g., by a spectrometer 404 or power meter to monitor the spectral bandwidth, the power or both.

Figure 24:
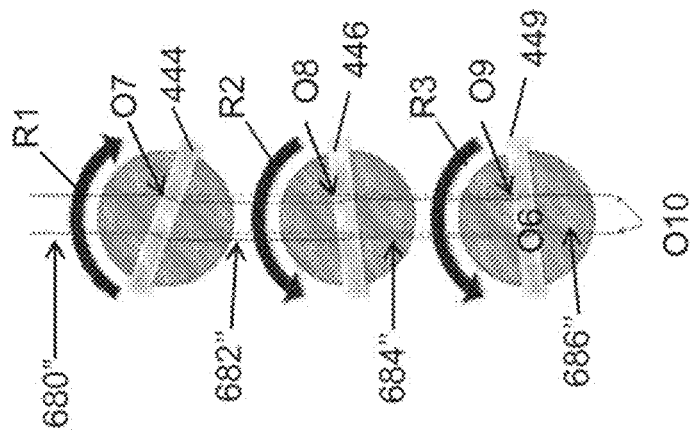
FIG. 24 is a schematic view of a portion of an apparatus in accordance with an exemplary embodiment of the subject matter described herein.
Figure 23:
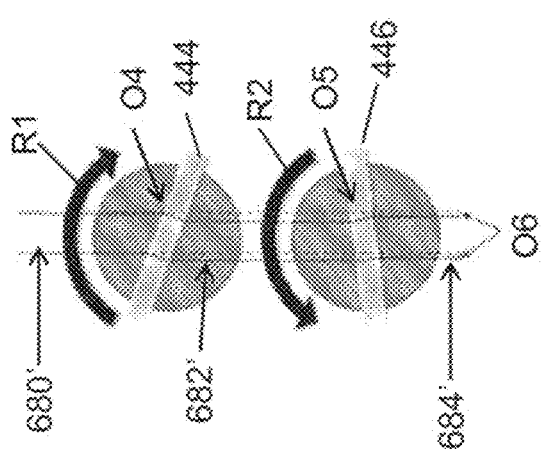
FIGS. 22-23 are schematic views of a portion of an apparatus in accordance with an exemplary embodiment of the subject matter described herein.
Figure 22:
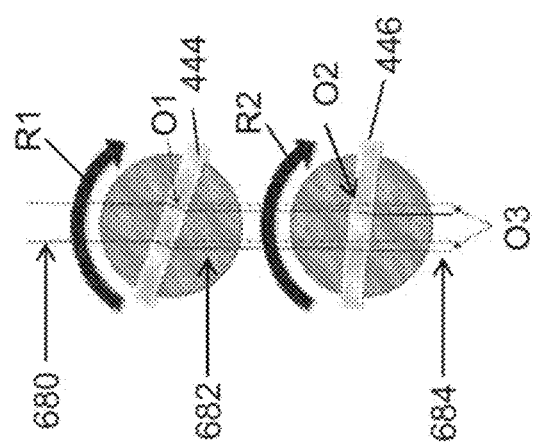

As shown in FIGS. 22-25, during non-perpendicular transmission of a light beam through a filter, a parallel offset of the light beam occurs. If the filters are arranged as shown in FIG. 22, the offset provided by filters 444 and 446 accumulates to a large net offset. As illustrated in FIG. 22, the offset O1 of light beam 682 with respect to light beam 680, and the offset O2 of light beam 684 with respect to light bean 682 results in a total offset O3 with respect to light beam 680. (A dashed line is used to represent the hypothetical trajectory of light beam 680 in the absence of filters 444 and 446.) If the filters are rotated counter-wise, i.e., in opposite directions, as shown in FIG. 23, the offset O6 of light beam 684' with respect to light beam 680' (the cumulative offset of offset O4 and offset O5) is significantly reduced from offset O3 but not eliminated because the angles of both filters 444 and 446 are different. In some embodiments, as illustrated in FIG. 24, a third optical element 449, e.g., a planar piece of glass that provides 100% transmission and refractive index n>1, can be inserted, in which case the offset O10 between light beam 680" and light beam 686" is eliminated (i.e., O10=0).

During in vitro testing, blood samples and tissue phantoms may contain a light-scattering agent to mimic the optical properties of tissue such as the oral mucosa. Latex microspheres having a diameter of about 0.5 μm were found to have little autofluorescence and remained suspended during the time required for testing, and thus are a suitable, exemplary light-scattering agent.

Figure 25:
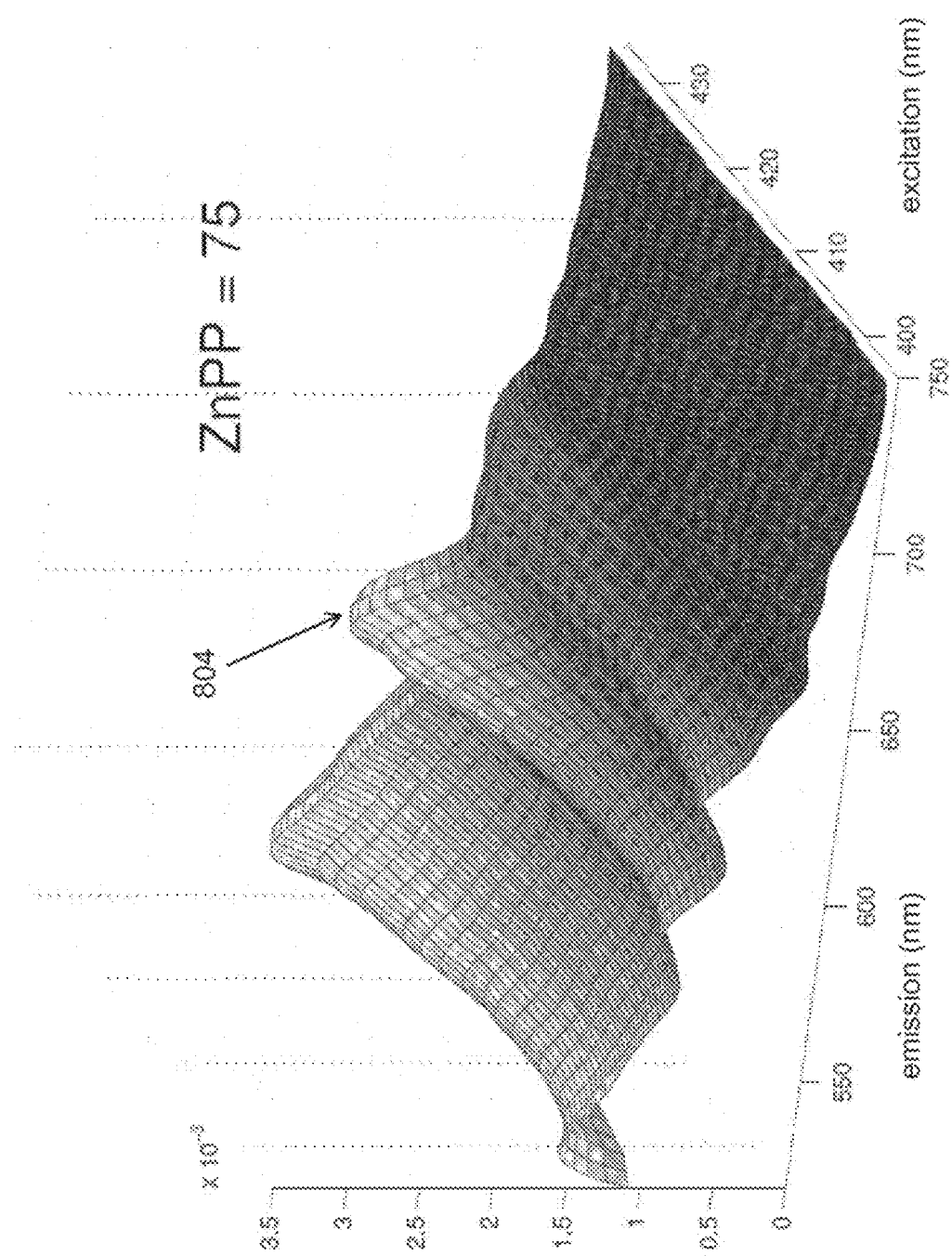
FIGS. 25-30 illustrate the excitation and emissions spectra of tissue measured in accordance with an exemplary embodiment of the subject matter described herein.
Figure 26:
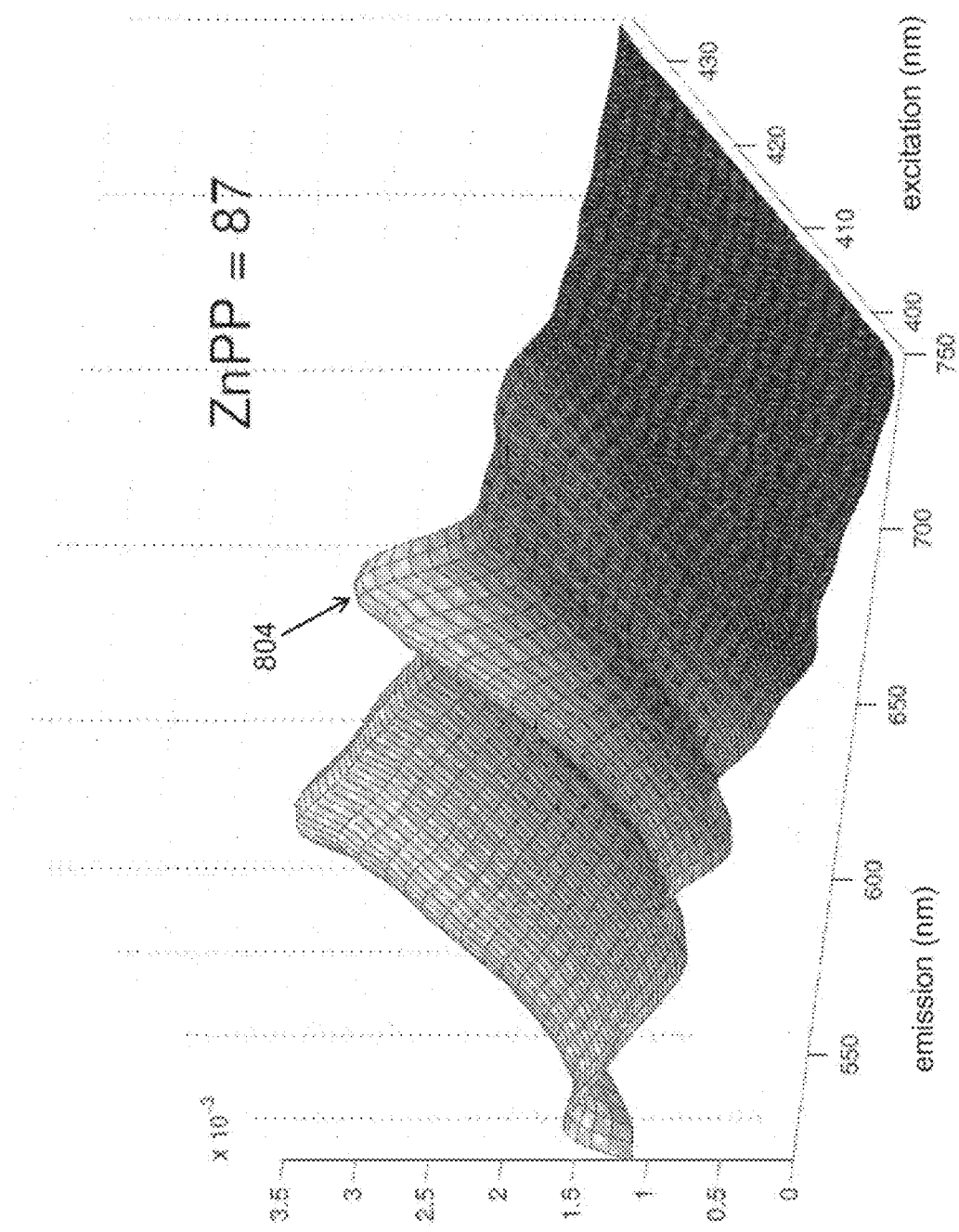
Figure 27:
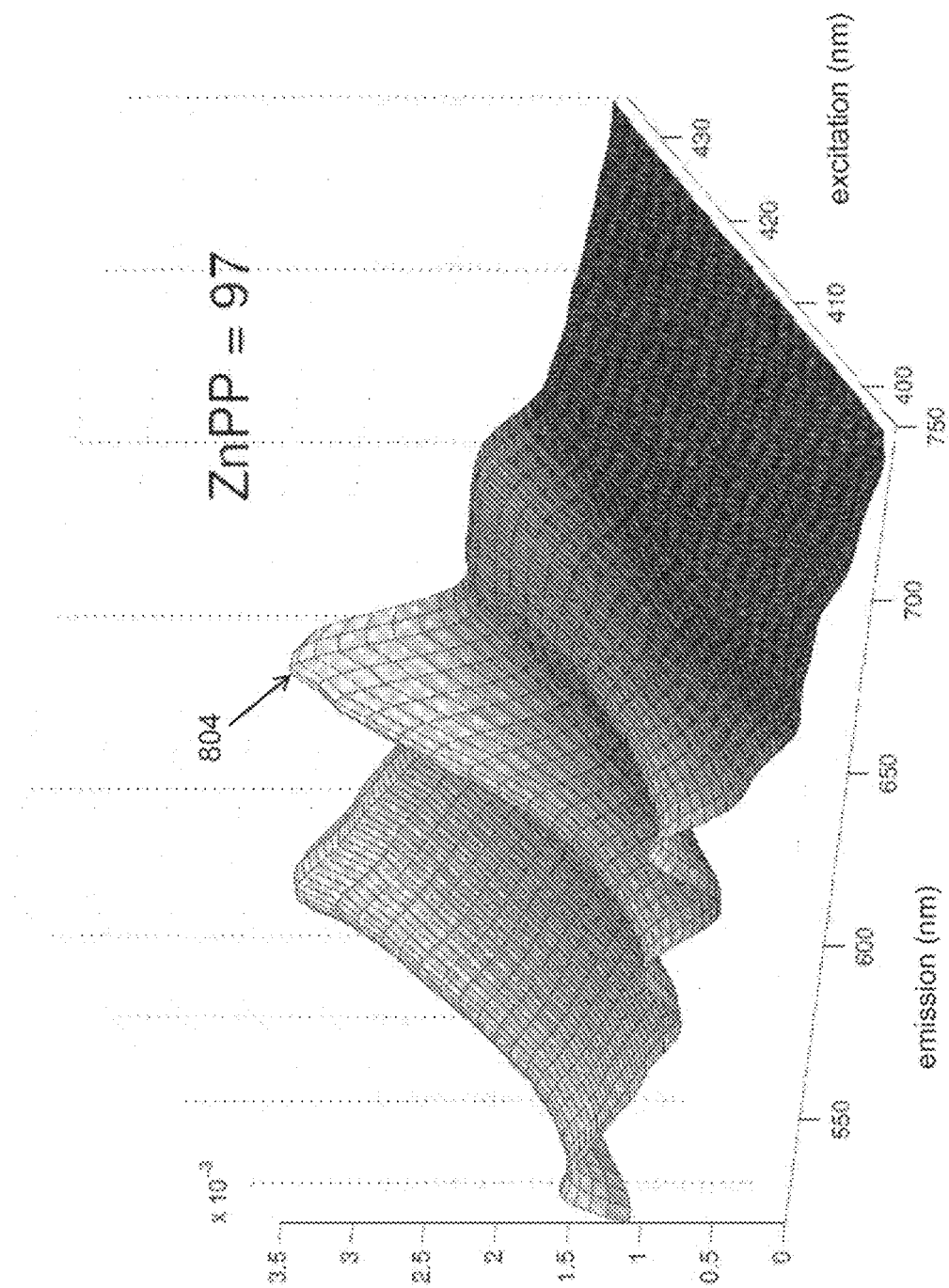
Figure 28:
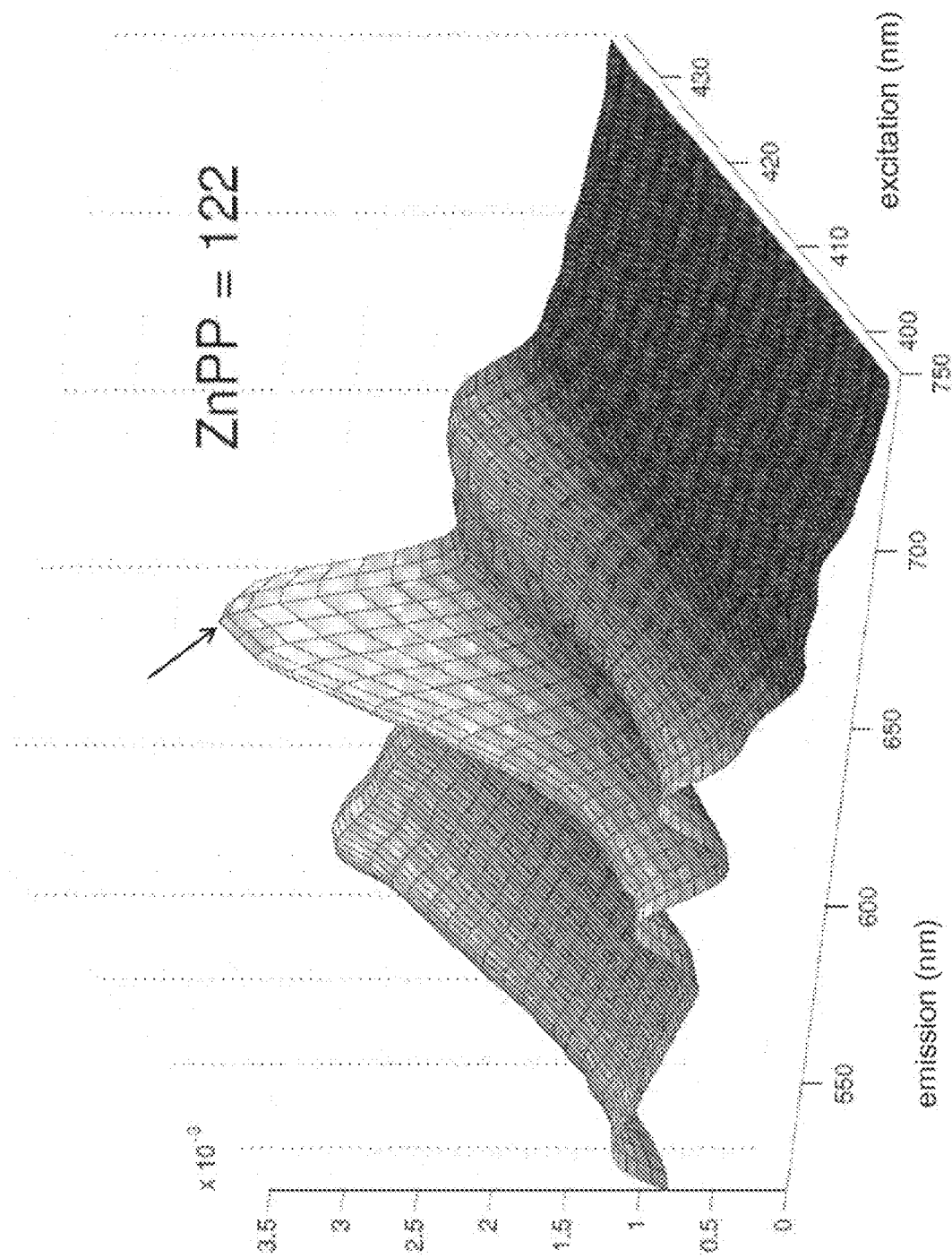
Figure 29:
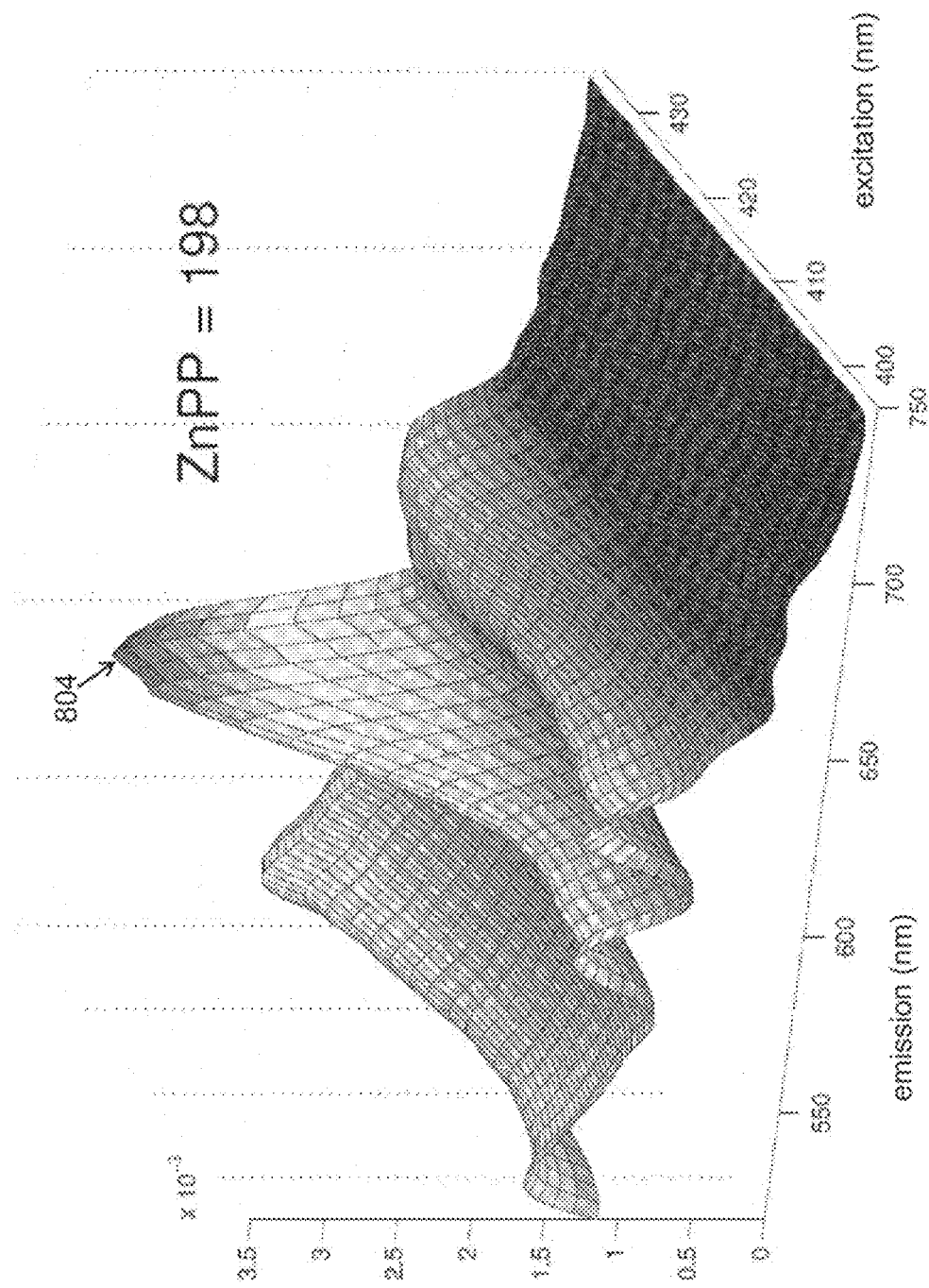
Figure 30:
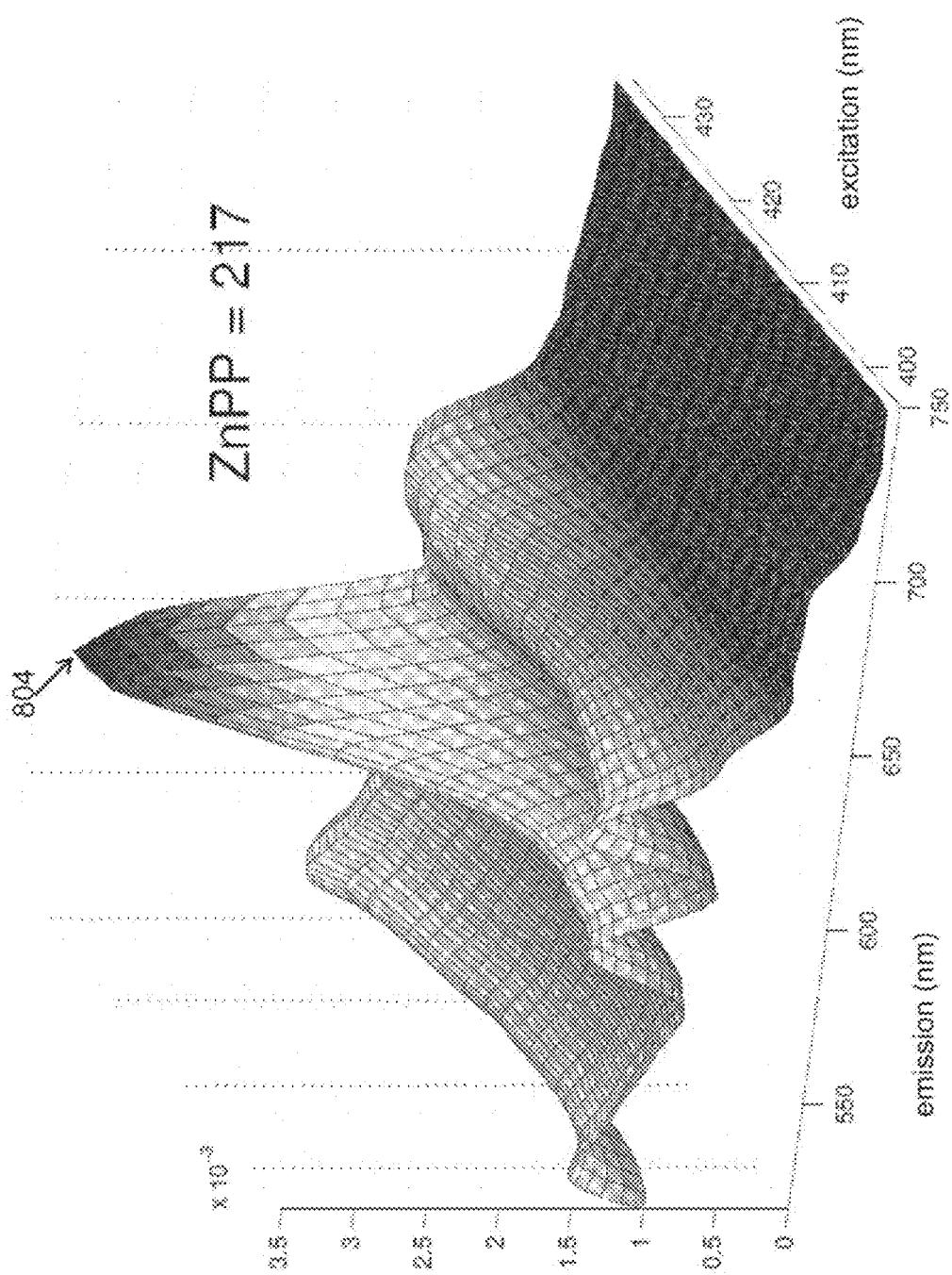
Figure 31:
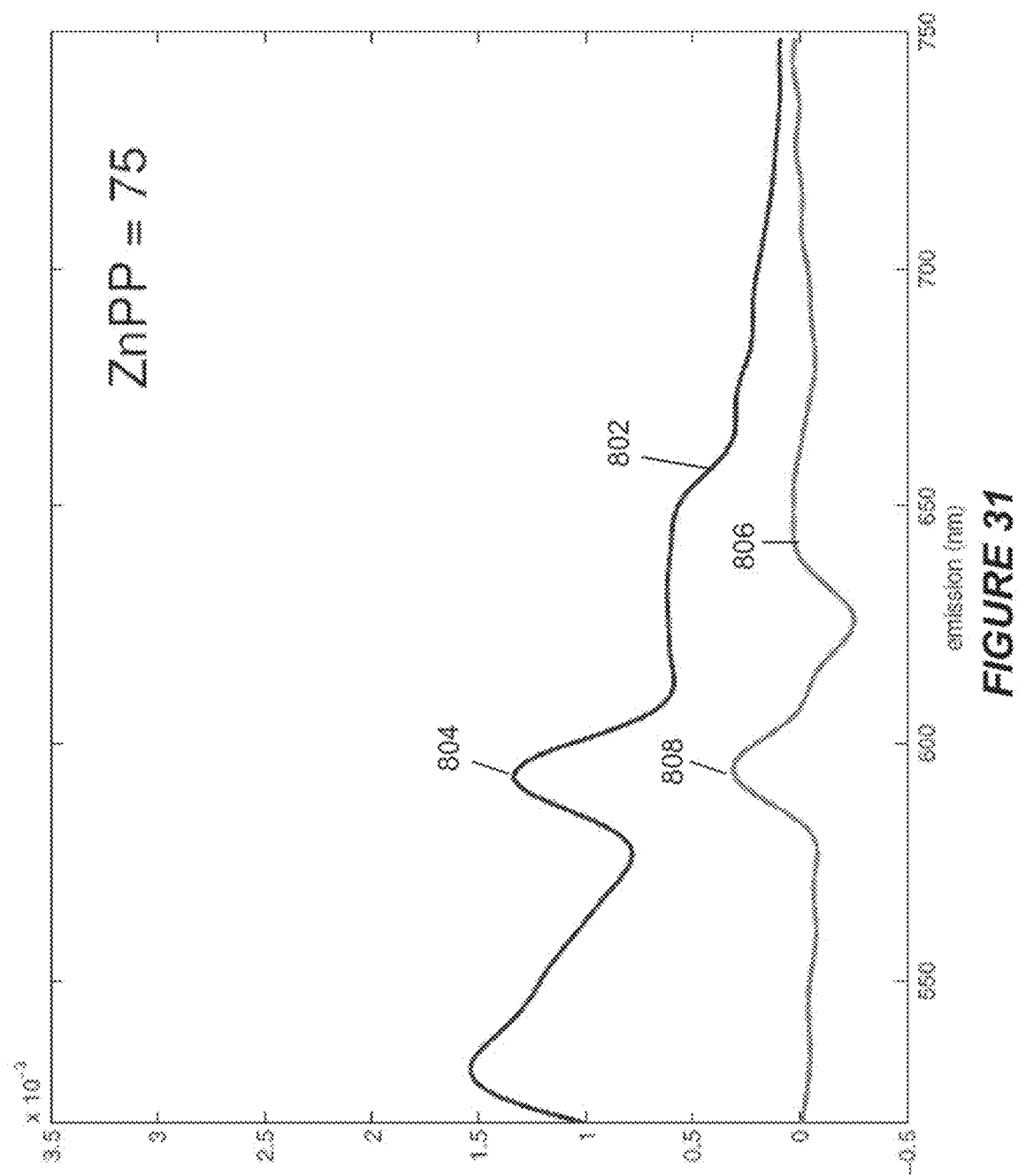
FIGS. 31-36 illustrate a comparison of conventional techniques with the results obtained in accordance with an exemplary embodiment of the subject matter described herein.
Figure 32:
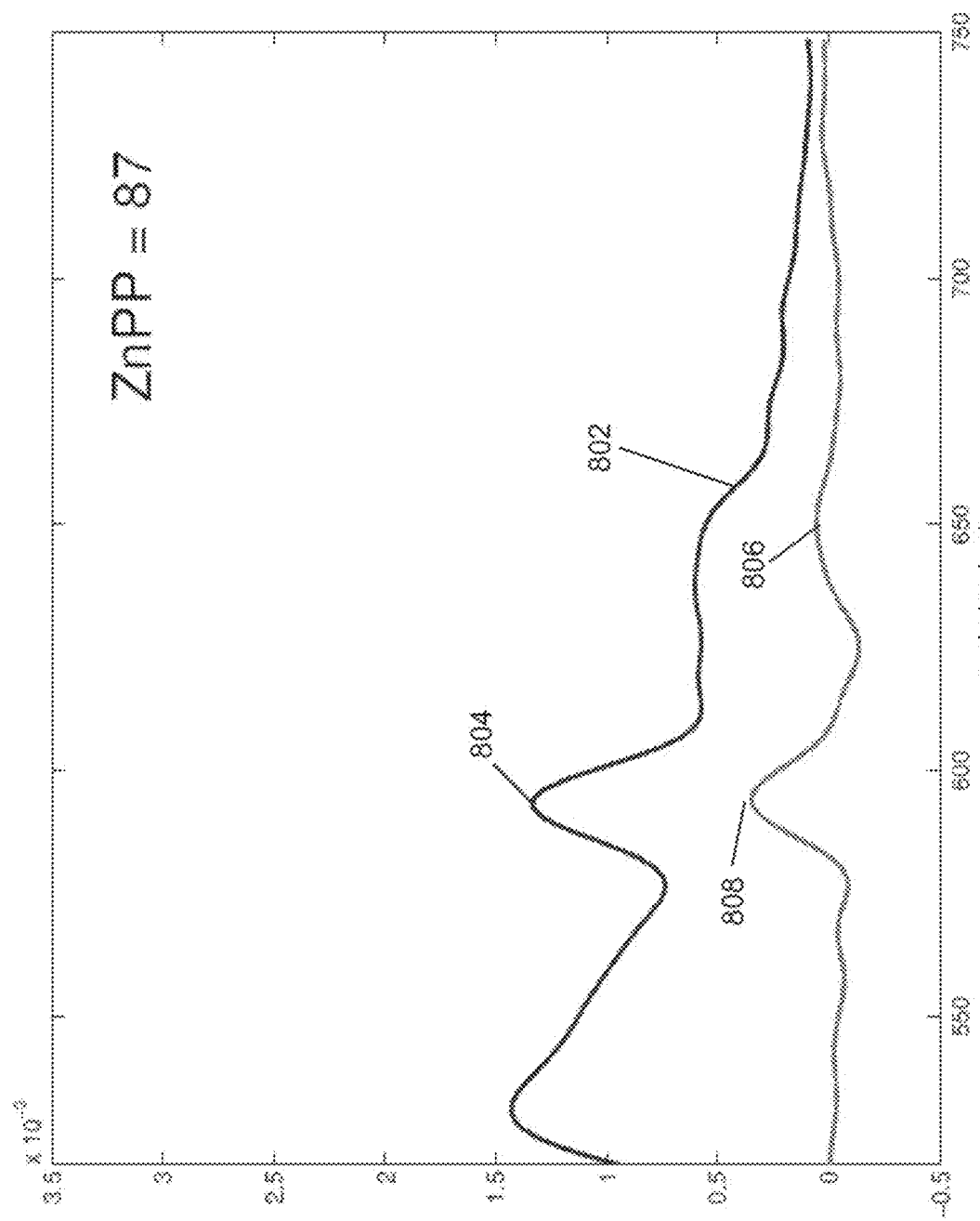
Figure 33:
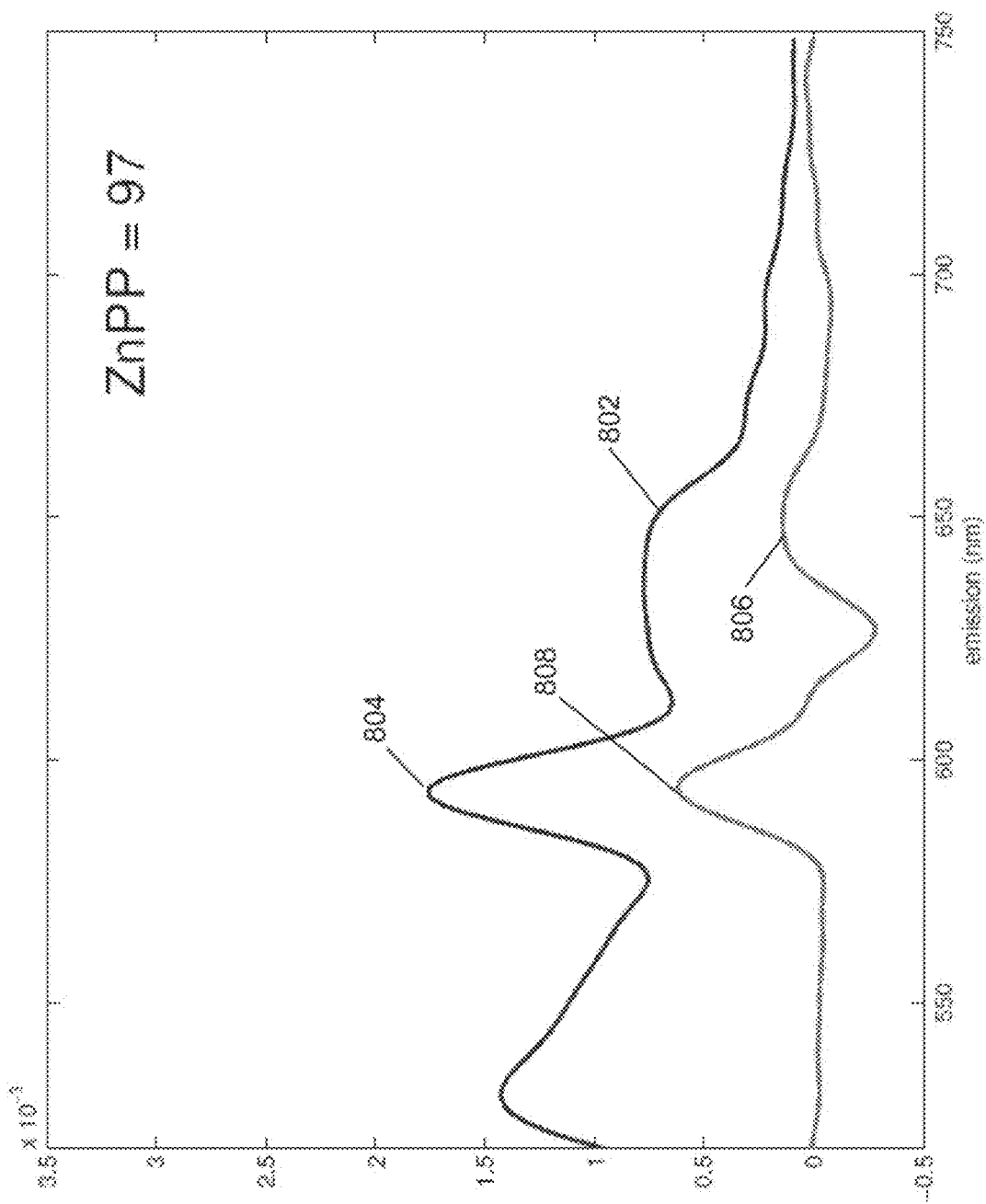
Figure 34:
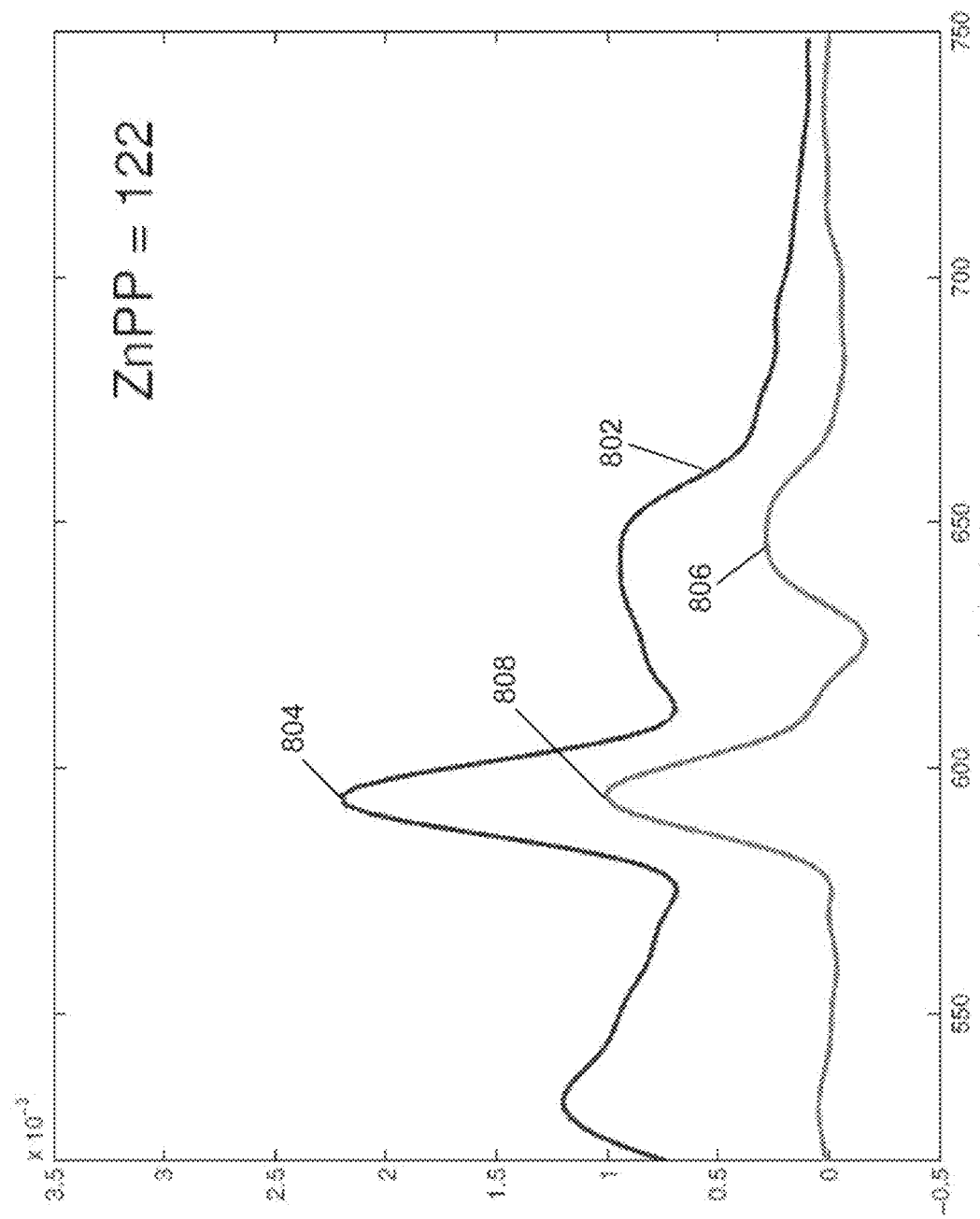
Figure 35:
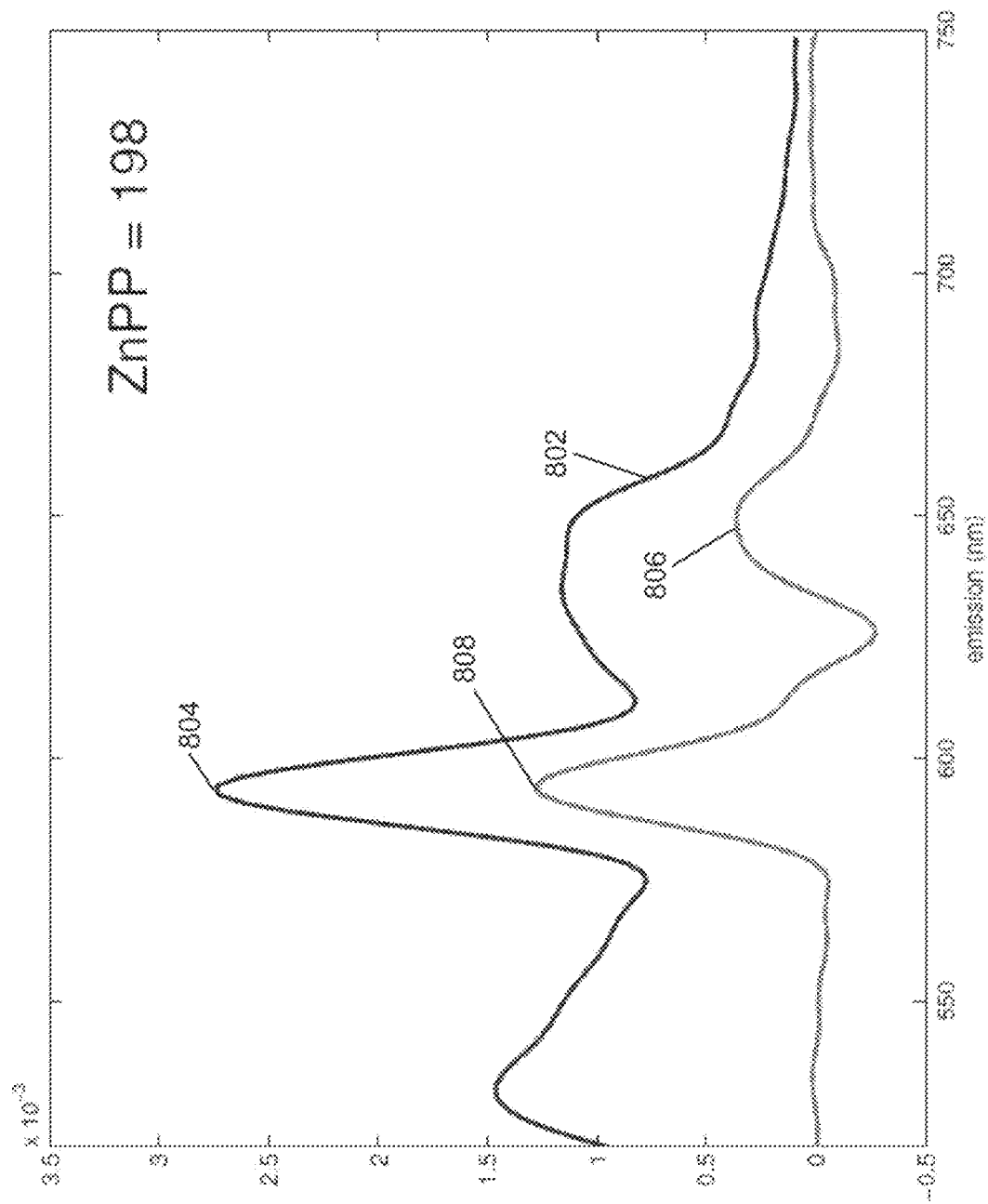
Figure 36:
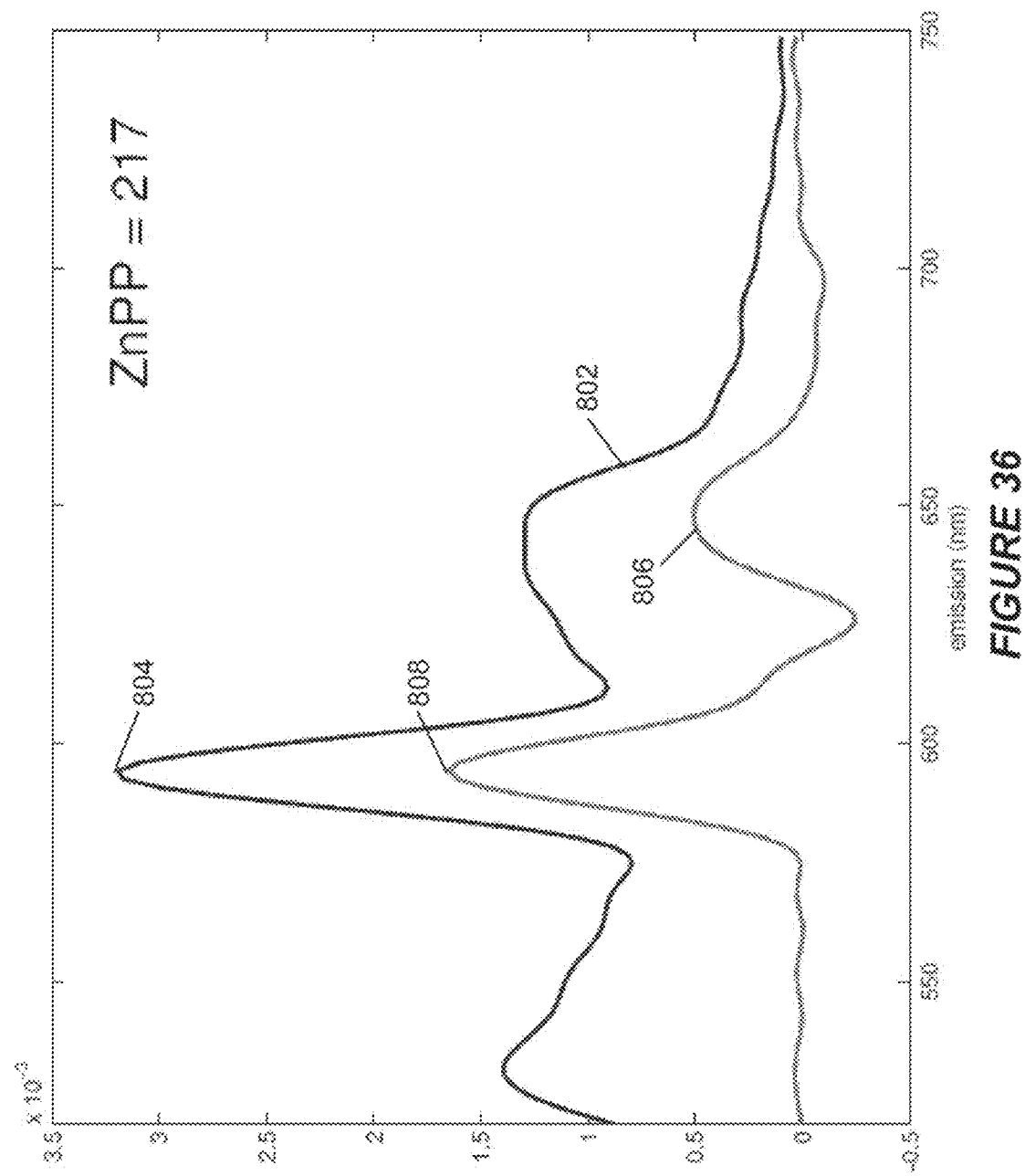

FIGS. 25-30 illustrate the excitation and emission spectra of tissue. The z-axis represents arbitrary units (a.u.). A single excitation central wavelength, with a bandwidth of 5 nm full width at half maximum (FWHM), was used to obtain the associated emission spectra. To determine that 407 and 425 nm are the optimal alternating wavelengths for measurements of blood samples, excitation-emission matrices were obtained in blood samples (2% in saline) with eZnPP concentrations in the reference ("normal") range of 30 to 80 mmol/mol heme and iron deficient range (>80 mmol/mol heme), as determined by conventional front-face Aviv hematofluorometer. (In the Figures, "ZnPP" refers to the erythrocyte zinc protoporphyrin concentration. In FIG. 25, for example, "ZnPP=198" means erythrocyte zinc protoporphyrin concentration of 198 μmol ZnPP/mol heme.) Typical matrices are shown in FIGS. 25-30. The eZnPP peak 804 is illustrated in FIGS. 25-30 at excitation of 425 nm. For the determination of eZnPP levels in blood, 407 nm and 425 nm provide the optimal performance as the alternating wavelength pair.

As shown in FIGS. 31-36, the alternating (407 nm-425 nm) wavelength method significantly reduces or eliminates the background whole blood autofluorescence that produces an elevated baseline with conventional single wavelength (425 nm) studies. The y-axis represents arbitrary units (a.u.). The conventional single wavelength measurement (425 nm) is indicated by line 802 (upper line) and its associated eZnPP peak 804. (FIG. 31 corresponds to the data illustrated in FIG. 25 for an excitation wavelength of 425 nm and eZnPP=75.) The alternating (407 nm-425 nm) wavelength method in accordance with the embodiments described herein is indicated by line 806 with an associated eZnPP peak 808.

Example

A study was performed using 35 anonymous patient whole blood samples from the Institut für Laboratoriumsmedizin, Klinikum der Universität München, which were analyzed prospectively for erythrocyte zinc protoporphyrin ("eZnPP") concentration by the reference HPLC method (Immundiagnostik AG), by the Aviv hematofluorometer, and by the ZnPP-fluorometer 400 in a free beam configuration as described herein.

The reference ("normal") range of eZnPP concentrations was 30 to 80 μmol/mol heme. The iron deficient range of eZnPP concentrations was >80 nmol/mol heme. The study included eZnPP-fluorometer measurements of the blood samples (i) without a light scattering agent, with a blood volume fraction of 0.02, (ii) with the smaller (0.5 nm) latex microspheres as a scattering agent to provide scattering coefficients over a physiologic range (reduced scattering coefficient about $\mu_s'$=1 to 4 mm$^{-1}$), in combination with (iii) a physiologic range of blood volume fractions (about 0.02 to 0.08). In aggregate, results were obtained for a series of studies of the 35 blood samples under 11 different combinations of light scattering and whole blood concentrations over the physiologic range for each of the 35 blood samples. In these samples, the prevalence of iron deficiency, as determined by the HPLC reference method, was 69%.

For all measurements, the light source was tuned to 425 nm and 407 nm (central wavelengths) with a spectral bandwidth of 5 nm FWHM. After acquiring the fluorescence emission spectra for the excitation wavelengths, a shutter was closed to prevent further illumination of the sample, and a dark spectrum was recorded with the same settings.

For the measurement of the Rhodamin B fluorescence standard, the CCD spectrometer's integration time was set to 40 ms, averaging internally over 16 spectra. Including the time required for the wavelength-tuning of the filter unit and the shutter, the measurement time was 4 s. For the measurements of blood samples, which showed much dimmer fluorescence, the integration time was set to 400 ms, averaging internally over 4 spectra, resulting in a total measurement time of 10 s. It was verified that during measurements the signal remained stable.

An exemplary spectral calibration and normalization process is described herein. From all raw, uncorrected spectra $F_{uncorrected}(\lambda)$ the corresponding dark spectrum $D(\lambda)$ was subtracted. The resulting spectrum was multiplied by the factor $C_{excitation}$ which depends on the excitation wavelength and is used to compensate for wavelength- and time-dependent excitation light intensity variations, as well as for optical adjustment variations. In addition, the resulting spectra were divided by the wavelength-dependent transmission of the detection filter $T_{filter}(\lambda)$ and multiplied by a wavelength-dependent factor including optical fiber transmission and spectrometer sensitivity $C_{spectrometer}(\lambda)$. These additional calibration factors allow comparing the corrected spectra $F_{corrected}(\lambda)$ to spectra that were measured using other devices, because influences of the spectral sensitivity of the detection optics and the spectrometer are compensated. The complete calibration procedure is shown in Equation (1):

$$F_{corrected}(\lambda) = [F_{uncorrected}(\lambda) - D(\lambda)] \frac{C_{spectrometer}(\lambda)}{T_{filter}(\lambda)} C_{excitation} \quad (1)$$

To obtain $C_{excitation}$, at first the calibration procedures described above (dark subtraction, filter transmission, detection sensitivity calibration, except for the factor $C_{excitation}$) were applied also to the fluorescence standard measurement $F_{RhodaminB}(\lambda)$. Then, $C_{excitation}$ was calculated as described in Equation (2): The "real" value of the Rhodamin B fluorescence maximum from a reference measurement, $maxR_{RhodaminB}(\lambda)$ was divided by the maximum of the Rhodamin B fluorescence measured by the prototype measurement set-up $maxF_{RhodaminB}(\lambda)$. The reference measurement was recorded by a fluorescence spectrometer (Fluoromax-2, Jobin Yvon GmbH, Unterhaching, Germany), with excitation and detection monochromator adjusted to match excitation and detection bandwidth (5 nm FWHM) of the measurement set-up.

$$C_{excitation} = \frac{maxR_{RhodaminB}(\lambda)}{maxF_{RhodaminB}(\lambda)} \quad (2)$$

Figure 37:
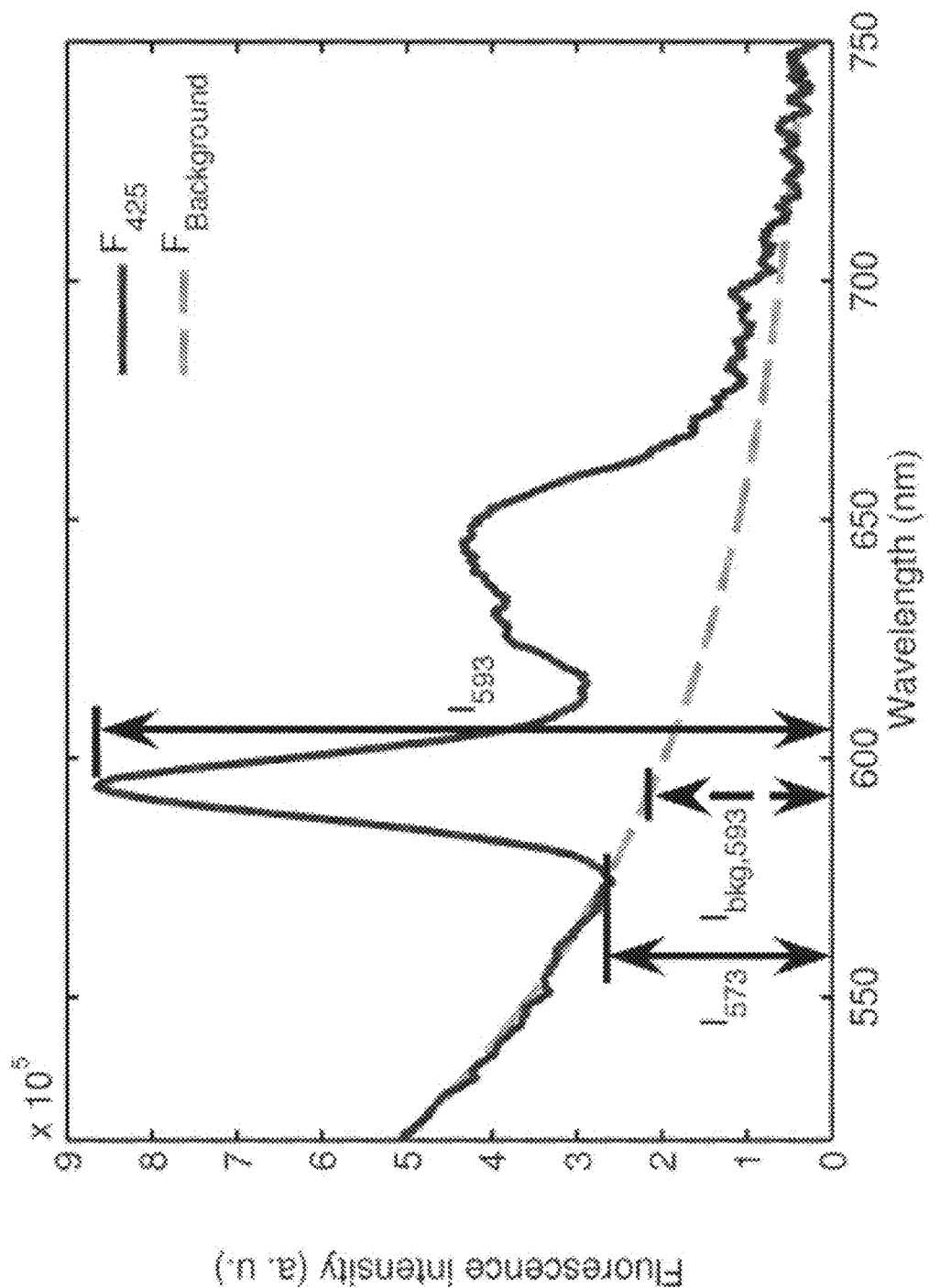
FIG. 37 illustrates an emission spectrum in accordance with an exemplary embodiment of the subject matter described herein.

For purposes of comparison with the novel two wavelength excitation method described herein, a method is described herein which requires one excitation wavelength band (e.g., centered at 425 nm) and two emission wavelength bands (centered at 573 nm and 593 nm) (also referred to as "two wavelength emission method."). For in vitro testing, a sample measurement of patient blood (HPLC determined eZnPP/heme ratio=333 µmol(ZPP)/mol(heme) and PP/heme ratio=605 µmol(PP)/mol(heme)) is shown in FIG. 37. Using the reference HPLC method, the eZnPP and PP concentrations $C_{ZPP}$ and $C_{PP}$ were determined as absolute concentrations in units (nmol/l). Separately, the hemoglobin concentration $C_{Heme}$ was determined by standard laboratory tests in units (g/dl). From the HPLC determined eZnPP and hemoglobin measurements, $C_{ZPP}$ and $C_{Heme}$, the eZnPP/heme ratio (and in the same way, from $C_{PP}$ and $C_{Heme}$ the PP/heme ratio) is calculated by Equation (3), using the hemoglobin subunit's molecular weight 64,458 g/mol.

$$\frac{C_{ZPP}}{C_{Heme}}\left[\frac{\mu mol}{mol}\right] = \frac{C_{ZPP}[nmol/l]}{C_{Heme}[g/dl]} \frac{64.458}{10^4} = \frac{C_{ZPP}[nmol/l]}{0.1551 \cdot C_{Heme}[g/dl]} \quad (3)$$

In FIG. 37, a calibrated fluorescence emission spectrum $F_{425}$ in the wavelength range 520 nm-750 nm is shown (solid line in FIG. 37). The emission maximum of eZnPP is at 593 nm; the background fluorescence from blood plasma $F_{Background}$ was fitted as an exponential decay curve to the data in the spectral range (dashed line in FIG. 37), without contribution from porphyrin emission.

With continued reference to FIG. 37, the eZnPP fluorescence intensity $I_{ZPP}$ was calculated according to Equation (4) below. The measured fluorescence intensities were taken from the calibrated emission spectrum by averaging over the wavelength range 590 nm-596 nm ($I_{593}$) and over 570 nm-576 nm ($I_{573}$). The background fluorescence intensity at 593 nm $I_{bkg,593}$ (double arrows, dashed line) cannot be measured directly, but can be calculated from the fluorescence intensity at 573 nm ($I_{573}$), e.g., 0.8 times the fluorescence intensity at 573 nm. The difference of $I_{593}$ and $I_{bkg,593}$ was used to quantify the eZnPP/heme ratio.

$$I_{ZPP} = I_{593} - I_{bkg,593} = I_{593} - 0.8 \cdot I_{573} \quad (4)$$

According to one aspect of the disclosed subject matter, a novel evaluation method is described herein for reducing the influence of background fluorescence on the detected intensity at 593 nm (also referred to as "two wavelength excitation method.") The method uses two excitation wavelength bands, e.g., 407 and 425 nm. For quantification of the eZnPP/heme ratio, one emission wavelength band, centered at 593 nm, is used. In addition, the ePP/heme ratio is quantified by a second emission wavelength band centered at 627 nm.

Figure 38:
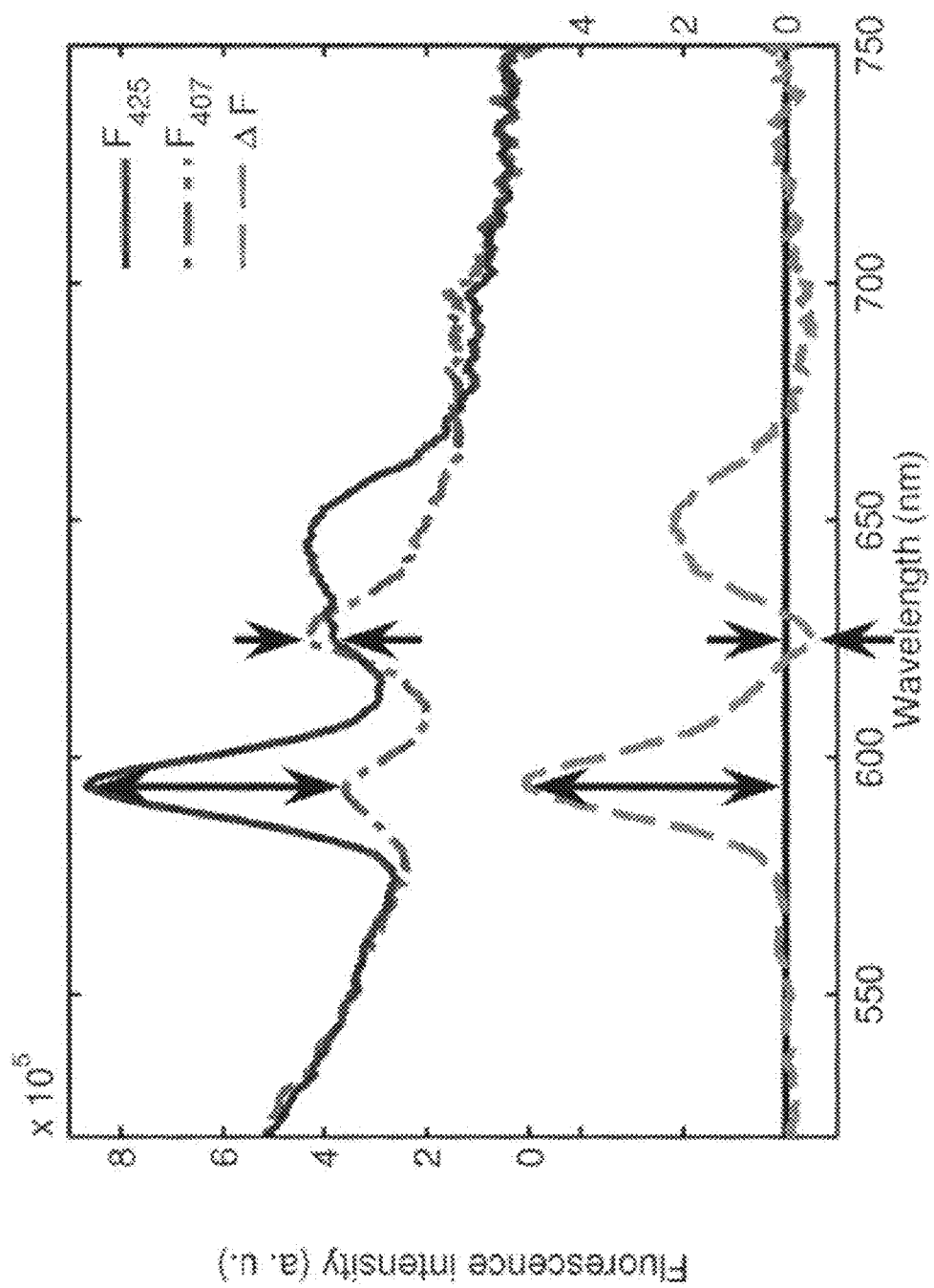
FIG. 38 illustrates an emission spectrum in accordance with an exemplary embodiment of the subject matter described herein.

The method is illustrated in FIG. 38, in which two corrected emission spectra ($F_{425}$; solid line in FIG. 38 and $F_{407}$; dot-dashed line in FIG. 38; left axis description) of the patient blood sample described above are shown; the central excitation wavelengths were 425 nm and 407 nm, respectively. For optimized overlap in the 520 nm-570 nm region, $F_{407}$ was scaled by a factor 1.15. Additionally, the difference between these spectra is shown, which is referred to as "difference spectrum."

In FIG. 38, the differences of the two spectra at 593 nm and at 627 nm are illustrated by dashed line (right axis description) and highlighted by arrows: As the excitation wavelength 407 nm approaches the PP excitation maximum at 397 nm and is far off the eZnPP excitation maximum at 424 nm, the emission spectrum $F_{407}$ shows a pronounced PP fluorescence emission peak, which is found at 627 nm, compared to the lower eZnPP fluorescence peak at 593 nm. The difference in the range 520 nm-570 nm becomes nearly zero, which shows that the background fluorescence is eliminated by calculating the difference spectrum.

Figure 39:
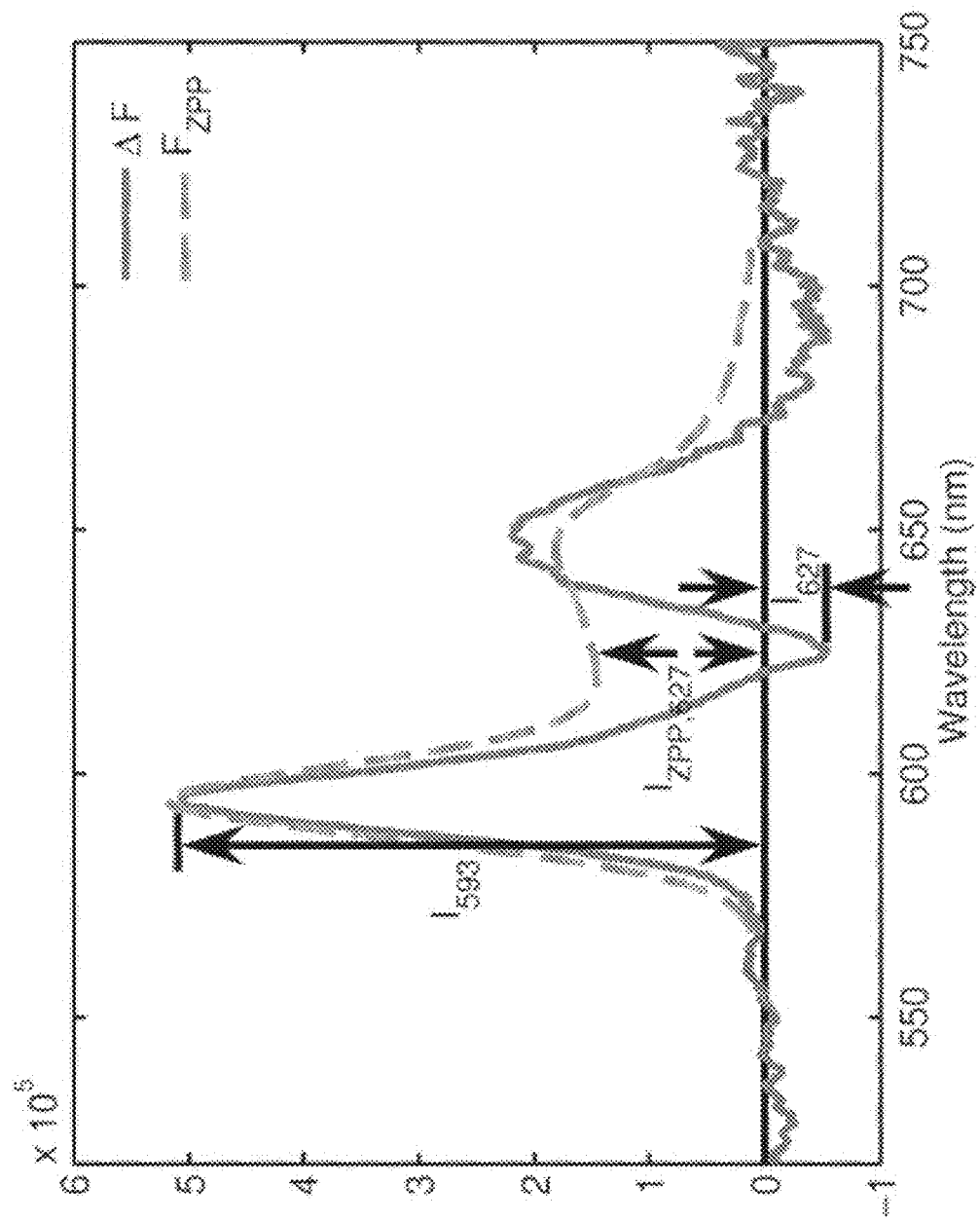
FIG. 39 illustrates a difference spectrum in accordance with an exemplary embodiment of the subject matter described herein.

The difference spectrum is then used to evaluate both eZnPP and PP fluorescence. The eZnPP/heme ratio can be directly quantified by evaluating the fluorescence intensity at 593 nm (averaging over 590 nm-596 nm), as illustrated in FIG. 39. Also, a eZnPP emission spectrum is drafted. At 627 nm, a linear combination of eZnPP and PP fluorescence intensities yields the signal at 627 nm: the eZnPP fluorescence (positive value in the difference spectrum) and the PP fluorescence (negative value in the difference spectrum). Accordingly, a measure for the PP/heme ratio hp can be calculated according to Equation (5): The PP fluorescence is the negative of the detected fluorescence at 627 nm $I_{627}$ plus the eZnPP fluorescence intensity at 627 nm, which equals ⅓ of the eZnPP fluorescence intensity at 593 nm.

$$I_{PP} = -I_{627} + (\tfrac{1}{3})I_{593} \quad (5)$$

The eZnPP/PP ratio was calculated by dividing the eZnPP/heme and the PP/heme ratios, $I_{PP}/I_{PP}$. As both ratios are given in arbitrary units, this calculated eZnpp/PP ratio is also given in arbitrary units.

MATLAB (R2010a, MathWorks®, Natick, Mass., USA) was used for statistical data evaluation. For the statistical evaluation of the correlation of two methods, a linear regression was calculated using a least square fit (function polyfit) and the Pearson product-moment correlation coefficient (PCC) R-value was calculated (function corrcoef) as well as the p-value (e.g., test against the hypothesis of no correlation, t statistics, correlation if p<0.05).

Figure 40:
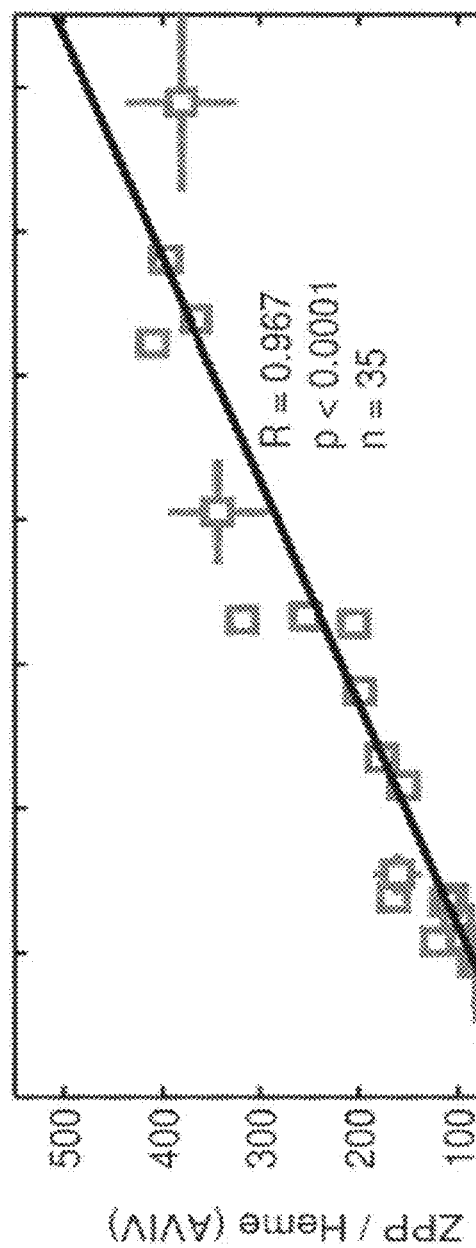
FIGS. 40-41 illustrate a correlation between the eZnPP/heme ratio obtained by a hematofluorometer and by HPLC.
Figure 41:
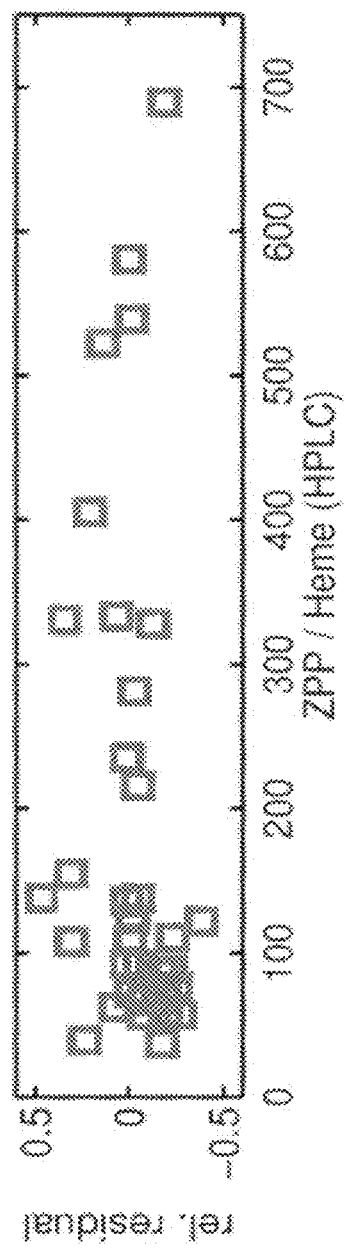

Results of the testing described herein are illustrated in FIGS. 40-47. The eZnPP/heme ratio's correlation of the Aviv hematofluorometer and the reference standard HPLC is shown in FIGS. 40-41. The error bars indicate the precision of each method, being 9% (HPLC) and 15% (hematofluorometer). The linear regression is shown in FIG. 40 (solid black line). The number of samples n=35, the correlation coefficient R=0.967, with a p-value p<0.0001. The relative residuals of the measurement and the linear regression are shown in FIG. 41, being in the range −0.39 . . . +0.46.

Figure 42:
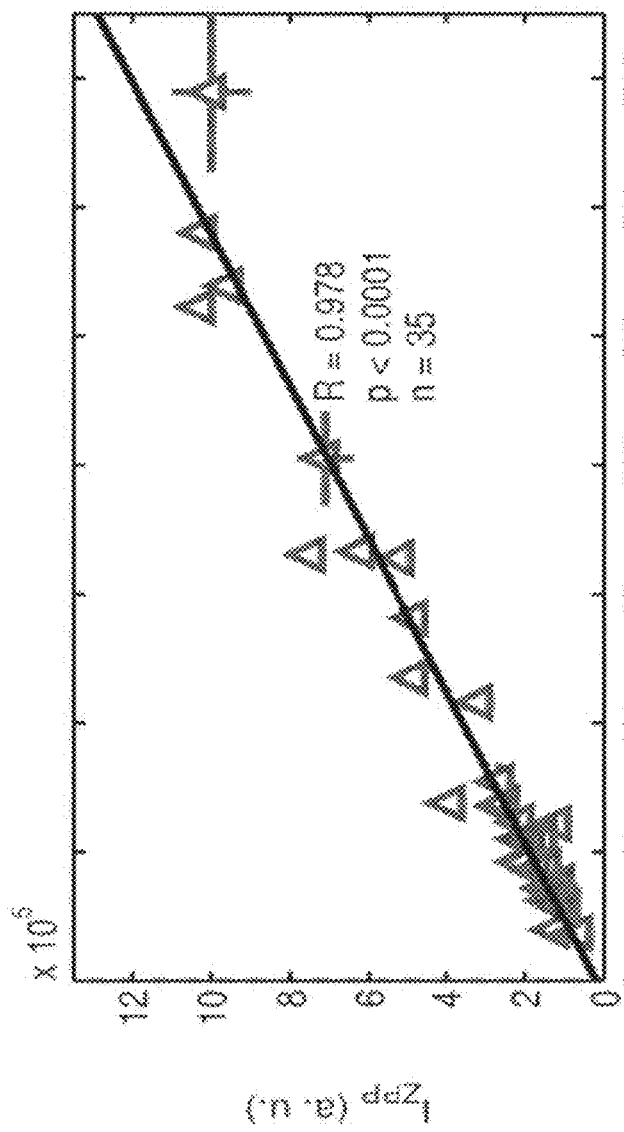
FIGS. 42-43 illustrate a correlation between the measured fluorescence intensity at 593 nm evaluated by HPLC and a method in accordance with an exemplary embodiment of the subject matter described herein.
Figure 43:
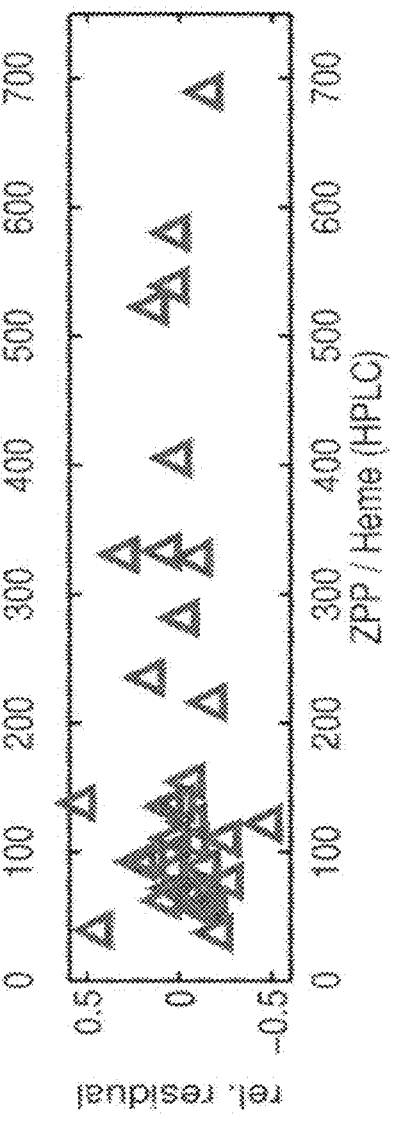

The precision of the eZnPP peak intensity evaluation of the fluorescence spectroscopic measurements was 10%, determined by repeated measurements of the same sample. The correlation of the eZnPP fluorescence intensity at 593 nm evaluated by the two wavelengths emission method (y-axis) and the eZnPP/heme ratio (µmol eZnPP/mol heme) measured by HPLC measurements (x-axis) is shown in FIGS. 42-43. The error bars indicate the precision of each method for three exemplary measurements. The linear regression is shown in FIG. 42 (solid black line). The number of samples n=35, the correlation coefficient R=0.978, with a p-value p<0.0001. The relative residuals of the measurement and the linear regression are shown in FIG. 43, being in the range −0.48 . . . +0.53.

The precision of the evaluated eZnPP peak intensity of the difference spectrum was 10%, determined by repeated measurements of the same sample. The correlation of the eZnPP fluorescence intensity at 593 nm evaluated by the two wavelengths excitation method (y-axis) and the eZnPP/heme ratio (µmol eZnPP/mol heme) measured by HPLC measurements (x-axis) is shown in FIGS. 44-45. The error bars indicate the precision of each method for three exemplary measurements. The linear regression is shown in FIG. 44 (solid black line). The number of samples n=35, the correlation coefficient R=0.976, with a p-value p<0.0001. The relative residuals of the measurement and the linear regression are shown in FIG. 45, being in the range −0.50 . . . +0.57.

The precision of the PP peak intensity, calculated from the intensity of the difference spectrum at 627 nm and 593 nm using Equation (5), was 15%, determined by repeated measurements of the same sample. The correlation between the measured PP fluorescence intensity of the difference spectrum at 627 nm evaluated by the two wavelengths excitation method (y-axis) and the PP/heme ratio (µmol PP/mol heme) measured by HPLC measurements (x-axis) is shown in FIGS. 46-47. The error bars indicate the precision of each method for three exemplary measurements. The linear regression is shown in FIG. 46 (solid black line). The number of samples n=35, the correlation coefficient R=0.996, with a p-value p<0.0001. The relative residuals of the measurement and the linear regression are shown in FIG. 47, being in the range −0.37 . . . +0.50.

Figure 48:
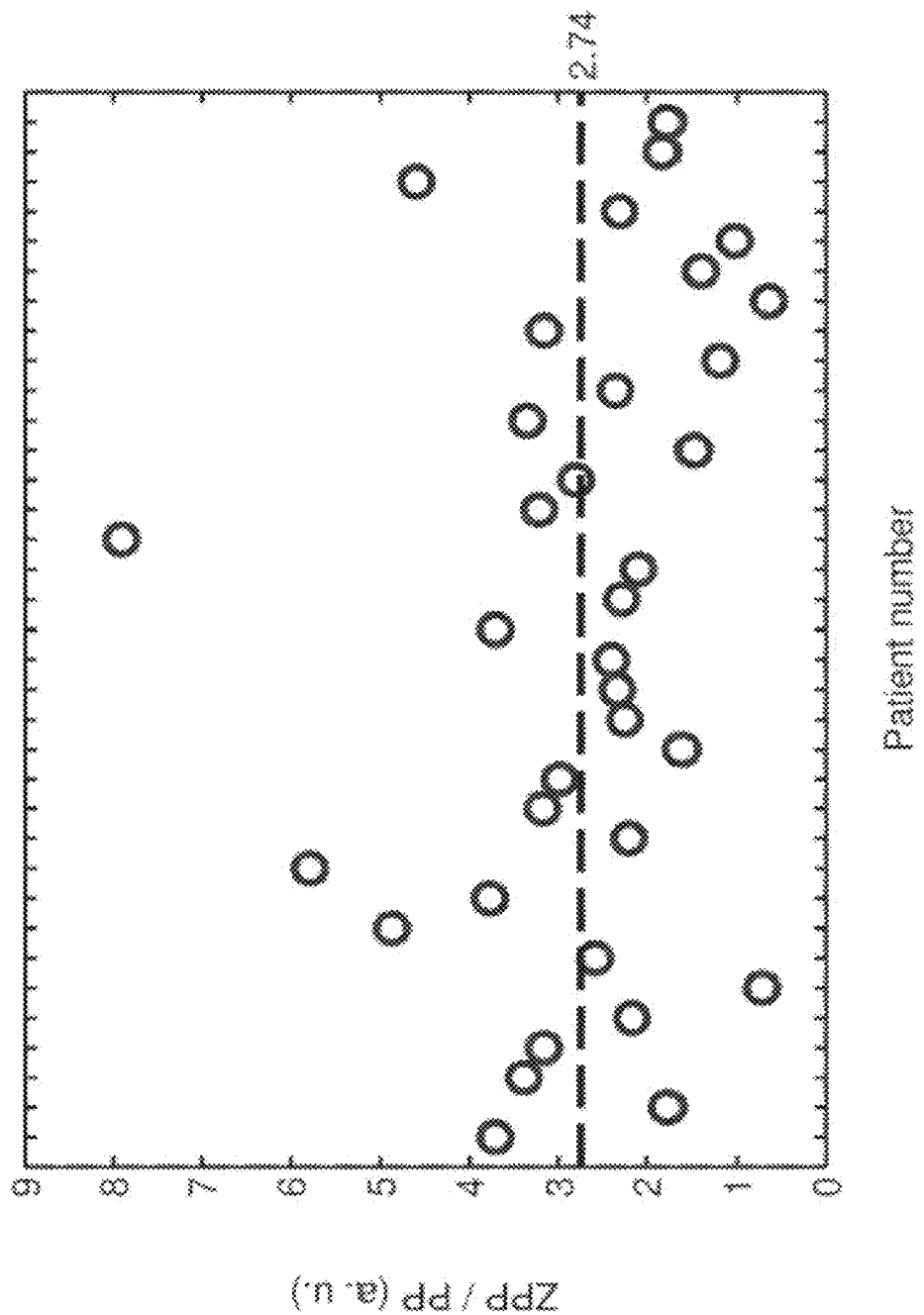
FIG. 48 illustrates the eZnPP/PP ratio calculated from the eZnPP and PP fluorescence intensities as evaluated by a method in accordance with an exemplary embodiment of the subject matter described herein.

The eZnPP/PP ratio, calculated from the eZnPP and PP fluorescence intensities for each patient blood sample (n=35), is shown in FIG. 48. The average eZnPP/PP ratio was 2.74 (arbitrary units), with a range 0.64 . . . 7.91 (arbitrary units).

It is also understood that the terminology used herein is for the purpose of describing particular embodiments only and is not intended to be limiting, since the scope of the present subject matter is limited only by the appended claims.

What is claimed is:

1. An apparatus for noninvasive measurement of a concentration of a fluorescent analyte in the blood of a patient comprising:
    a light source operatively associated with a tunable optical filter, such that the light source is adapted to excite an analyte and blood at alternating first and second wavelengths,
    one or more spectrometers for detecting a portion of the emission spectra of the fluorescent analyte at the first excitation wavelength and the second excitation wavelength; and
    a processor adapted to determine a derived signal representative of the concentration of the analyte based on the difference between the portion of the emission spectra excited at the first excitation wavelength range and the second excitation wavelength range; and determine whether the detected concentration of the fluorescent analyte is below a preselected concentration; and provide an indication that the fluorescent analyte concentration is below the preselected concentration,
    wherein the analyte is selected from the group consisting of: erythrocyte zinc protoporphyrin and erythrocyte protoporphyrin IX, or a combination thereof, and the first and second alternating wavelengths are selected such that the analyte exhibits first and second emission intensities at the first and second wavelengths, the first and second emission intensities being different, and the blood exhibits first and second absorbances at the first and second wavelengths, the first and second absorbances being similar.

2. An apparatus of claim 1, wherein the apparatus is for measurement of a concentration of a fluorescent analyte in whole blood.

3. An apparatus of claim 1, wherein the tunable filter unit comprises a first optical filter and a second optical filter, the first and second optical filters capable of independent variation of the angle of incidence of light provided by the light source.

4. An apparatus of claim 3, wherein the first optical filter and the second optical filter comprises two tunable bandpass filters.

5. An apparatus of claim 3, wherein the tunable filter unit comprises a third filter to correct for offset of the light passing through the first and second optical filters.

6. An apparatus of claim 1, wherein the emission spectra of the fluorescent analyte defines a wavelength range, and wherein the detector includes one or more light sensitive elements receiving light through the one or more optical filters transmitting light in the wavelength range of the emission spectra of the fluorescent analyte.

7. An apparatus of claim 6, wherein the emission spectra of the fluorescent analyte define an emission maximum, wherein a first portion of the one or more spectrometers receives light through the optical filters transmitting light in the wavelength range of the emission spectra of the fluorescent analyte, and wherein a second portion of the one or more spectrometers receives light through optical filters transmitting light in a wavelength range outside the emission maximum of the fluorescent analyte.

8. An apparatus of claim 1, further comprising a probe comprising an optical fiber associated with the light source and an optical fiber associated with the one or more spectrometers.

9. An apparatus of claim 8, wherein the probe comprises a plurality of optical fibers associated with the light source surrounding an optical fiber associated with the one or more spectrometers.

10. An apparatus of claim 8, wherein the probe comprises a plurality of optical fibers associated with the one or more spectrometers surrounding the optical fiber associated with the light source.

11. An apparatus of claim 8, wherein interfiber spacing of the optical fiber associated with the light source and the optical fiber associated with the one or more spectrometers is selected such that the derived signal is insensitive to the blood volume fraction.

12. An apparatus of claim 8, wherein interfiber spacing of the optical fiber associated with the light source and the optical fiber associated with the one or more spectrometers is selected to achieve a maximum detection sensitivity at a selected depth of the tissue.

13. An apparatus of claim 12, wherein the selected depth of the tissue is selected as the depth having the highest expected concentration of the fluorescent analyte.

14. The apparatus of claim 1 wherein the apparatus further comprises a memory that stores multiple analyte readings, wherein the apparatus is configured to determine whether the analyte concentrations are increasing or decreasing when successive analyte readings are obtained for a particular patient and provide an indication that the fluorescent analyte concentration is increasing or decreasing.

15. The apparatus of claim 1 wherein the apparatus further comprises a memory to store health goals for a patient wherein the apparatus is configured to compare the detected analyte concentration to a target concentration and provide an indication whether the target concentration is reached.

16. The apparatus of claim 1 wherein the apparatus is configured to provide a treatment suggestion to a patient after determining the analyst concentration.

17. An apparatus for measurement of a concentration of erythrocyte zinc protoporphyrin (eZnPP) as the eZnPP/heme ratio in the blood of a patient comprising: a light source operatively associated with a tunable optical filter for providing alternating excitation of the tissue at a first wavelength of about 425 nm and a second wavelength of about 407 nm; a detector for detecting a portion of the emission spectra excited at about 425 nm and about 407 nm; and a processor for determining the concentration of eZnPP based on the difference between the portion of the emission spectra excited at about 425 nm and about 407 nm.

18. A method for noninvasive measurement of a concentration of a fluorescent analyte in the blood of a patient comprising: exciting the tissue at an alternating first wavelength and second wavelength, the first and second excitation wavelengths selected such that the fluorescent analyte exhibits a difference in emission intensities at the first and second excitation wavelengths that is greater than that of background fluorophores and light absorbance by blood at the first and second excitation wavelength ranges is similar; detecting a portion of the emission spectra at the first excitation wavelength range and the second excitation wavelength range; and using a processor, determining the concentration of the fluorescent analyte based on the difference between the emission spectra excited at the first excitation wavelength range and the second excitation wavelength range; determining whether the detected concentration of the fluorescent analyte is below a preselected concentration; providing an indication that the fluorescent analyte concentration is below the preselected concentration, and determining whether the analyte concentrations are increasing or decreasing when successive analyte readings are obtained for a particular patient and providing an indication that the fluorescent analyte concentration is increasing or decreasing.

19. The method of claim 18 further comprising comparing the detected analyte concentration to a target concentration and providing an indication whether the target concentration is reached.

20. The method of claim 18 further comprising providing a treatment suggestion to a patient after determining the analyst concentration.

* * * * *